United States Patent
Dean et al.

(10) Patent No.: US 8,513,248 B2
(45) Date of Patent: Aug. 20, 2013

(54) 5,6,7,8-TETRAHYDROIMIDAZO[1,2-A]PYRAZINE DERIVATIVES AS P2X7 MODULATORS

(75) Inventors: David Kenneth Dean, Harlow (GB); Jorge Munoz-Muriedas, Stevenage (GB); Mairi Sime, Harlow (GB); Jon Graham Anthony Steadman, Harlow (GB); Rachel Elizabeth Anne Thewlis, Harlow (GB); Giancarlo Trani, Harlow (GB); Ian David Wall, Stevenage (GB); Daryl Simon Walter, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 13/266,557

(22) PCT Filed: Apr. 28, 2010

(86) PCT No.: PCT/EP2010/055714
§ 371 (c)(1),
(2), (4) Date: Mar. 9, 2012

(87) PCT Pub. No.: WO2010/125101
PCT Pub. Date: Nov. 4, 2010

(65) Prior Publication Data
US 2012/0172366 A1 Jul. 5, 2012

(30) Foreign Application Priority Data
Apr. 30, 2009 (GB) .................................. 0907515.1

(51) Int. Cl.
*A61K 31/495* (2006.01)

(52) U.S. Cl.
USPC ........... 514/249; 544/333; 544/350; 544/405; 546/268.1; 548/202

(58) Field of Classification Search
USPC ...... 514/249; 544/333, 350, 405; 546/268.1; 548/202
See application file for complete search history.

(56) References Cited

FOREIGN PATENT DOCUMENTS
WO WO 2010/125101 * 11/2010

OTHER PUBLICATIONS

Jordan, V. C. Nature Reviews: Drug Discovery, 2, 2003, 205.*
Hackam, et al. JAMA, 296(14), 2006, 1731-1732.*
Guile, et al. Journal of Medicinal Chemistry, 52(10): 3123-3141 (2009).

* cited by examiner

Primary Examiner — Douglas M Willis
(74) Attorney, Agent, or Firm — Nora L. Stein; Theodore R. Furman

(57) ABSTRACT

The present invention provides a compound of formula (I) or a pharmaceutically acceptable salt thereof:

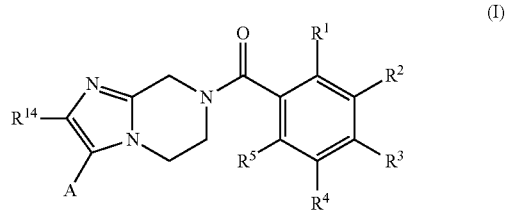

wherein A is hydrogen, $C_{1-4}$alkyl, $C_{3-6}$cycloalkyl, $C_{1-3}$alkoxy, $C_{1-3}$alkoxy $C_{1-4}$alkyl, $C_{1-2}$fluoroalkyl, halogen, $NR^6R^7$, optionally substituted heteroaryl (Het), or optionally substituted phenyl, and $R^1$, $R^2$, $R^3$, $R^4$, $R^5$, $R^6$ and $R^7$ are as defined in the description.

The compounds or salts are thought to modulate P2X7 receptor function and to be capable of antagonizing the effects of ATP at the P2X7 receptor. The invention also provides the use of the compound or salt in the treatment or prophylaxis of, for example, inflammatory pain, neuropathic pain, visceral pain, rheumatoid arthritis or osteoarthritis or neurodegenerative disorders.

3 Claims, No Drawings

5,6,7,8-TETRAHYDROIMIDAZO[1,2-A]PYRAZINE DERIVATIVES AS P2X7 MODULATORS

This application is a §371 of International Application No. PCT/EP2010/055714, filed 28 Apr. 2010, which claims the priority of Great Britain Application No. 0907515.1, filed 30 Apr. 2009, which are incorporated herein in their entireties.

The present invention relates to fused bicyclic derivatives, specifically fused imidazole derivatives, which modulate P2X7 receptor function and are capable of antagonizing the effects of ATP at the P2X7 receptor ("P2X7 receptor antagonists"); to processes for their preparation; to pharmaceutical compositions containing them; and to the use of such compounds in therapy.

BACKGROUND OF THE INVENTION

The P2X7 receptor is a ligand-gated ion-channel which is expressed in cells of the hematopoietic lineage, e.g. macrophages, microglia, mast cells, and lymphocytes (T and B) (see, for example, Collo, et al. Neuropharmacology, Vol. 36, pp 1277-1283 (1997)), and is activated by extracellular nucleotides, particularly adenosine triphosphate (ATP). Activation of P2X7 receptors has been implicated in giant cell formation, degranulation, cytolytic cell death, CD62L shedding, regulation of cell proliferation, and release of proinflammatory cytokines such as interleukin 1 beta (IL-1β) (e.g. Ferrari, et al., J. Immunol., Vol. 176, pp 3877-3883 (2006)), interleukin 18 (IL-18), and tumour necrosis factor alpha (TNFα) (e.g. Hide, et al. Journal of Neurochemistry, Vol. 75, pp 965-972 (2000)). P2X7 receptors are also located on antigen presenting cells, keratinocytes, parotid cells, hepatocytes, erythrocytes, erythroleukaemic cells, monocytes, fibroblasts, bone marrow cells, neurones, and renal mesangial cells. Furthermore, the P2X7 receptor is expressed by presynaptic terminals in the central and peripheral nervous systems and has been shown to mediate glutamate release in glial cells (Anderson, C. et al. Drug. Dev. Res., Vol. 50, page 92 (2000)).

The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders. Recent preclinical in vivo studies have directly implicated the P2X7 receptor in both inflammatory and neuropathic pain (Dell'Antonio et al., Neurosci. Lett., Vol. 327, pp 87-90 (2002), Chessell, I P., et al., Pain, Vol. 114, pp 386-396 (2005), Honore et al., J. Pharmacol. Exp. Ther., Vol. 319, p1376-1385 (2006)) while there is in vitro evidence that P2X7 receptors mediate microglial cell induced death of cortical neurons (Skaper, S. D., et al., Glia, Vol. 54, p234-242 (2006)). In addition, up-regulation of the P2X7 receptor has been observed around β-amyloid plaques in a transgenic mouse model of Alzheimer's disease (Parvathenani, L. et al. J. Biol. Chem., Vol. 278(15), pp 13309-13317 (2003)).

SUMMARY OF THE INVENTION

The present invention provides compounds which modulate P2X7 receptor function and are capable of antagonizing the effects of ATP at the P2X7 receptor ("P2X7 receptor antagonists").

In a first aspect of the invention, there is provided a compound of formula (I) or a pharmaceutically acceptable salt thereof:

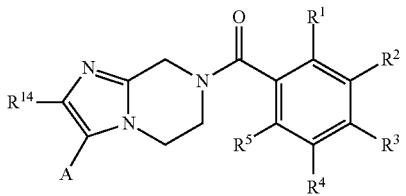

wherein:
A is hydrogen, $C_{1-4}$alkyl (e.g. methyl or ethyl), $C_{3-6}$cycloalkyl (e.g. cyclopropyl, cyclopentyl or cyclohexyl), $C_{1-3}$alkoxy (e.g. methoxy), $C_{1-3}$alkoxy $C_{1-4}$alkyl (e.g. methoxyethyl), $C_{1-2}$fluoroalkyl (e.g. trifluoromethyl), halogen (e.g. bromine, chlorine or iodine), $NR^6R^7$, Het, or phenyl wherein the phenyl is optionally substituted by one, two or three (e.g. one or two) substituents independently being fluorine, chlorine, $C_{1-3}$alkyl (e.g. methyl), OH, methoxy or deuterium;
wherein Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
iii) a 9 or 10-membered heteroaromatic bicyclic ring containing one, two or three (e.g. one or two) ring nitrogen atoms;
and wherein Het is optionally substituted with one or two substituents independently being $C_{1-3}$ alkyl (e.g. methyl), fluorine, chlorine, OH (including a tautomer thereof), methoxy or deuterium;
and wherein:
$R^1$ is hydrogen, chlorine, fluorine, bromine, $C_1$fluoroalkyl (e.g. —$CF_3$), cyano or $C_{1-3}$alkyl (e.g. methyl);
$R^2$ is hydrogen, fluorine, chlorine, bromine, $C_1$fluoroalkyl (e.g. —$CF_3$), cyano or $C_{1-3}$alkyl (e.g. methyl),
$R^3$ is hydrogen, fluorine, chlorine or $C_{1-3}$alkyl (e.g. methyl),
$R^4$ is hydrogen;
$R^5$ is hydrogen, fluorine, chlorine or methyl;
$R^6$ and $R^7$ independently are hydrogen or $C_{1-3}$alkyl (e.g. hydrogen or methyl);
or $R^6$ and $R^7$ are taken together and are —$(CH_2)_2$—O—$(CH_2)_2$—, —$(CH_2)_2$—O—$(CH_2)_3$—, or —$(CH_2)_{n^1}$— wherein $n^1$ is 3, 4, 5 or 6 (e.g. 3, 4 or 5); and
$R^{14}$ is hydrogen, $C_{1-6}$alkyl, $C_{1-2}$fluoroalkyl, $C_{3-6}$cycloalkyl, halogen (e.g. bromine, chlorine or iodine), or phenyl wherein the phenyl is optionally substituted by one or two substituents independently being fluorine, chlorine, methyl, —$CF_3$ or methoxy;
wherein, when A is hydrogen, $C_{1-4}$alkyl, or $C_{1-3}$alkyl (e.g. methyl), $C_{1-3}$alkoxy, $C_{1-3}$alkoxy $C_{1-4}$alkyl, $C_{1-2}$fluoroalkyl, halogen or $NR^6R^7$, then $R^1$ is chlorine, fluorine, bromine, $C_1$fluoroalkyl (e.g. —$CF_3$), cyano or $C_{1-3}$alkyl (e.g. methyl), and at least one of $R^2$ and $R^3$ is other than hydrogen;
and when A is Het or optionally substituted phenyl, then $R^1$ is hydrogen, chlorine, fluorine, bromine, $C_1$fluoroalkyl (e.g. —$CF_3$), cyano or $C_{1-3}$alkyl (e.g. methyl), at least one of $R^1$, $R^2$ and $R^3$ is other than hydrogen, and $R^{14}$ is hydrogen, $C_{1-6}$alkyl, $C_{1-2}$fluoroalkyl, $C_{3-6}$cycloalkyl or halogen;
and wherein, when $R^5$ is fluorine, chlorine or methyl, then $R^1$ is chlorine, fluorine, $C_1$fluoroalkyl (e.g. —$CF_3$) or methyl and $R^2$ is hydrogen.

DETAILED DESCRIPTION OF THE INVENTION

As used herein, the term "alkyl" (when used as a group or as part of a group) refers to a straight or branched hydrocarbon chain containing the specified number of carbon atoms. For example, $C_{1-6}$alkyl means a straight or branched hydrocarbon chain containing at least 1 and at most 6 carbon atoms. Alkyl or $C_{1-6}$alkyl can for example be, but are not limited to: methyl (Me), ethyl (Et), n-propyl (propyl), isopropyl (1-methylethyl), n-butyl (butyl), isobutyl, sec-butyl, t-butyl, n-pentyl, 3-methylbutyl, 1-ethylpropyl, n-hexyl or isohexyl.

"$C_{1-2}$fluoroalkyl" means $C_{1-2}$alkyl substituted by one, two or three fluorine atoms; for example methyl substituted by one, two or three fluorine atoms (i.e. trifluoromethyl ($—CF_3$), difluoromethyl or monofluoromethyl); in particular trifluoromethyl ($—CF_3$).

"$C_{3-6}$cycloalkyl" can be cyclopropyl, cyclobutyl, cyclopentyl, or cyclohexyl.

The term "halogen" is used herein to mean, unless otherwise stated, a group which is fluorine, chlorine, bromine or iodine. A halogen can for example be fluorine or chlorine.

It is to be understood that the present invention covers and discloses all possible combinations of particular, preferred, suitable, or other embodiments of groups or features (e.g. of A, Het, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $X^1$, $X^2$, $X^3$, $X^4$, $X^5$, $X^8$, $X^9$, $X^{10}$, and $X^{11}$, and/or $n^1$), e.g. covers and discloses all possible combinations of embodiments of different groups or features, which embodiments are described herein.

In one embodiment of the invention, there is provided a compound of formula (I) or a pharmaceutically acceptable salt thereof:

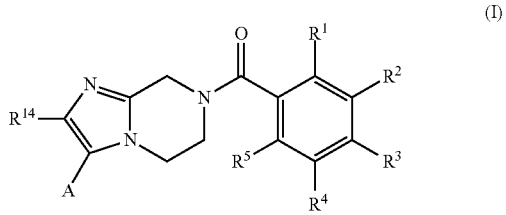

(I)

wherein:
A is hydrogen, $C_{1-4}$alkyl (e.g. methyl or ethyl), $C_{1-3}$alkoxy (e.g. methoxy), $C_{1-2}$fluoroalkyl (e.g. trifluoromethyl), halogen (e.g. bromine, chlorine or iodine), $NR^6R^7$, Het, or phenyl wherein the phenyl is optionally substituted by one, two or three (e.g. one or two) substituents independently being fluorine, chlorine, $C_{1-3}$alkyl (e.g. methyl) or methoxy;
wherein Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
and wherein Het is optionally substituted with one or two substituents independently being $C_{1-3}$ alkyl (e.g. methyl), fluorine, chlorine, OH (including a tautomer thereof), or methoxy;
and wherein:
$R^1$ is hydrogen, chlorine, fluorine, bromine, $C_1$fluoroalkyl (e.g. $—CF_3$), cyano or $C_{1-3}$alkyl (e.g. methyl);
$R^2$ is hydrogen, fluorine, chlorine, bromine, $C_1$fluoroalkyl (e.g. $—CF_3$), cyano or $C_{1-3}$alkyl (e.g. methyl),
$R^3$ is hydrogen, fluorine or chlorine,
$R^4$ is hydrogen;
$R^5$ is hydrogen, fluorine, chlorine or methyl;

$R^6$ and $R^7$ independently are hydrogen or $C_{1-3}$alkyl (e.g. hydrogen or methyl);
or $R^6$ and $R^7$ are taken together and are $—(CH_2)_2—O—(CH_2)_2—$, $—(CH_2)_2—O—(CH_2)_3—$, or $—(CH_2)_{n^1}—$ wherein $n^1$ is 3, 4, 5 or 6 (e.g. 3, 4 or 5); and
$R^{14}$ is hydrogen, $C_{1-6}$alkyl, $C_{1-2}$fluoroalkyl, $C_{3-6}$cycloalkyl, halogen, or phenyl wherein the phenyl is optionally substituted by one or two substituents independently being fluorine, chlorine, methyl, $—CF_3$ or methoxy;
wherein, when A is hydrogen, $C_{1-4}$alkyl, $C_{1-3}$alkoxy, $C_{1-2}$fluoroalkyl, halogen or $NR^6R^7$, then $R^1$ is chlorine, fluorine, bromine, $C_1$fluoroalkyl (e.g. $—CF_3$), cyano or $C_{1-3}$alkyl (e.g. methyl), and at least one of $R^2$ and $R^3$ is other than hydrogen;
and when A is Het or optionally substituted phenyl, then $R^1$ is hydrogen, chlorine, fluorine, bromine, $C_1$fluoroalkyl (e.g. $—CF_3$), cyano or $C_{1-3}$alkyl (e.g. methyl), at least one of $R^1$, $R^2$ and $R^3$ is other than hydrogen, and $R^{14}$ is hydrogen, $C_{1-6}$alkyl, $C_{1-2}$fluoroalkyl, $C_{3-6}$cycloalkyl or halogen;
and wherein, when $R^5$ is fluorine, chlorine or methyl, then $R^1$ is chlorine, fluorine, $C_1$fluoroalkyl (e.g. $—CF_3$) or methyl and $R^2$ is hydrogen.

In a particular embodiment, A is methyl, ethyl, methoxy, $C_1$fluoroalkyl (e.g. trifluoromethyl), halogen (e.g. bromine, chlorine or iodine, such as bromine or iodine), $NR^6R^7$, Het, or phenyl wherein the phenyl is optionally substituted by one, two or three (e.g. one or two) substituents independently being fluorine, chlorine, $C_{1-3}$alkyl (e.g. methyl) or methoxy.

In a more particular embodiment, A is trifluoromethyl, bromine, iodine, $NR^6R^7$, Het, or phenyl wherein the phenyl is optionally substituted by one or two substituents independently being fluorine, chlorine, methyl or methoxy. In a still more particular embodiment, A is Het or phenyl wherein the phenyl is optionally substituted by one or two substituents independently being fluorine, chlorine, methyl or methoxy.

In one embodiment when A is phenyl, then the A is optionally substituted by one, two or three (e.g. one or two) substituents independently being fluorine, chlorine, $C_{1-3}$alkyl (e.g. methyl), $C_1$fluoroalkyl (e.g. $—CF_3$), OH, or methoxy. In a further embodiment, when A is phenyl, then the phenyl is optionally substituted by one, two or three (e.g. one or two) substituents independently being fluorine, chlorine, $C_{1-3}$alkyl (e.g. methyl) or methoxy.

In one embodiment when A is phenyl, then the phenyl is optionally substituted by one substituent being fluorine, chlorine, $C_{1-3}$alkyl (e.g. methyl), OH, methoxy or deuterium. In a further embodiment when A is phenyl, then the phenyl is optionally substituted by one substituent being fluorine, chlorine, $C_{1-3}$alkyl (e.g. methyl), OH or methoxy.

When A is phenyl is optionally substituted by one or two substituents independently being fluorine, chlorine, methyl, OH or methoxy, then: in a particular embodiment A is phenyl optionally substituted by one or two fluorine substituents, one or two chlorine substituents, one OH substituent, one OH substituent and one fluorine substituent, one methyl substituent or one methoxy substituent, in a more particular embodiment, A is phenyl optionally substituted with one or two (e.g one) fluorine substituents, one chlorine substituent or one methyl substituent, in a yet more particular embodiment A is phenyl optionally substituted by one or two fluorine substituents. In a particular embodiment, A is unsubstituted phenyl, 4-fluorophenyl, 4-chlorophenyl, 2-methyl phenyl, in a further particular embodiment, A is unsubstituted phenyl or 4-fluorophenyl, or in a more particular embodiment A is 4-fluorophenyl or 2,4-difluorophenyl; or preferably A is 4-fluorophenyl.

In one embodiment, A is hydrogen, halogen (in particular bromine, chlorine or iodine), Het, or phenyl wherein the phenyl is optionally substituted by one or two (e.g. one) substituents independently being fluorine, chlorine or methyl (e.g. fluorine or methyl). Preferably, A is halogen (in particular bromine or iodine), Het, or phenyl wherein the phenyl is optionally substituted by one or two (e.g. one) substituents independently being fluorine, chlorine or methyl (e.g. fluorine or methyl).

In one particular embodiment, A is hydrogen, bromine, chlorine, iodine, Het, phenyl, 4-fluorophenyl, 2,4-difluorophenyl, 2-methylphenyl or 4-chlorophenyl. More particularly, A is bromine, iodine, Het, phenyl, 4-fluorophenyl or 2,4-difluorophenyl. In another particular embodiment, A is bromine, iodine, Het, phenyl, 4-fluorophenyl, 2,4-difluorophenyl, 2-methylphenyl or 4-chlorophenyl. More particularly, A is bromine, iodine, Het, phenyl, 4-fluorophenyl or 2,4-difluorophenyl.

In a particular embodiment, Het is:
i) a 6-membered heteroaromatic monocyclic ring containing one, two or three (e.g. one or two) ring-nitrogen atoms, or
ii) a 5-membered heteroaromatic monocyclic ring containing one, two or three (e.g. one or two) ring heteroatoms independently being N, O or S, wherein no more than one of the 5-membered ring heteroatoms is O or S;
and wherein Het is optionally substituted with one or two substituents independently being methyl or fluorine.

In one particular embodiment, Het is unsubstituted or substituted with one fluorine atom.

Preferably, Het is a carbon-linked heteroaromatic ring system, i.e. the heteroaromatic ring is linked to the 3-position of the tetrahydroimidazo[1,2-a]pyrazine via a bond to a carbon atom in the heteroaromatic ring system of Het.

In a particular embodiment, when Het is the optionally substituted 5-membered heteroaromatic monocyclic ring containing one, two or three ring heteroatoms independently being N, O or S, wherein no more than one of the 5-membered ring heteroatoms is O or S; then at least one of the 5-membered ring heteroatoms is nitrogen. Preferably, when Het is the optionally substituted 5-membered heteroaromatic monocyclic ring, Het is unsubstituted or substituted with one fluorine atom, and more preferably Het is unsubstituted.

In a particular embodiment, when Het is an optionally substituted 6-membered heteroaromatic monocyclic ring containing one, two or three (e.g. one or two) ring-nitrogen atoms, then Het is of sub-formula (a):

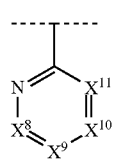
(a)

wherein none, one or two (in particular none or one) of $X^8$, $X^9$, $X^{10}$, and $X^{11}$ are a nitrogen atom, and
the remainder of $X^8$, $X^9$, $X^{10}$, and $X^{11}$ are C—$R^8$, C—$R^9$, C—$R^{10}$, and C—$R^{11}$ respectively in which $R^8$, $R^9$, $R^{10}$, and $R^{11}$ are independently hydrogen, deuterium, $C_{1-3}$ alkyl (e.g. methyl), fluorine, chlorine, OH (including a tautomer thereof) or methoxy.

In a particular embodiment, $R^8$, $R^9$, $R^{10}$, and $R^{11}$ are independently hydrogen, deuterium, methyl, fluorine, chlorine, or methoxy; more particularly hydrogen, methyl or fluorine.

In one embodiment, $R^8$ is selected from hydrogen, methyl, fluorine, chlorine, OH or methoxy, for example chlorine or methoxy. In another embodiment, $R^{19}$ is selected from hydrogen, deuterium, $C_{1-3}$ alkyl (e.g. methyl), fluorine or OH (including a tautomer thereof), for example hydrogen, methyl or fluorine. In a further particular embodiment $R^9$ is hydrogen or fluorine.

In a particular embodiment, when Het is an optionally substituted 6-membered heteroaromatic monocyclic ring, then Het is of sub-formula (a) as defined in any one of the Examples herein.

In a more particular embodiment, when Het is an optionally substituted 6-membered heteroaromatic monocyclic ring, then Het is of sub-formula (a1) to (a25):

(a1)

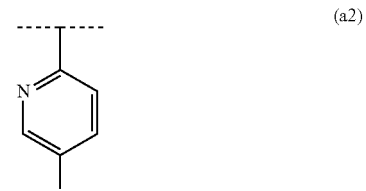
(a2)

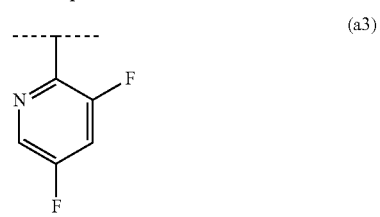
(a3)

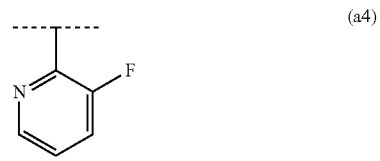
(a4)

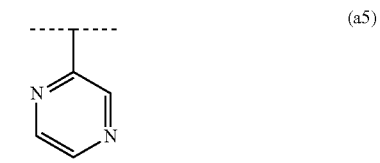
(a5)

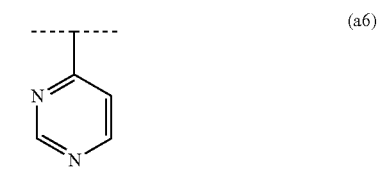
(a6)

(a7)

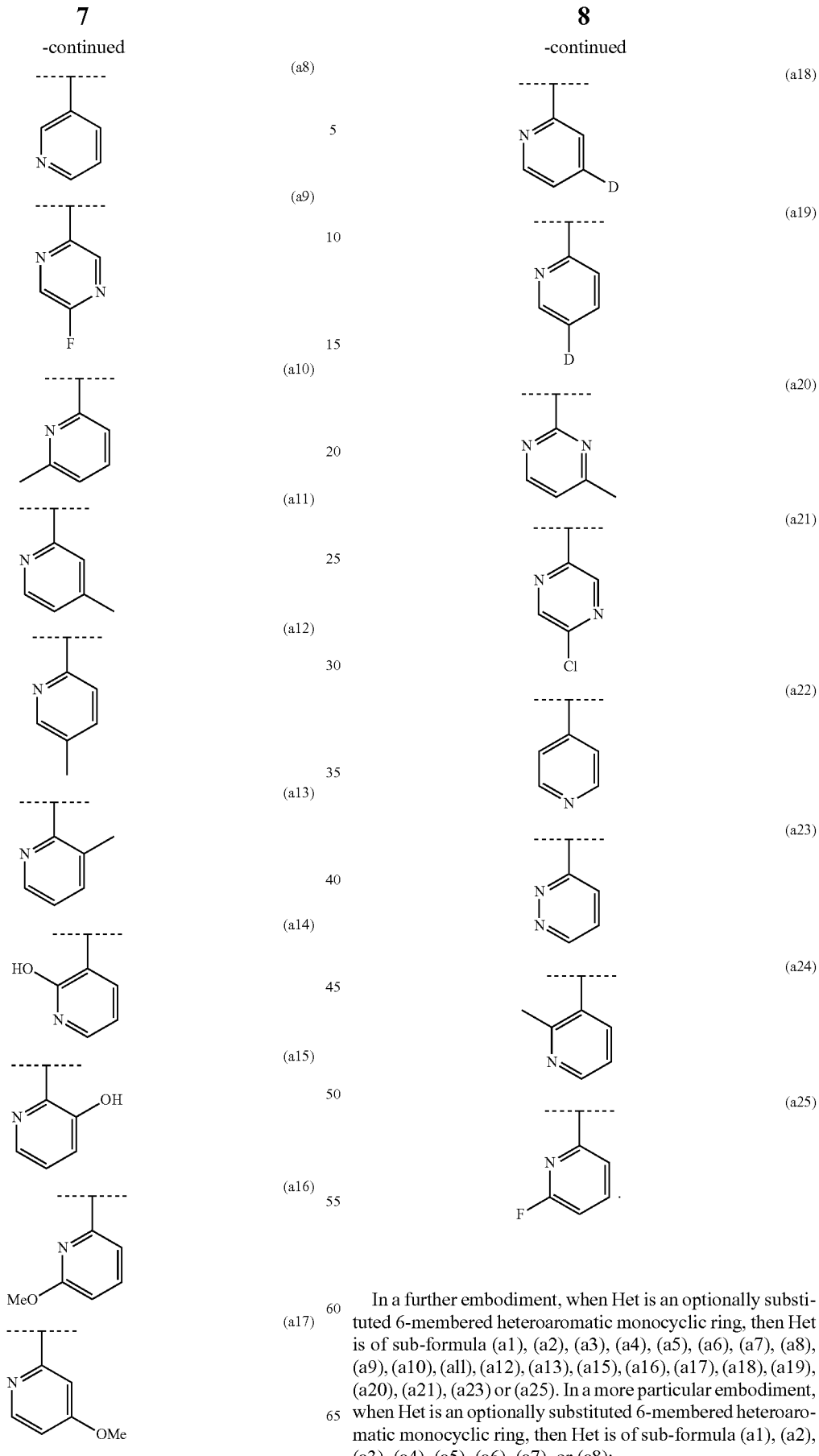
In a further embodiment, when Het is an optionally substituted 6-membered heteroaromatic monocyclic ring, then Het is of sub-formula (a1), (a2), (a3), (a4), (a5), (a6), (a7), (a8), (a9), (a10), (a11), (a12), (a13), (a15), (a16), (a17), (a18), (a19), (a20), (a21), (a23) or (a25). In a more particular embodiment, when Het is an optionally substituted 6-membered heteroaromatic monocyclic ring, then Het is of sub-formula (a1), (a2), (a3), (a4), (a5), (a6), (a7), or (a8):

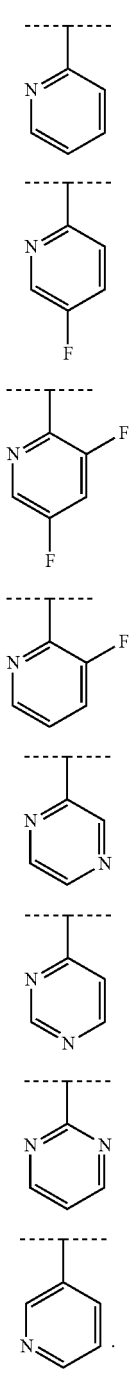

(a1)
(a2)
(a3)
(a4)
(a5)
(a6)
(a7)
(a8)

In another embodiment, when Het is an optionally substituted 6-membered heteroaromatic monocyclic ring, then Het is of sub-formula (a1), (a2), (a6), (a7) or (a8).

Preferably, when Het is an optionally substituted 6-membered heteroaromatic monocyclic ring, then Het is of sub-formula (a1), (a2), (a3), (a4), (a5), (a6) or (a8).

In a particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; then Het is of sub-formula (b1), (b2), (b3), (b4) or (b5):

(b1)
(b2)
(b3)
(b4)
(b5)

wherein:
$X^1$ is O, S or $NR^{12}$;
$X^2$, $X^3$, $X^4$, and $X^5$ independently are N or $CR^{13}$, provided that there are only one, two or three (such as only one or two) ring heteroatoms present in the 5-membered heteroaromatic monocyclic ring of Het; and
$X^6$ is O, S; and wherein:
$R^{12}$ is hydrogen or $C_{1-3}$ alkyl (particularly hydrogen or methyl); and
each $R^{13}$ independently is hydrogen, $C_{1-3}$ alkyl (e.g. methyl), fluorine, chlorine, OH (including a tautomer thereof) or methoxy (particularly fluorine or methyl);
provided that $R^{12}$ and each $R^{13}$ are such that the 5-membered heteroaromatic monocyclic ring Het is optionally substituted with one or two substituents.

In a particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; then Het is of sub-formula (b1), (b2), (b3), (b4) or (b5'):

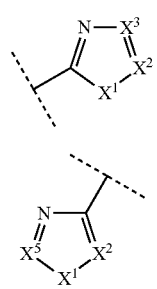

(b1)
(b2)

(b3)

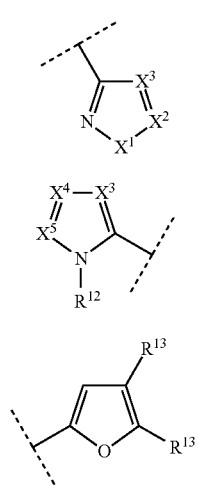

(b4)

(b5')

wherein:
$X^1$ is O, S or $NR^{12}$; and
$X^2$, $X^3$, $X^4$, and $X^5$ independently are N or $CR^{13}$, provided that there are only one, two or three (such as only one or two) ring heteroatoms present in the 5-membered heteroaromatic monocyclic ring of Het; and wherein $R^{12}$ is hydrogen or $C_{1-3}$ alkyl (particularly hydrogen or methyl); and each $R^{13}$ independently is hydrogen, $C_{1-3}$ alkyl (e.g. methyl), fluorine, chlorine, OH (including a tautomer thereof) or methoxy (particularly fluorine or methyl);

provided that $R^{12}$ and each $R^{13}$ are such that the 5-membered heteroaromatic monocyclic ring Het is optionally substituted with one or two substituents.

In a more particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; and Het is of sub-formula (b1), (b2), (b3) or (b4); then Het is one of the following sub-formulae, in which each $R^{12}$ independently is hydrogen or methyl, and each $R^{13}$ independently is hydrogen or methyl:

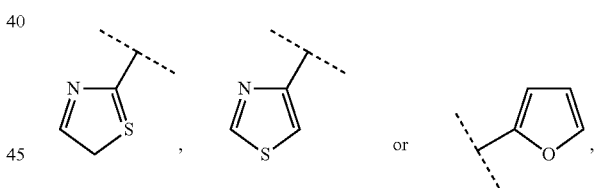

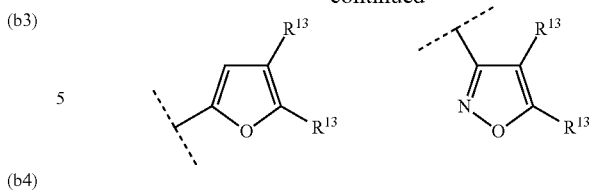

In a particular embodiment, when Het is an optionally substituted 5-membered heteroaromatic monocyclic ring containing one, two or three (e.g. one or two) ring heteroatoms independently being N, O or S, wherein no more than one of the 5-membered ring heteroatoms is O or S; and Het is of sub-formula (b1), (b2), (b3) or (b4); then Het is one of the following sub-formulae, in which each $R^{12}$ independently is hydrogen or methyl, and each $R^{13}$ independently is hydrogen or methyl:

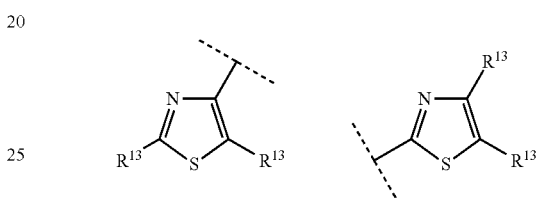

Preferably, when Het is one of the above sub-formulae containing two $R^{13}$ groups, then one of the $R^{13}$ is hydrogen, and the other of the $R^{13}$ is hydrogen or methyl. In one particular embodiment, both $R^{13}$ are hydrogen.

In a particular embodiment, when Het is an optionally substituted 5-membered heteroaromatic monocyclic ring, then Het is as defined in any one of the Examples herein.

In a more particular embodiment, when Het is an optionally substituted 5-membered heteroaromatic monocyclic ring, then Het is

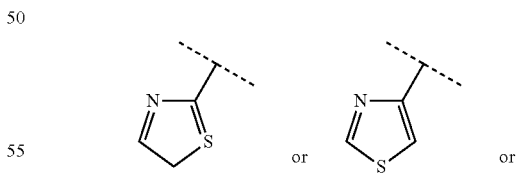

preferably

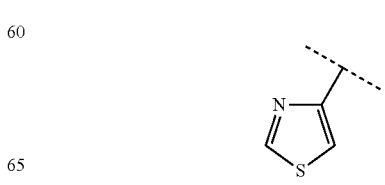

more preferably

Therefore, in one embodiment, A is hydrogen, bromine, chlorine, iodine, phenyl, 4-fluorophenyl, 2,4-difluorophenyl, 2-methylphenyl or 4-chlorophenyl or A is Het, wherein Het is a 6-membered heteroaromatic monocyclic ring of sub-formula (a1), (a2), (a3), (a4), (a5), (a6), (a7) or (a8); or wherein Het is a 5-membered heteroaromatic monocyclic ring which is:

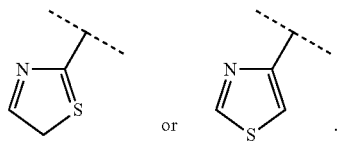

Therefore, preferably, A is bromine, iodine, phenyl, 4-fluorophenyl, 2,4-difluorophenyl, or A is Het, wherein Het is a 6-membered heteroaromatic monocyclic ring of sub-formula (a1), (a2), (a3), (a4), (a5), (a6) or (a8), or Het is a 5-membered heteroaromatic monocyclic ring which is:

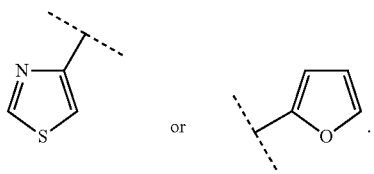

In a further preferred embodiment, A is hydrogen, bromine, chlorine, iodine, phenyl, 4-fluorophenyl, 2,4-difluorophenyl, 2-methylphenyl or 4-chlorophenyl or A is Het, wherein Het is a 6-membered heteroaromatic monocyclic ring of sub-formula (a1), (a2), (a6), (a7) or (a8); or wherein Het is a 5-membered heteroaromatic monocyclic ring which is:

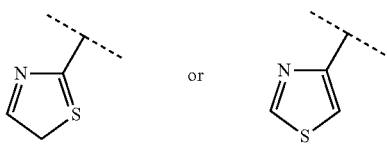

More preferably, A is bromine, iodine, phenyl, 4-fluorophenyl, 2,4-difluorophenyl, or A is Het, wherein Het is a 6-membered heteroaromatic monocyclic ring of sub-formula (a1), (a2), (a3), (a4), (a5), (a6) or (a8):

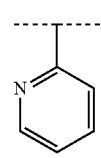
(a1)

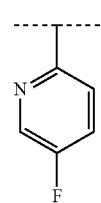
(a2)

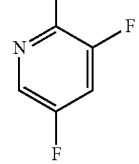
(a3)

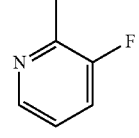
(a4)

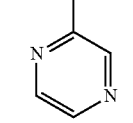
(a5)

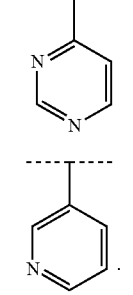
(a6)

(a8)

In a particular embodiment, $R^1$ is hydrogen, chlorine, fluorine, $C_1$fluoroalkyl (e.g. —$CF_3$), cyano or methyl. More particularly, $R^1$ is chlorine, fluorine, $C_1$fluoroalkyl (e.g. —$CF_3$), or methyl. Still more particularly, $R^1$ is chlorine, fluorine or methyl. Yet more particularly, $R^1$ is chlorine or fluorine.

Preferably, $R^1$ is chlorine.

In a particular embodiment, $R^2$ is hydrogen, fluorine, chlorine, $C_1$fluoroalkyl (e.g. —$CF_3$), or methyl.

Preferably, $R^2$ is hydrogen, fluorine, chlorine, —$CF_3$ or methyl; in particular hydrogen, fluorine, chlorine or —$CF_3$.

In one embodiment, $R^2$ is chlorine or —$CF_3$.

In one embodiment, $R^3$ is hydrogen, fluorine or chlorine; especially hydrogen or fluorine.

In a particular embodiment, $R^5$ is hydrogen, fluorine or chlorine. More particularly, $R^5$ is hydrogen or chlorine.

Preferably, $R^5$ is hydrogen.

In one embodiment, when A is Het or optionally substituted phenyl, then $R^1$ is hydrogen, chlorine, fluorine, bromine, $C_1$fluoroalkyl (e.g. —$CF_3$), cyano or $C_{1-3}$alkyl (e.g. methyl), and at least one of $R^1$, $R^2$ and $R^3$ is other than hydrogen.

In a particular embodiment,
$R^1$ is chlorine, fluorine or methyl;
$R^2$ is hydrogen, fluorine, chlorine, —$CF_3$ or methyl;
$R^3$ is hydrogen, fluorine or chlorine; and
$R^5$ is hydrogen, fluorine, chlorine or methyl;
wherein at least one of $R^2$ and $R^3$ is other than hydrogen; and wherein, when $R^5$ is fluorine, chlorine or methyl, then $R^2$ is hydrogen and $R^3$ is fluorine or chlorine.

In a more particular embodiment,
$R^1$ is chlorine, fluorine or methyl;
$R^2$ is hydrogen, fluorine, chlorine, —$CF_3$ or methyl;

$R^3$ is hydrogen, fluorine or chlorine; and
$R^5$ is hydrogen, fluorine or chlorine;
wherein at least one of $R^2$ and $R^3$ is other than hydrogen; and
wherein, when $R^5$ is fluorine or chlorine, then $R^2$ is hydrogen
and $R^3$ is fluorine or chlorine.

In a still more particular embodiment,
$R^1$ is chlorine;
$R^2$ is hydrogen, fluorine, chlorine, —$CF_3$ or methyl;
$R^3$ is hydrogen, fluorine or chlorine; and
$R^5$ is hydrogen, fluorine, or chlorine (preferably hydrogen);
wherein at least one of $R^2$ and $R^3$ is other than hydrogen; and
wherein, when $R^5$ is fluorine or chlorine, then $R^2$ is hydrogen
and $R^3$ is fluorine or chlorine.

Preferably,
$R^1$ is chlorine;
$R^2$ is hydrogen, fluorine, chlorine or —$CF_3$;
$R^3$ is hydrogen, fluorine or chlorine; and
$R^5$ is hydrogen;
wherein at least one of $R^2$ and $R^3$ is other than hydrogen,
and wherein, when $R^3$ is chlorine then $R^2$ is hydrogen or fluorine.

In a particular embodiment,
$R^1$ is chlorine, $R^2$ is —$CF_3$, and $R^3$, $R^4$ and $R^5$ are hydrogen; or
$R^1$ is chlorine, $R^2$ is chlorine, and $R^3$, $R^4$ and $R^5$ are hydrogen; or
$R^1$ is chlorine, $R^2$, $R^4$ and $R^5$ are hydrogen, and $R^3$ is chlorine; or
$R^1$ is chlorine, $R^2$, $R^4$ and $R^5$ are hydrogen, and $R^3$ is fluorine; or
$R^1$ is chlorine, $R^2$ is methyl, and $R^3$, $R^4$ and $R^5$ are hydrogen; or
$R^1$ is chlorine, $R^2$ and $R^4$ hydrogen, and $R^3$ and $R^5$ are chlorine; or
$R^1$ is chlorine, $R^2$ is chlorine, $R^3$ is fluorine, and $R^4$ and $R^5$ are hydrogen; or
$R^1$ is chlorine, $R^2$ is fluorine, $R^3$ is chlorine, and $R^4$ and $R^5$ are hydrogen; or
$R^1$ is chlorine, $R^2$ and $R^3$ are fluorine, and $R^4$ and $R^5$ are hydrogen; or
$R^1$ is chlorine, $R^2$ is —$CF_3$, $R^3$ is fluorine, and $R^4$ and $R^5$ are hydrogen; or
$R^1$ is fluorine, $R^2$ is —$CF_3$, and $R^3$, $R^4$ and $R^5$ are hydrogen; or
$R^1$ is fluorine, $R^2$ is chlorine, and $R^3$, $R^4$ and $R^5$ are hydrogen; or
$R^1$ is fluorine, $R^2$, $R^4$ and $R^5$ are hydrogen, and $R^3$ is chlorine; or
$R^1$ is methyl, $R^2$, $R^4$ and $R^5$ are hydrogen, and $R^3$ is fluorine; or
$R^1$ is methyl, $R^2$ is —$CF_3$, and $R^3$, $R^4$ and $R^5$ are hydrogen; or
$R^1$ is chlorine, $R^2$, $R^3$, $R^4$ and $R^5$ are hydrogen, and A is Het or optionally substituted phenyl; or
$R^1$ is hydrogen, $R^2$ is —$CF_3$, $R^3$ is fluorine, $R^4$ and $R^5$ are hydrogen, and A is Het or optionally substituted phenyl; or
$R^1$ is hydrogen, $R^2$ is —$CF_3$, $R^3$ is chlorine, $R^4$ and $R^5$ are hydrogen, and A is Het or optionally substituted phenyl; or
$R^1$ is hydrogen, $R^2$ is chlorine, $R^3$ is fluorine, $R^4$ and $R^5$ are hydrogen, and A is Het or optionally substituted phenyl.

Preferably,
$R^1$ is chlorine, $R^2$ is —$CF_3$, and $R^3$, $R^4$ and $R^5$ are hydrogen; or
$R^1$ is chlorine, $R^2$ is chlorine, and $R^3$, $R^4$ and $R^5$ are hydrogen; or
$R^1$ is chlorine, $R^2$, $R^4$ and $R^5$ are hydrogen, and $R^3$ is chlorine; or
$R^1$ is chlorine, $R^2$, $R^4$ and $R^5$ are hydrogen, and $R^3$ is fluorine.

Most preferably,
$R^1$ is chlorine, $R^2$ is —$CF_3$, and $R^3$, $R^4$ and $R^5$ are hydrogen; or
$R^1$ is chlorine, $R^2$, $R^4$ and $R^5$ are hydrogen, and $R^3$ is chlorine; or
$R^1$ is chlorine, $R^2$, $R^4$ and $R^5$ are hydrogen, and $R^3$ is fluorine.

In a particular embodiment, $R^6$ and $R^7$ independently are hydrogen or methyl;
or $R^6$ and $R^7$ are taken together and are —$(CH_2)_2$—O—$(CH_2)_2$— or —$(CH_2)_n{}^1$—, wherein $n^1$ is 3, 4, 5 or 6 (in particular 3, 4 or 5).

In a particular embodiment, $n^1$ is 3, 4 or 5.

In a particular embodiment, $R^{14}$ is hydrogen, $C_{1-4}$alkyl (e.g. methyl, ethyl or t-butyl), $C_{1-2}$fluoroalkyl (e.g. $C_1$fluoroalkyl, in particular —$CF_3$), halogen, or phenyl wherein the phenyl is optionally substituted by one substituent being fluorine, chlorine, methyl, —$CF_3$ or methoxy.

In a particular embodiment, $R^{14}$ is hydrogen, $C_{1-4}$alkyl (e.g. methyl, ethyl or t-butyl), $C_{1-2}$fluoroalkyl (e.g. $C_1$fluoroalkyl, in particular —$CF_3$), halogen (e.g. chlorine, bromine or iodine), or unsubstituted phenyl.

In one embodiment, $R^{14}$ is hydrogen, methyl, ethyl, t-butyl, —$CF_3$, chlorine, bromine or iodine, or unsubstituted phenyl.

In a more particular embodiment, $R^{14}$ is hydrogen, $C_{1-3}$alkyl (e.g. methyl or ethyl), $C_1$fluoroalkyl (e.g. —$CF_3$), or halogen (e.g. chlorine, bromine or iodine).

In a still more particular embodiment, $R^{14}$ is hydrogen, methyl, ethyl, —$CF_3$, chlorine, bromine or iodine.

Preferably, $R^{14}$ is hydrogen, —$CF_3$, chlorine, bromine or iodine. In one particular embodiment, $R^{14}$ is hydrogen, In one embodiment, when A is halogen (e.g. chlorine, bromine or iodine), optionally substituted phenyl or Het, then $R^{14}$ is hydrogen, —$CF_3$, chlorine, bromine or iodine.

In one embodiment, when $R^{14}$ is phenyl, or $C_{1-4}$alkyl, then A is hydrogen.

In one particular embodiment of the invention, there is provided a compound of formula (I) or a pharmaceutically acceptable salt thereof, which is:
a compound or salt, named in and/or whose formula is illustrated in any one of the Examples (e.g. any one of Examples 1 to 28 and 30 to 34 and/or Examples 29 and 35 to 45), as the compound or a pharmaceutically acceptable salt thereof (for example as the compound or a hydrochloride salt thereof).

Therefore, according to one particular aspect of the invention, there is provided a compound or a pharmaceutically acceptable salt thereof, which is:

7-{[2-chloro-3-(trifluoromethyl)phenyl]carbonyl}-5,6,7,8-tetrahydroimidazo[1,2-a]pyrazine,
7-{[2-chloro-3-(trifluoromethyl)phenyl]carbonyl}-2-(trifluoromethyl)-5,6,7,8-tetrahydroimidazo[1,2-a]pyrazine,
7-[(2,4-dichlorophenyl)carbonyl]-2-(trifluoromethyl)-5,6,7,8-tetrahydroimidazo[1,2-a]pyrazine,
7-{[2-chloro-3-(trifluoromethyl)phenyl]carbonyl}-3-phenyl-5,6,7,8-tetrahydroimidazo[1,2-a]pyrazine,
7-[(2,4-dichlorophenyl)carbonyl]-3-phenyl-5,6,7,8-tetrahydroimidazo[1,2-a]pyrazine,
7-{[2-chloro-3-(trifluoromethyl)phenyl]carbonyl}-2-ethyl-5,6,7,8-tetrahydroimidazo[1,2-a]pyrazine,
7-[(2,4-dichlorophenyl)carbonyl]-2-ethyl-5,6,7,8-tetrahydroimidazo[1,2-a]pyrazine,
7-[(2-chlorophenyl)carbonyl]-3-phenyl-5,6,7,8-tetrahydroimidazo[1,2-a]pyrazine,
7-[(2,3-dichlorophenyl)carbonyl]-3-phenyl-5,6,7,8-tetrahydroimidazo[1,2-a]pyrazine,
7-[(2-chloro-4-fluorophenyl)carbonyl]-3-phenyl-5,6,7,8-tetrahydroimidazo[1,2-a]pyrazine, 7-{[2-chloro-3-(trifluoromethyl)phenyl]carbonyl}-2-methyl-5,6,7,8-tetrahydroimidazo[1,2-a]pyrazine, 7-[(2,3-dichlorophenyl)carbonyl]-2-methyl-5,6,7,8-tetrahydroimidazo[1,2-a]pyrazine, 7-{[2-chloro-3-(trifluoromethyl)phenyl]carbonyl}-2-(1,1-dimethylethyl)-5,6,7,8-tetrahydroimidazo[1,2-a]pyrazine, 7-{[2-chloro-3-(trifluoromethyl)phenyl]carbonyl}-2-phenyl-5,6,7,8-tetrahydroimidazo[1,2-a]pyrazine, 7-[(2,3-dichlorophenyl)carbonyl]-2-phenyl-5,6,7,8-tetrahydroimidazo[1,2-a]pyrazine, 7-{[2-chloro-3-(trifluoromethyl)phenyl]carbonyl}-3-(2-pyridinyl)-5,6,7,8-tetrahydroimidazo[1,2-a]pyrazine, 3-phenyl-7-[(2,4,6-trichlorophenyl)carbonyl]-5,6,7,8-tetrahydroimidazo[1,2-a]pyrazine, 3-bromo-7-{[2-chloro-3-(trifluoromethyl)phenyl]carbonyl}-5,6,7,8-tetrahydroimidazo[1,2-a]pyrazine, 3-bromo-7-{[2-chloro-3-(trifluoromethyl)phenyl]carbonyl}-2-(trifluoromethyl)-5,6,7,8-tetrahydroimidazo[1,2-a]pyrazine, 7-{[2-chloro-3-(trifluoromethyl)phenyl]carbonyl}-2,3-diiodo-5,6,7,8-tetrahydroimidazo[1,2-a]pyrazine, 7-{[2-chloro-3-(trifluoromethyl)phenyl]carbonyl}-3-iodo-5,6,7,8-tetrahydroimidazo[1,2-a]pyrazine, 7-{[2-chloro-3-(trifluoromethyl)phenyl]carbonyl}-3-(4-fluorophenyl)-5,6,7,8-tetrahydroimidazo[1,2-a]pyrazine, 7-{[2-chloro-3-(trifluoromethyl)phenyl]carbonyl}-3-(3-pyridinyl)-5,6,7,8-tetrahydroimidazo[1,2-a]pyrazine, 3-[2-chloro-3-(trifluoromethyl)phenyl]-7-{[2-chloro-3-(trifluoromethyl)phenyl]carbonyl}-5,6,7,8-tetrahydroimidazo[1,2-a]pyrazine, 3-(4-chlorophenyl)-7-{[2-chloro-3-(trifluoromethyl)phenyl]carbonyl}-5,6,7,8-tetrahydroimidazo[1,2-a]pyrazine, 7-{[2-chloro-3-(trifluoromethyl)phenyl]carbonyl}-3-phenyl-2-(trifluoromethyl)-5,6,7,8-tetrahydroimidazo[1,2-a]pyrazine, 7-{[2-chloro-3-(trifluoromethyl)phenyl]carbonyl}-3-methyl-5,6,7,8-tetrahydroimidazo[1,2-a]pyrazine, 7-{[2-chloro-3-(trifluoromethyl)phenyl]carbonyl}-3-(2-methylphenyl)-5,6,7,8-tetrahydroimidazo[1,2-a]pyrazine, 3-bromo-7-[(2-chloro-4-fluorophenyl)carbonyl]-5,6,7,8-tetrahydroimidazo[1,2-a]pyrazine, 7-{[2-chloro-3-(trifluoromethyl)phenyl]carbonyl}-3-(5-fluoro-2-pyridinyl)-5,6,7,8-tetrahydroimidazo[1,2-a]pyrazine, 3-bromo-7-[(2-chloro-4-fluorophenyl)carbonyl]-2-(trifluoromethyl)-5,6,7,8-tetrahydroimidazo[1,2-a]pyrazine, 3-bromo-2-chloro-7-{[2-chloro-3-(trifluoromethyl)phenyl]carbonyl}-5,6,7,8-tetrahydroimidazo[1,2-a]pyrazine, or 2-bromo-7-{[2-chloro-3-(trifluoromethyl)phenyl]carbonyl}-3-(4-fluorophenyl)-5,6,7,8-tetrahydroimidazo[1,2-a]pyrazine;

or a pharmaceutically acceptable salt thereof.

In a further particular aspect of the invention, there is provided a compound or a pharmaceutically acceptable salt thereof, which is:

E29 2,3-dichloro-7-[(2,4-dichlorophenyl)carbonyl]-5,6,7,8-tetrahydroimidazo[1,2-a]pyrazine, E35 7-{[2-chloro-3-(trifluoromethyl)phenyl]carbonyl}-3-(4-fluorophenyl)-2-(trifluoromethyl)-5,6,7,8-tetrahydroimidazo[1,2-a]pyrazine, E36 7-[(2,4-dichlorophenyl)carbonyl]-3-(4-fluorophenyl)-2-(trifluoromethyl)-5,6,7,8-tetrahydroimidazo[1,2-a]pyrazine, E37 7-[(2-chloro-4-fluorophenyl)carbonyl]-3-(2-pyrazinyl)-5,6,7,8-tetrahydroimidazo[1,2-a]pyrazine, E38 7-{[2-chloro-3-(trifluoromethyl)phenyl]carbonyl}-3-(2-pyrazinyl)-5,6,7,8-tetrahydroimidazo[1,2-a]pyrazine, E39 7-{[2-chloro-3-(trifluoromethyl)phenyl]carbonyl}-3-(1,3-thiazol-2-yl)-5,6,7,8-tetrahydroimidazo[1,2-a]pyrazine, E40 7-[(2-chloro-4-fluorophenyl)carbonyl]-3-(2-pyrazinyl)-5,6,7,8-tetrahydroimidazo[1,2-a]pyrazine, E41 7-{[2-chloro-3-(trifluoromethyl)phenyl]carbonyl}-3-(2-pyrimidinyl)-5,6,7,8-tetrahydroimidazo[1,2-a]pyrazine, E42 7-{[2-chloro-3-(trifluoromethyl)phenyl]carbonyl}-3-(1,3-thiazol-4-yl)-5,6,7,8-tetrahydroimidazo[1,2-a]pyrazine, E43 3-chloro-7-{[2-chloro-3-(trifluoromethyl)phenyl]carbonyl}-5,6,7,8-tetrahydroimidazo[1,2-a]pyrazine, E44 3-chloro-7-[(2,4-dichlorophenyl)carbonyl]-5,6,7,8-tetrahydroimidazo[1,2-a]pyrazine, or E45 2,3-dichloro-7-{[2-chloro-3-(trifluoromethyl)phenyl]carbonyl}-5,6,7,8-tetrahydroimidazo[1,2-a]pyrazine;

or a pharmaceutically acceptable salt thereof.

In the above-mentioned particular aspect, the invention can for example be a compound or a hydrochloride salt thereof.

According to a preferred aspect of the invention, there is provided a compound or a pharmaceutically acceptable salt thereof, which is:

3-bromo-7-{[2-chloro-3-(trifluoromethyl)phenyl]carbonyl}-2-(trifluoromethyl)-5,6,7,8-tetrahydroimidazo[1,2-a]pyrazine (e.g. see Example 19);

or a pharmaceutically acceptable salt (e.g. hydrochloride salt) thereof.

Antagonists of P2X7 may be useful in the treatment (e.g. amelioration) or prophylaxis (in particular treatment) of a variety of pain states (e.g. neuropathic pain, chronic inflammatory pain, or visceral pain), inflammation (e.g. rheumatoid arthritis or osteoarthritis), or neurodegenerative diseases, in particular Alzheimer's disease. P2X7 antagonists may constitute useful therapeutic agents in the management of rheumatoid arthritis and inflammatory bowel disease.

Compounds or salts of the present invention which modulate P2X7 receptor function and are capable of antagonizing the effects of ATP at the P2X7 receptor ("P2X7 receptor antagonists") may be competitive antagonists, inverse agonists, or negative allosteric modulators of P2X7 receptor function.

Certain compounds of formula (I) may in some circumstances form acid addition salts thereof. It will be appreciated that for use in medicine compounds of formula (I) may be used as salts, in which case the salts should be pharmaceutically acceptable. Pharmaceutically acceptable salts include those described by Berge, Bighley and Monkhouse, *J. Pharm. Sci.*, 1977, 66, 1-19.

When a compound of formula (I) is basic, in one embodiment a pharmaceutically acceptable salt is formed from a pharmaceutically acceptable acid such as an inorganic or organic acid. Such acids include acetic, p-aminobenzoic, ascorbic, aspartic, benzenesulfonic, benzoic, bismethylene-salicylic, camphorsulfonic, citric, cyclohexylsulfamic, ethanedisulfonic, ethanesulfonic, fumaric, gluconic, glutamic, glycolic, hydrobromic, hydrochloric, isethionic, itaconic, lactic, maleic, malic, mandelic, methanesulfonic, mucic, nitric, palmitic, pamoic, pantothenic, phosphoric, propionic, salicylic, stearic, succinic, sulfuric, tartaric, p-toluenesulfonic acid, and the like.

In one particular embodiment, the pharmaceutically acceptable salt is formed from a pharmaceutically acceptable strong acid. For example, the pharmaceutically acceptable salt can be a benzenesulfonate, camphorsulfonate, ethanesulfonate, hydrobromide, hydrochloride, methanesulfonate, nitrate, phosphate, sulfate, or p-toluenesulfonate.

The compounds of formula (I) or pharmaceutically acceptable salts thereof may be prepared in crystalline or non-crystalline form (e.g. in crystalline or amorphous solid form), and, in particular if crystalline, may optionally be solvated, e.g. as the hydrate. This invention includes within its scope solvates (e.g. hydrates) of compounds of formula (I) or pharmaceutically acceptable salts thereof, for example stoichiometric solvates (e.g. hydrates); as well as compounds or salts thereof containing variable amounts of solvent (e.g. water).

Certain compounds of formula (I) or salts thereof may be capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Preparation of Compounds

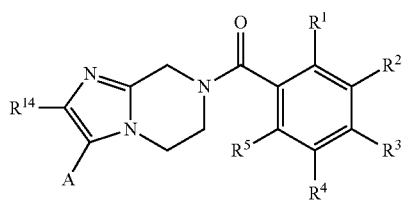

(I)

Compounds of formula (I), wherein the variables are as defined herein, and pharmaceutically acceptable salts thereof may be prepared by the methodology described hereinafter, constituting a further aspect of this invention.

A further aspect of the present invention provides a process for preparing a compound of formula (I) or a pharmaceutically acceptable salt thereof comprising step (a), (b), (c), (d) or (e) as described below;
and optionally preparing a pharmaceutically acceptable salt of the compound.

(a) Preparation of a compound of formula (I) by coupling of a compound of formula (2) with a compound of formula (3) which is an acid chloride (Y=Cl) or a carboxylic acid (Y=OH) or an activated derivative of the carboxylic acid (see Scheme 1 below),
wherein $R^1$, $R^2$, $R^3$, $R^4$, $R^5$, $R^{14}$, and A are as defined herein. Compounds (2) and (3) are optionally protected.

(b) Preparation of a compound of formula (I) by reacting a compound of formula (4) (where X=H, or a halogen such as bromine, iodine or chlorine), with a compound of formula (5), wherein L represents a suitable leaving group such as a halogen atom (e.g. bromine or iodine) or a boronic acid or ester (see Scheme 2 below), and wherein $R^1$, $R^2$, $R^3$, $R^4$, $R^5$, $R^{14}$, and A are as defined herein. Compounds (4) and (5) are optionally protected.

(c) Preparation of compound of formula (I) by reacting a compound of formula (9) with a compound of formula (10) (see Scheme 4 below) wherein $R^1$, $R^2$, $R^3$, $R^4$, $R^5$, $R^{14}$, and A are as defined herein and $R^{15}$ is $C_{1-4}$alkyl such as ethyl or methyl. Compounds (9) and (10) are optionally protected.

(d) Deprotecting a compound of formula (I) which is protected. Examples of protecting groups and the means for their removal can be found in T. W. Greene and P. G. M. Wuts 'Protective Groups in Organic Synthesis' (Wiley-Interscience, 4th ed., 2006).

(e) Interconversion of compounds of formula (I) to other compounds of formula (I). Examples of interconversion procedures include epimerisation, oxidation, reduction, alkylation, aromatic substitution, nucleophilic substitution, amide coupling and ester hydrolysis.

Representative methods for the preparation of compounds of formula (1) are shown in Schemes 1 to 3 below:

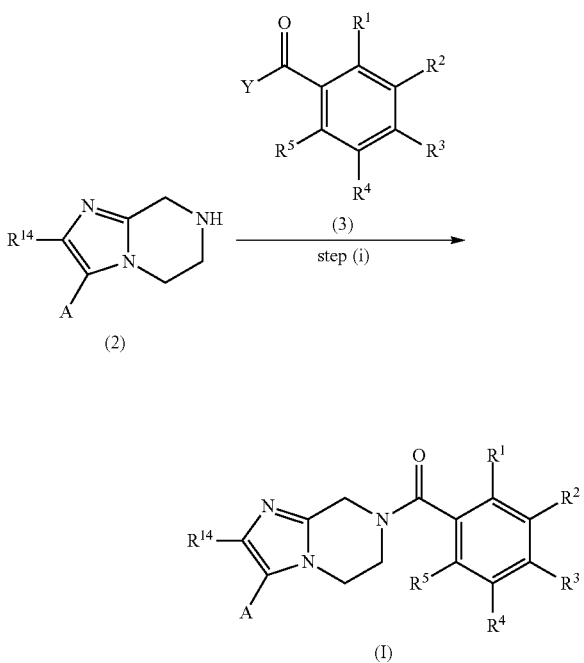

Step (i) in Scheme 1 typically comprises treatment of a compound of formula (2) (or an acid addition salt thereof, see e.g. Scheme 4 for general preparative routes) with an acid chloride of formula (3) (Y=Cl) in the presence of a suitable base such as triethylamine or diethylaminomethyl polystyrene, in a suitable solvent such as N,N-dimethylformamide or dichloromethane, and e.g. at a suitable temperature such as from about 0° C. to room temperature.

Alternatively, a compound of formula (2) could be treated with a carboxylic acid of formula (3) (where Y=OH) in the presence of an activating agent, such as water soluble carbodiimide and a suitable base such as diisopropylethylamine, in a suitable solvent such as dichloromethane, and for example at a suitable temperature e.g. from about 0° C. to room temperature.

Scheme 2

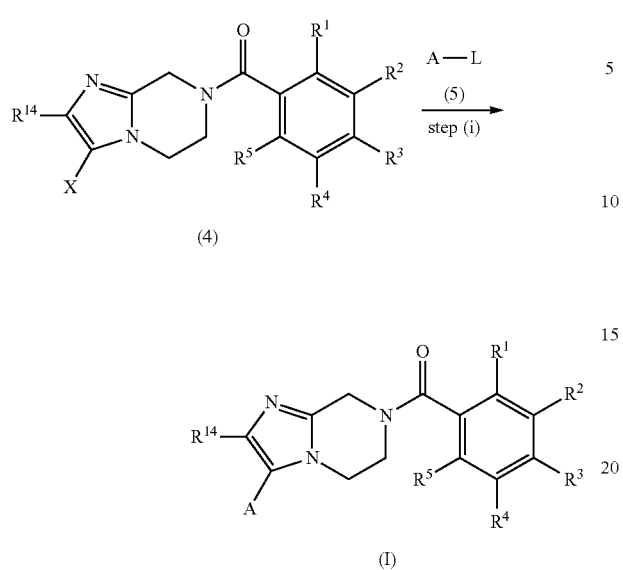

Step (i) in Scheme 2 typically comprises reacting a compound of formula (4) (where X=H or a halogen e.g. bromine, iodine or chlorine, in particular bromine), which can be prepared as described above in Scheme 1, with a compound of formula (5), wherein L represents a suitable leaving group such as a halogen atom (e.g. bromine or iodine) or a boronic acid or ester, in the presence of a suitable catalyst such as (a) palladium(II) acetate and triphenylphosphine or (b) palladium(II) acetate and 1,1'-(bisdiphenylphosphino)ferrocene or (c) dichlorobis(triphenylphosphine)palladium(II), and in the presence of a suitable base such as cesium carbonate or sodium carbonate, in a suitable solvent such as 1,4-dioxane, N,N-dimethylformamide or 1,2-dimethoxyethane, and for example at a suitable temperature e.g. from room temperature to reflux temperature. In certain embodiments (e.g. see Example 31), step (i) is also carried in the presence of a copper(I) salt such as copper(I) iodide or copper(I) chloride.

Scheme 3

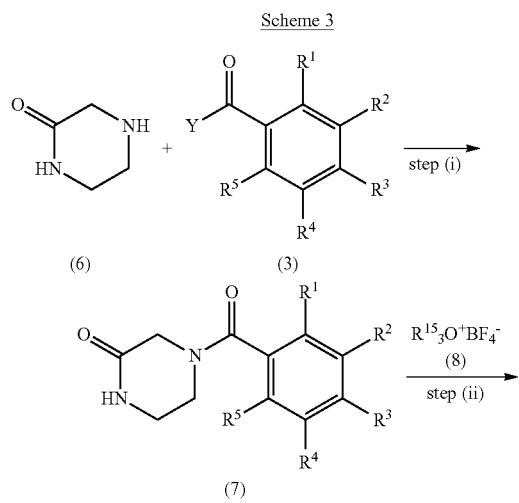

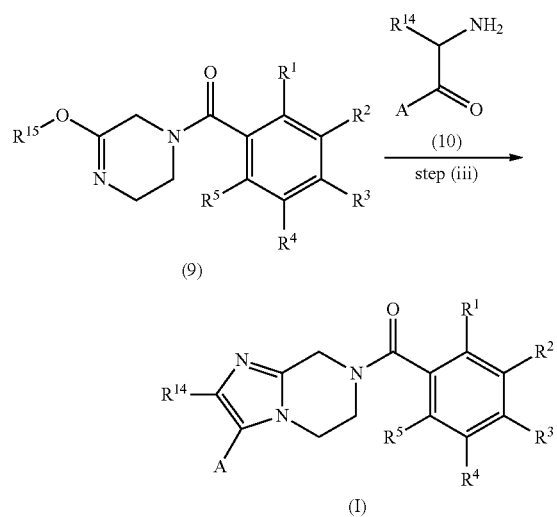

Step (i) in Scheme 3 typically comprises treatment of compound (6) with compound (3) in a manner analogous to that described in step (i) of Scheme 1.

Step (ii) in Scheme 3 typically comprises treatment of compound (7) with a $triC_{1-4}$alkyloxonium tetrafluoroborate (e.g. triethyloxonium tetrafluoroborate) reagent (8), in a suitable solvent such as dichloromethane, and e.g. at a suitable temperature such as room temperature.

Step (iii) in Scheme 3 typically comprises treatment of compound (9) with a suitable alpha-amino ketone (10) in a suitable solvent such as 1-butanol, e.g. at a suitable temperature such as reflux temperature.

Steps (ii) and (iii) in Scheme 3 can also be combined in a single step which results in the conversion of compound (7) to compounds of formula (I) without the intermediate isolation of compounds of formula (9).

Compounds of formulae (2), (3), (5), (6), (8) and (10) are typically either available from commercial sources and/or can be prepared by a person skilled in the art using methods described in the chemical literature (or using analogous methods).

Compounds of formulae (2) can be prepared using the representative methods outlined in Schemes 4 and 5 below:

Scheme 4

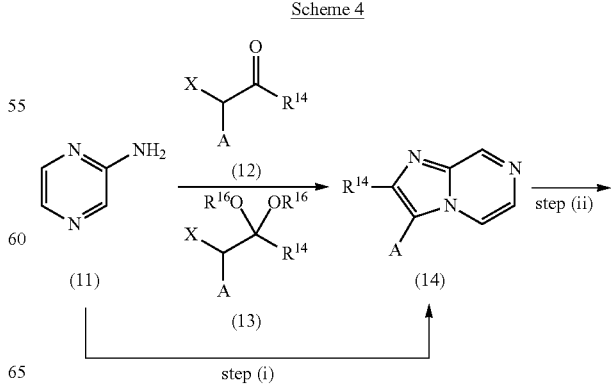

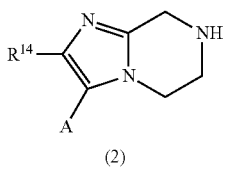

(2)

Step (i) in Scheme 4 typically comprises treatment of compound (11) with a compound of formula (12) or (13) (wherein $R^{16}$ represents a lower alkyl group) in a suitable solvent such ethanol, e.g. at a suitable temperature such as reflux temperature and, in the cases where compounds of formula (13) are used, with the addition of a suitable acid, such as hydrobromic acid.

Step (ii) typically comprises hydrogenation of compounds of formula (14) in the presence of a suitable catalyst, such as 10% palladium on carbon or platinum (IV) oxide, at a suitable pressure such as from 14.7 p.s.i. (atmospheric pressure) and 50 p.s.i., in a suitable solvent such as methanol or ethanol, and e.g. at a suitable temperature such as from room temperature to 50° C.

such as a halogen atom (e.g. bromine or iodine), in the presence of a suitable catalyst such as palladium(II)acetate and triphenylphosphine, and potassium acetate, in a suitable solvent such as N,N-dimethylacetamide, and e.g. at a suitable temperature e.g. from room temperature to 150° C., in a microwave reactor.

Scheme 6

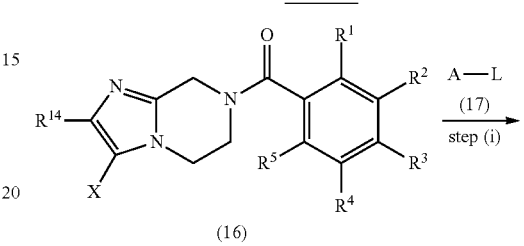

(16)

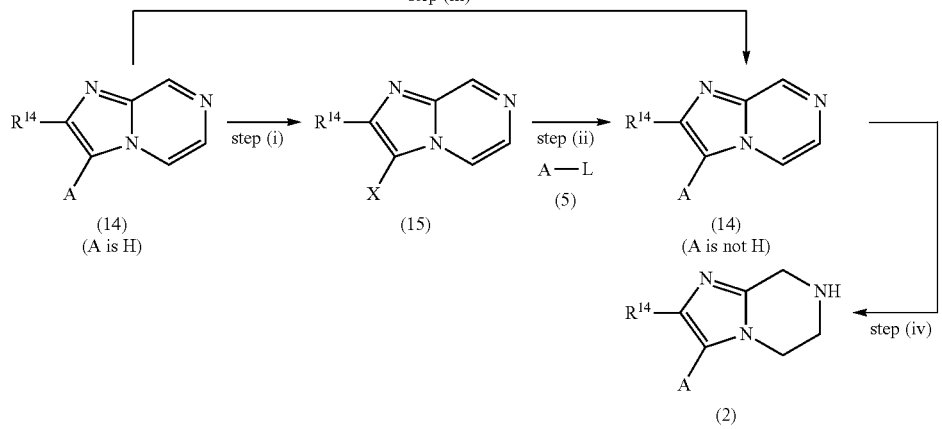

Step (i) in Scheme 5 typically comprises treatment of compounds of formula (14) (which can be prepared as outlined in Scheme 4) where A=H, with a halogenating agent (e.g. brominating agent), such as a mixture of bromine, potassium bromide, and sodium acetate, in a suitable solvent such as methanol, and e.g. at a suitable temperature such as from −15° C. to room temperature, to give compounds of formula (15) where X is a halogen (e.g. bromine).

Step (ii) in Scheme 5 typically comprises reacting a compound of formula (15) (where X=a halogen e.g. bromine) with a compound of formula (5), wherein L represents a suitable leaving group such as a boronic acid or ester, in the presence of a suitable catalyst such as dichlorobis(triphenylphosphine)palladium(II), and a suitable base such as sodium carbonate, in a suitable solvent such as 1,2-dimethoxyethane and water, and e.g. at a suitable temperature e.g. from room temperature to reflux temperature.

Step (iii) in Scheme 5 typically comprises reacting a compound of formula (14) (where A=H), with a compound of formula (5), wherein L represents a suitable leaving group -continued

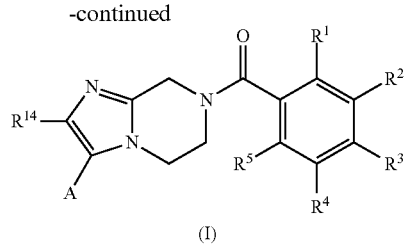

(I)

Step (i) in Scheme 6 typically comprises reacting a compound of formula (16) (where X═H or a halogen e.g. bromine, iodine or chlorine, in particular bromine), which can be prepared as described above in Scheme 5 step (i), with a compound of formula (17), wherein L represents a suitable leaving group such as a halogen atom (e.g. bromine or iodine) or tin reagent, in the presence of a suitable catalyst such as (a) palladium tetrakis, and in the presence of a suitable solvent such as 1,4-dioxane, and for example at a suitable temperature e.g. from room temperature to reflux temperature, using conventional heating or using microwave conditions.

Scheme 7

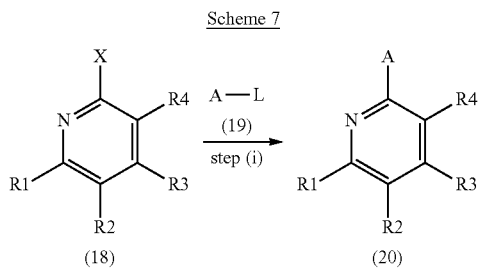

Step (i) in scheme 7 typically comprises of reacting a compound of formula (18) (where X=H, or a halogen e.g. bromine, iodine or chlorine, in particular bromine, and R1-R4=H or a halogen e.g. fluorine), which are commercially available, with a compound of formula (19), wherein L represents a suitable leaving group such as halogen atom (e.g. bromine or iodine) or tin reagent, in the presence of a suitable catalyst such as (a) palladium tetrakis, and in the presence of a suitable solvent such as 1,4-dioxane, and for example at a suitable temperature e.g. from room temperature to reflux temperature, using conventional heating or microwave conditions.

Compound (11) and compounds of formulae (5), (12), and (13) are typically either available from commercial sources and/or can be prepared by a person skilled in the art using methods described in the chemical literature (or using analogous methods). Where relevant, pharmaceutically acceptable salts may be prepared conventionally by reaction with the appropriate acid or acid derivative.

Clinical Indications, Pharmaceutical Compositions, and Dosages

It is believed that, as the compounds or pharmaceutically acceptable salts of the present invention modulate P2X7 receptor function and are capable of antagonizing the effects of ATP at the P2X7 receptor ("P2X7 receptor antagonists"); they may be useful in the treatment or prophylaxis (in particular treatment) of pain; such as acute pain, chronic pain, chronic articular pain, musculoskeletal pain, neuropathic pain, inflammatory pain, visceral pain, pain associated with cancer, pain associated with migraine, tension headache or cluster headaches, pain associated with functional bowel disorders, lower back and/or neck pain, pain associated with sprains and/or strains, sympathetically maintained pain; myositis, pain associated with influenza or other viral infections such as the common cold, pain associated with rheumatic fever, pain associated with myocardial ischemia, post operative pain, cancer chemotherapy, headache, toothache, or dysmenorrhea.

The chronic articular pain condition can be rheumatoid arthritis, osteoarthritis, rheumatoid spondylitis (ankylosing spondylitis), gouty arthritis or juvenile arthritis.

The inflammatory pain condition can be rheumatoid arthritis, osteoarthritis, rheumatoid spondylitis (ankylosing spondylitis) or fibromyalgia.

In particular, the compounds of formula (I) or pharmaceutically acceptable salts thereof may be useful in the treatment or prophylaxis (in particular treatment) of pain (e.g. inflammatory pain) in arthritis, such as pain (e.g. inflammatory pain) in rheumatoid arthritis or osteoarthritis.

Pain associated with functional bowel disorders includes non-ulcer dyspepsia, non-cardiac chest pain and irritable bowel syndrome.

The neuropathic pain condition can be: diabetic neuropathy (e.g. painful diabetic neuropathy), sciatica, non-specific lower back pain, trigeminal neuralgia, multiple sclerosis pain, fibromyalgia, HIV-related neuropathy, post-herpetic neuralgia, trigeminal neuralgia, or lumbar radiculopathy; or pain resulting from physical trauma, amputation, phantom limb syndrome, spinal surgery, cancer, toxins or chronic inflammatory conditions. Alternatively, the neuropathic pain condition can be pain associated with normally non-painful sensations such as "pins and needles" (paraesthesias and/or dysesthesias), increased sensitivity to touch (hyperesthesia), painful sensation following innocuous stimulation (dynamic, static, thermal or cold allodynia), increased sensitivity to noxious stimuli (thermal, cold, or mechanical hyperalgesia), continuing pain sensation after removal of the stimulation (hyperpathia), or an absence of or deficit in selective sensory pathways (hypoalgesia).

The acute pain condition can be post-surgical pain or dysmenorrhea (e.g. primary dysmenorrhea).

The compounds or pharmaceutically acceptable salts of the present invention may potentially be useful in the treatment or prophylaxis (e.g. prophylaxis, e.g. reduction, delay or prevention) of the development of tolerence to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol).

Other conditions which could potentially be subject to treatment or prophylaxis (in particular treatment) using the compounds or salts of the present invention are: fever, inflammation, immunological diseases, abnormal platelet function diseases (e.g. occlusive vascular diseases), impotence or erectile dysfunction; bone disease characterised by abnormal bone metabolism or resorbtion; hemodynamic side effects of non-steroidal anti-inflammatory drugs (NSAID's) such as cyclooxygenase-2 (COX-2) inhibitors, cardiovascular diseases (e.g. atherosclerosis); neurodegenerative diseases and/or neurodegeneration; neurodegeneration following trauma; tinnitus; dependence on (e.g. addiction to) a dependence-inducing agent such as: an opioid analgesic (e.g. morphine), a CNS (central nervous system) depressant (e.g. ethanol), a psychostimulant (e.g. cocaine) or nicotine; diabetes such as Type 1 or Type 2 diabetes, complications of diabetes such as complications of Type I or Type 2 diabetes, kidney dysfunction, liver dysfunction (e.g. hepatitis, cirrhosis), gastrointestinal dysfunction (e.g. diarrhoea), gastric cancer, colon cancer, overactive bladder, or urge incontinence. Depression and alcoholism could potentially also be subject to treatment or prophylaxis by compounds or salts of the present invention. Inflammation and/or the inflammatory conditions associated with said inflammation can be: arthritis (in particular rheumatoid arthritis or osteoarthritis), skin conditions (e.g. sunburn, burns, eczema, dermatitis, allergic dermatitis, or psoriasis), meningitis, ophthalmic diseases such as glaucoma, retinitis, retinopathies, uveitis or of acute injury to the eye tissue (e.g. conjunctivitis), an inflammatory lung disorder (e.g. asthma, chronic obstructive pulmonary disease (COPD, which includes bronchitis and/or emphysema), allergic rhinitis, respiratory distress syndrome, pigeon fancier's disease, farmer's lung, or airways hyperresponsiveness); a gastrointestinal tract disorder (e.g. aphthous ulcer, Crohn's disease, atopic gastritis, gastritis varialoforme, ulcerative colitis, coeliac disease, regional ileitis, irritable bowel syndrome, inflammatory bowel disease, or gastrointestinal reflux disease); organ transplantation; or other conditions with an inflammatory component such as: vascular disease, migraine, periarteritis nodosa, thyroiditis, aplastic anaemia, Hodgkin's disease, sclerodoma, myaesthenia gravis, multiple sclerosis, sorcoidosis, nephrotic syndrome, Bechet's syndrome, gingivitis, myocardial ischemia, pyrexia, systemic lupus erythematosus, polymyositis, tendinitis, bursitis, or Sjogren's syndrome.

The inflammation and/or an inflammatory condition associated with said inflammation can in particular be arthritis (e.g. rheumatoid arthritis or osteoarthritis).

Immunological diseases include autoimmune diseases, immunological deficiency diseases or organ transplantation.

Bone diseases characterised by abnormal bone metabolism or resorbtion can be: osteoporosis (especially postmenopausal osteoporosis), hyper-calcemia, hyperparathyroidism, Paget's bone diseases, osteolysis, hypercalcemia of malignancy with or without bone metastases, rheumatoid arthritis, periodontitis, osteoarthritis, ostealgia, osteopenia, cancer cacchexia, calculosis, lithiasis (especially urolithiasis), solid carcinoma, gouty and/or ankylosing spondylitis, tendinitis or bursitis.

Cardiovascular diseases include hypertension or myocardiac ischemia; atherosclerosis; functional or organic venous insufficiency; varicose therapy; haemorrhoids; and shock states associated with a marked drop in arterial pressure (e.g. septic shock).

Neurodegenerative diseases which could potentially be subject to treatment or prophylaxis (in particular treatment) using the compounds or salts of the present invention are: dementia, particularly degenerative dementia (such as Alzheimer's disease, senile dementia, dementia with Lewy bodies, temporal lobe dementia, Huntingdon's chorea, Parkinson's disease, Pick's disease, Creutzfeldt-Jakob disease, or Amyotrophic Lateral Sclerosis (ALS); in particular Alzheimer's disease); mild cognitive impairment (MCI) e.g. MCI associated with ageing, particularly age associated memory impairment; motor neuron disease; vascular dementia (including multi-infarct dementia and/or dementia associated with cerebral ischaemia); or a neurodegenerative disease (e.g. dementia) associated with: an intracranial space occupying lesion, head trauma, intracranial and/or cerebral infections or related conditions (such as HIV infection, viral or bacterial meningitis, or cerebral herpes virus infections such as shingles or herpes simplex virus), metabolism, toxins, anoxia, hypoxia or vitamin deficiency.

The neurodegenerative disease, e.g. to be subject to treatment or prophylaxis (in particular treatment) by the compound of formula (I) or salt thereof, can in particular be degenerative dementia (in particular Alzheimer's disease), Parkinson's disease (in particular dementia in Parkinson's disease), vascular dementia (in particular multi-infarct dementia), dementia with Lewy bodies, Huntingdon's chorea, or mild cognitive impairment (MCI) e.g. MCI associated with ageing such as age associated memory impairment. The neurodegenerative disease, e.g. to be subject to treatment or prophylaxis (in particular treatment) by the compound of formula (I) or salt thereof, can in particular be degenerative dementia (in particular Alzheimer's disease), vascular dementia (in particular multi-infarct dementia), or mild cognitive impairment (MCI) e.g. MCI associated with ageing such as age associated memory impairment.

In one embodiment, the compound of formula (I) or the salt thereof of the invention is used for treatment or prophylaxis (in particular treatment) of a neurodegenerative disease (such as degenerative dementia e.g. Alzheimer's disease, or vascular dementia, or mild cognitive impairment), by disease modification and/or by neuroprotection. Alternatively or additionally, in one embodiment, the compound of formula (I) or the salt thereof of the invention is used for treatment or prophylaxis (in particular treatment) of a neurodegenerative disease (such as degenerative dementia e.g. Alzheimer's disease, or vascular dementia, or mild cognitive impairment) by symptomatic treatment of cognitive impairment associated with the neurodegenerative disease.

The compounds of formula (I) or pharmaceutically acceptable salts thereof may also be useful for neuroprotection and/or in the treatment or prophylaxis (e.g. treatment) of neurodegeneration following trauma such as stroke, cardiac arrest, pulmonary bypass, traumatic brain injury, spinal cord injury or the like.

The compounds or pharmaceutically acceptable salts of the present invention may also be useful in the treatment or prophylaxis (in particular treatment) of malignant cell growth and/or metastasis, or myoblastic leukaemia.

Complications of Type 1 diabetes can be: diabetic microangiopathy, diabetic retinopathy, diabetic nephropathy, macular degeneration, glaucoma, nephrotic syndrome, aplastic anaemia, uveitis, Kawasaki disease or sarcoidosis.

Kidney dysfunction can be: nephritis, glomerulonephritis, particularly mesangial proliferative glomerulonephritis or nephritic syndrome.

The compounds or pharmaceutically acceptable salts of the present invention may potentially be useful in the treatment or prophylaxis (e.g. treatment) of epilepsy and/or seizures (i.e. as anticonvulsants), for example in a mammal such as a human.

The compounds or pharmaceutically acceptable salts of the present invention may potentially be useful in the treatment or prophylaxis (e.g. treatment) of a human epileptic syndrome, such as: partial and/or generalised seizures (e.g. tonic, tonic-clonic, or absence seizures), temporal lobe epilepsy, absence epilepsies (including childhood, juvenile, myoclonic, photo- or pattern-induced), severe epileptic encephalopathies (including hypoxia-related or Rasmussen's syndrome), febrile convulsions, epilepsy partialis continua, progressive myoclonus epilepsies (including Unverricht-Lundborg disease or Lafora's disease), post-traumatic seizures and/or epilepsy such as those related to head injury, simple reflex epilepsies (including photosensive, somatosensory, proprioceptive, audiogenic or vestibular), metabolic disorders commonly associated with epilepsy such as pyridoxine-dependent epilepsy, Menkes' kinky hair disease, Krabbe's disease, epilepsy due to alcohol and/or drug abuse (e.g. cocaine abuse), cortical malformations associated with epilepsy (e.g. double cortex syndrome or subcortical band heterotopia), or chromosomal anomalies associated with seizures or epilepsy such as Partial monosomy (15Q/Angelman syndrome); in a human.

According to a further aspect of the invention, we therefore provide a compound of formula (I) or a pharmaceutically acceptable salt thereof for use in human or veterinary medicine and/or for use in therapy.

According to another aspect of the invention, we provide a compound of formula (I) or a pharmaceutically acceptable salt thereof for use in the treatment or prophylaxis (e.g. treatment) of a condition which is mediated by P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain, or rheumatoid arthritis or osteoarthritis); e.g. in a mammal such as a human or rodent e.g. human or rat e.g. human.

According to a further aspect of the invention, we provide a method of treatment or prophylaxis (e.g. treatment) of a human or animal (e.g. rodent e.g. rat) subject, for example a human subject, suffering from a condition which is mediated by P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain, or rheumatoid arthritis or osteoarthritis), which comprises administering to said subject an effective amount of a compound of formula (I) or a pharmaceutically acceptable salt thereof.

According to a further aspect of the invention we provide a method of treatment or prophylaxis (e.g. treatment) of a human or animal (e.g. rodent e.g. rat) subject, for example a human subject, suffering from or susceptible to pain, inflammation (e.g. rheumatoid arthritis or osteoarthritis), or a neurodegenerative disease (e.g. Alzheimer's disease or mild cognitive impairment), or epilepsy and/or seizures (e.g. a human epileptic syndrome), (more particularly pain such as inflammatory pain, neuropathic pain or visceral pain, or rheumatoid arthritis or osteoarthritis), which method comprises administering to said subject an effective amount of a compound of formula (I) or a pharmaceutically acceptable salt thereof.

According to a yet further aspect of the invention we provide a method of treatment or prophylaxis (e.g. treatment) of a human or animal (e.g. rodent e.g. rat) subject, for example a human subject, suffering from or susceptible to inflammatory pain, neuropathic pain or visceral pain (e.g. pain, such as inflammatory pain, in arthritis (e.g. rheumatoid arthritis or osteoarthritis)) which method comprises administering to said subject an effective amount of a compound of formula (I) or a pharmaceutically acceptable salt thereof.

According to a further aspect of the invention we provide a method of treatment of a subject, for example a human subject, suffering from Alzheimer's disease or mild cognitive impairment, which method comprises administering to said subject an effective amount of a compound of formula (I) or a pharmaceutically acceptable salt thereof.

In one aspect of the invention we provide a method of treatment or prophylaxis (e.g. prophylaxis, e.g. reduction, delay or prevention) of the development of tolerance to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol), in a subject suffering from or susceptible to the development of such opioid analgesic tolerance, which method comprises administering to said subject an effective amount of a compound of formula (I) or a pharmaceutically acceptable salt thereof.

For the avoidance of doubt, the term "treatment" as used herein when referring to a particular disease or condition, encompasses the alleviation of the symptoms associated with said disease or condition.

According to another aspect of the invention, we provide the use of a compound of formula (I) or a pharmaceutically acceptable salt thereof for the manufacture of a medicament for the treatment or prophylaxis (e.g. treatment) of a condition which is mediated by the action of P2X7 receptors, for example a condition or disease disclosed herein (in particular pain, inflammation such as rheumatoid arthritis or osteoarthritis, or a neurodegenerative disease (e.g. Alzheimer's disease or mild cognitive impairment), or epilepsy and/or seizures (e.g. a human epileptic syndrome); more particularly pain such as inflammatory pain, neuropathic pain or visceral pain); e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prophylaxis (e.g. treatment) of pain (e.g. inflammatory pain, neuropathic pain or visceral pain), inflammation (e.g. rheumatoid arthritis or osteoarthritis), or a neurodegenerative disease (e.g. Alzheimer's disease or mild cognitive impairment), or epilepsy and/or seizures (e.g. a human epileptic syndrome), (more particularly: pain such as inflammatory pain, neuropathic pain or visceral pain, or rheumatoid arthritis or osteoarthritis); e.g. in a mammal such as a human or rodent e.g. human or rat e.g. human.

According to another aspect of the invention we provide the use of a compound of formula (I) or a pharmaceutically acceptable salt thereof for the manufacture of a medicament for the treatment or prophylaxis (e.g. treatment) of inflammatory pain, neuropathic pain or visceral pain (in particular inflammatory pain or neuropathic pain; such as inflammatory pain in arthritis such as rheumatoid arthritis or osteoarthritis); e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prophylaxis (e.g. treatment) of Alzheimer's disease or mild cognitive impairment; e.g. in a mammal such as a human or rodent e.g. human or rat e.g. human.

In one aspect of the invention we provide the use of a compound of formula (I) or a pharmaceutically acceptable salt thereof for the manufacture of a medicament for the treatment or prophylaxis (e.g. prophylaxis, e.g. reduction, delay or prevention) of the development of tolerance to the analgesic action of an opioid analgesic (such as morphine, fentanyl, oxycodone, tramadol, hydrocodone, hydromorphone, oxymorphone, methadone or buprenorphine; in particular morphine, fentanyl, oxycodone, or tramadol).

In order to use a compound of formula (I) or a pharmaceutically acceptable salt thereof for the treatment of humans and/or other mammals it can optionally be formulated in accordance with pharmaceutical practice as a pharmaceutical composition. Therefore in another aspect of the invention there is provided a pharmaceutical composition comprising a compound of formula (I), or a pharmaceutically acceptable salt thereof, adapted for use in human or veterinary medicine.

In order to use a compounds of formula (I) or a pharmaceutically acceptable salt thereof in therapy, it will normally be formulated into a pharmaceutical composition in accordance with pharmaceutical practice. The present invention also provides a pharmaceutical composition, which comprises a compound of formula (I), or a pharmaceutically acceptable salt thereof, and a pharmaceutically acceptable carrier or excipient.

The pharmaceutical composition may be for use in a method of treatment or prophylaxis or in a use or in a treatment or prophylaxis, as described herein.

A pharmaceutical composition of the invention, which may be prepared by admixture, for example at ambient temperature and/or atmospheric pressure, is usually adapted for oral, parenteral or rectal administration. As such, the pharmaceutical composition may be in the form of a tablet, a capsule, a oral liquid preparation, a powder, a granule, a lozenge, a reconstitutable powder, an injectable or infusable solution or suspension, or a suppository.

An orally administrable pharmaceutical composition is generally preferred.

Tablets and capsules for oral administration may be in unit dose form, and may contain one or more excipients, such as a binding agent (e.g. hydroxypropylmethylcellulose or povidone), a filler (e.g. lactose and/or microcrystalline cellulose), a lubricant e.g. a tabletting lubricant (e.g. magnesium stearate or calcium stearate), a disintegrant (e.g. a tablet disintegrant such as sodium starch glycolate or croscarmellose sodium), and/or an acceptable wetting agent. The tablets may be coated e.g. according to methods known in pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain additive(s) such as a suspending agent(s), an emulsifying agent(s), a non-aqueous vehicle(s) (such as an edible oil), and/or a preservative(s), and/or, if desired, a flavouring(s) or colourant(s).

For parenteral administration, fluid unit dosage forms are typically prepared utilising a compound of the invention or pharmaceutically acceptable salt thereof and a sterile vehicle. In one embodiment, the compound or salt, depending on the vehicle and concentration used, is either suspended or dissolved in the vehicle. In preparing solutions, the compound or salt can e.g. be dissolved for injection and filter sterilised before filling into a suitable vial or ampoule and sealing. In one embodiment, an adjuvant(s) such as a local anaesthetic, a preservative(s) and/or a buffering agent(s) is or are dissolved in the vehicle. To enhance the stability, the composition can for example be frozen after filling into the vial and the water removed under vacuum. Parenteral suspensions are typically prepared in substantially the same manner, except that the compound or salt is typically suspended in the vehicle instead of being dissolved, and sterilization is not usually accomplished by filtration. The compound or salt can be sterilised, e.g. by exposure to ethylene oxide, before suspension in a sterile vehicle. In one embodiment, a surfactant or wetting agent is included in the composition, e.g. to facilitate uniform distribution of the compound or salt of the invention.

In one embodiment, the composition contains from 0.1% to 99% (by weight of the composition), in particular from 0.1 to 60% or 1 to 60% or 10 to 60% by weight, of the active material (the compound or pharmaceutically acceptable salt of the invention), e.g. depending on the method of administration. The carrier(s) and/or excipient(s) contained in the composition can for example be present in from 1% to 99.9%, e.g. from 10% to 99%, by weight of the composition; and/or in an amount of from 20 mg to 2000 mg such as 50 mg to 1000 mg per unit dose of the composition.

The dose of the compound or pharmaceutically acceptable salt thereof, e.g. for use in the treatment or prophylaxis (e.g. treatment) of the hereinmentioned disorders/diseases/conditions, may vary in the usual way with the seriousness of the disorders, the weight of the sufferer, and/or other similar factors. However, as a general guide, in one embodiment a unit dose of 0.05 to 2000 mg or 0.05 to 1000 mg, for example 0.05 to 200 mg, such as 20 to 40 mg, of the compound or pharmaceutically acceptable salt of the invention (measured as the compound), may be used, e.g. in a pharmaceutical composition. In one embodiment, such a unit dose is for administration once a day e.g. to a mammal such as a human; alternatively such a unit dose may be for administration more than once (e.g. twice or three times) a day e.g. to a mammal such as a human. Such therapy may extend for a number of days, weeks, months or years.

Combinations

Compounds of formula (I) or pharmaceutically acceptable salts thereof may be used in combination with other (further) therapeutic agent(s), for example medicaments claimed to be useful in the treatment or prophylaxis (e.g. treatment) of the above mentioned disorders.

Examples of such further therapeutic agent(s) may include a β2-agonist (also known as β2 adrenoceptor agonists; e.g. formoterol) and/or a corticosteroid (e.g. budesonide, fluticasone (e.g. as propionate or furoate esters), mometasone (e.g. as furoate), beclomethasone (e.g. as 17-propionate or 17,21-dipropionate esters), ciclesonide, triamcinolone (e.g. as acetonide), flunisolide, rofleponide or butixocort (e.g. as propionate ester)), e.g. for the treatment of a respiratory disorder (such as asthma or chronic obstructive pulmonary disease (COPD)), e.g. as described in WO 2007/008155 and/or WO 2007/008157.

A further therapeutic agent may include a 3-hydroxy-3-methylglutaryl coenzyme A (HMG CoA) reductase inhibitor (e.g. atorvastatin, fluvastatin, lovastatin, pravastatin, rosuvastatin, or simvastatin) (e.g. for oral administration), e.g. for the treatment of a cardiovascular disorder (such as atherosclerosis), e.g. as described in WO 2006/083214.

A further therapeutic agent may in particular include a non-steroid anti-inflammatory drug (NSAID; e.g. ibuprofen, naproxen, aspirin, celecoxib, diclofenac, etodolac, fenoprofen, indomethacin, ketoprofen, ketorolac, oxaprozin, nabumetone, sulindac, tolmetin, rofecoxib, valdecoxib, lumaricoxib, meloxicam, etoricoxib or parecoxib; or e.g. paracetamol, loxoprofen or aceclofenac; in particular celecoxib, paracetamol, ibuprofen or diclofenac) (e.g. for oral administration), e.g. for the treatment of an inflammatory disease or disorder (such as rheumatoid arthritis or osteoarthritis, and/or inflammatory pain), e.g. as described in WO 2005/025571. Celecoxib (a COX-2 inhibitor) can for example be administered orally at a dosage regimen of 100 mg or 200 mg (measured as the free base) once or twice daily.

A further therapeutic agent may in particular include a tumour necrosis factor α (TNFα) inhibitor (e.g. etanercept or an anti-TNFα antibody such as infliximab or adalimumab) (e.g. for parenteral administration such as subcutaneous or intravenous administration), e.g. for the treatment of an inflammatory disease or disorder (such as rheumatoid arthritis or osteoarthritis), e.g. as described in WO 2004/105798.

A further therapeutic agent may in particular include an anti-CD20 monoclonal antibody (e.g. for parenteral such as intravenous administration), such as ofatumumab (HuMax-CD20™, developed in part by Genmab AS) (e.g. ofatumumab for intravenous administration), rituximab, PRO70769, AME-133 (Applied Molecular Evolution), or hA20 (Immunomedics, Inc.); in particular ofatumumab or rituximab. This further therapeutic agent can e.g. be for the treatment of an inflammatory disease or disorder (such as rheumatoid arthritis or osteoarthritis, and/or inflammatory pain).

A further therapeutic agent may include 2-hydroxy-5-[[4-[(2-pyridinylamino)sulfonyl]phenyl]azo]benzoic acid (sulfasalazine), e.g. for the treatment of an inflammatory disease or disorder (such as rheumatoid arthritis or osteoarthritis; in particular rheumatoid arthritis), e.g. as described in WO 2004/105797.

A further therapeutic agent may in particular include N-[4-[[(2,4-diamino-6-pteridinyl)methyl]methylamino]benzoyl]-L-glutamic acid (methotrexate), e.g. for oral administration and/or e.g. for the treatment of an inflammatory disease or disorder (such as rheumatoid arthritis or osteoarthritis; in particular rheumatoid arthritis), e.g. as described in WO 2004/105796. For the treatment of rheumatoid arthritis, methotrexate can be administered to the human at a dosage regimen of 7.5 mg orally once weekly, or using divided oral doses of 2.5 mg at 12 hour intervals for 3 doses (7.5 mg total) as a course once weekly; the schedule can optionally be adjusted gradually to achieve an optimal response, but typically does not exceed a total weekly oral dose of 20 mg of methotrexate; once a response has been achieved, the methotrexate dose is typically reduced to the lowest possible effective dose.

A further therapeutic agent may include an inhibitor of pro TNFα convertase enzyme (TACE), e.g. for the treatment of an inflammatory disease or disorder (such as rheumatoid arthritis or osteoarthritis; in particular rheumatoid arthritis), e.g. as described in WO 2004/073704.

A further therapeutic agent may include:
a) sulfasalazine;
b) a statin (e.g. for oral administration), such as atorvastatin, lovastatin, pravastatin, simvastatin, fluvastatin, cerivastatin, crilvastatin, dalvastatin, rosuvastatin, tenivastatin, fluindostatin, velostatin, dalvastatin, nisvastatin, bervastatin, pitavastatin, rivastatin, glenvastatin, eptastatin, tenivastatin, flurastatin, rosuvastatin or itavastatin;
c) a glucocorticoid agent (e.g. for oral or skin-topical administration), such as dexamethasone, methylprednisolone, prednisolone, prednisone and hydrocortisone;
d) an inhibitor of p38 kinase (e.g. for oral administration);
e) an anti-IL-6-receptor antibody, e.g. an anti-IL-6-receptor monoclonal antibody (e.g. for parenteral such as intravenous administration);
f) anakinra;
g) an anti-IL-1 (e.g. IL-1β) monoclonal antibody (e.g. for parenteral such as intravenous administration);
h) an inhibitor of JAK3 protein tyrosine kinase;
i) an anti-macrophage colony stimulation factor (M-CSF) monoclonal antibody; or
j) an anti-CD20 monoclonal antibody (e.g. for parenteral such as intravenous administration), such as rituximab, ofatumumab (HuMax-CD20™, developed in part by Genmab AS) (e.g. ofatumumab for intravenous administration), PRO70769, AME-133 (Applied Molecular Evolution), or hA20 (Immunomedics, Inc.); in particular rituximab or ofatumumab;
e.g. for the treatment of an IL-1 (e.g. IL-1β) mediated disease (such as rheumatoid arthritis or osteoarthritis, and/or inflammatory or neuropathic pain; in particular rheumatoid arthritis), e.g. as described in WO 2006/003517.

In particular, the further therapeutic agent or agents can be a therapeutic agent or agents capable of treating inflammatory pain, such as paracetamol and/or an opioid analgesic (such as morphine, fentanyl, oxycodone, tramadol, hydrocodone, hydromorphone, oxymorphone, methadone or buprenorphine; in particular morphine, fentanyl, oxycodone, or tramadol). This/these therapeutic agent(s), and/or the combination comprising this/these therapeutic agent(s), can be for the treatment of inflammatory pain, e.g. in a mammal such as a human. For example, paracetamol can be administered at a human oral dosage regimen of 500 mg to 1000 mg (e.g. 500 mg, 650 mg or 1000 mg, in particular 650 mg) of paracetamol (measured as the free base/free compound), administered two, three or four times daily.

In a particular embodiment of the invention, the further therapeutic agent or agents can be a therapeutic agent or agents capable of treating neuropathic pain, such as:

an opioid analgesic (such as morphine, fentanyl, oxycodone, tramadol, hydrocodone, hydromorphone, oxymorphone, methadone or buprenorphine; in particular morphine, fentanyl, oxycodone, or tramadol, most particularly morphine),
a monoamine reuptake inhibitor (such as duloxetine or amytriptyline),
pregabalin,
gabapentin,
gabapentin enacarbil (XP13512), and/or
carbamazepine.

This/these therapeutic agent(s), and/or the combination comprising this/these therapeutic agent(s), can be for the treatment of neuropathic pain, e.g. in a mammal such as a human.

For example, pregabalin can be administered orally e.g. for neuropathic pain; e.g. at a human oral dosage regimen of 150 mg to 600 mg total pregabalin per day (measured as the free base), split between two to three doses per day. For example, for postherpetic neuralgia (a neuropathic pain condition), pregabalin can be administered at a starting oral dosage regimen of 150 mg total pregabalin per day (split between 2 or 3 doses per day), escalating (e.g. in about one week) to an oral dosage regimen of 300 mg pregabalin total per day, and optionally escalating up to a maximum oral dosage regimen of 600 mg total pregabalin per day. For painful diabetic neuropathy (another neuropathic pain condition), an oral dosage regimen of 150 mg to 300 mg total pregabalin per day can be administered. For fibromyalgia, an oral dosage regimen of 150 mg to 450 mg (e.g. 300 or 450 mg) total pregabalin per day can be administered. Pregabalin can e.g. be administered separately from the compound of formula (I) or the salt thereof.

For example, gabapentin can be administered orally, e.g. for neuropathic pain. Oral dosage units can e.g. contain 100 mg, 300 mg, 400 mg, 600 mg or 800 mg of gabapentin (measured as the free base/acid). The gabapentin dosage regimen for neuropathic pain can e.g. be from 300 mg once, twice or three times per day up to a total dose of 3600 mg/day. Some gradual up-titration of the dosage regimen is usually performed. For example, for peripheral neuropathic pain in adults, gabapentin therapy can be initiated by titrating the dose thus: day 1=300 mg of gabapentin (measured as the free base/acid) once a day, day 2=300 mg two times a day, and day 3=300 mg three times a day; alternatively the starting dose can be 900 mg/day of gabapentin (measured as the free base/acid), administered as three equally divided doses. Thereafter, e.g. based on individual patient response and tolerability, the dose can be further increased, typically in 300 mg/day increments every 2-3 days, up to a maximum total dose of 3600 mg/day of gabapentin (measured as the free base/acid). Slower titration of gabapentin dosage may be appropriate for individual patients. The minimum time to reach a total dose of 1800 mg/day is typically one week, to reach 2400 mg/day is typically a total of 2 weeks, and to reach 3600 mg/day is typically a total of 3 weeks. Gabapentin can e.g. be administered separately from the compound of formula (I) or the salt thereof.

For example, gabapentin enacarbil (XP13512, (±)-1-([(α-isobutanoyloxyethoxy)carbonyl]-aminomethyl)-1-cyclohexane acetic acid, which is a prodrug of gabapentin) can be administered orally, e.g. to a human, e.g. separately from the compound of formula (I) or the salt thereof. In one embodiment, gabapentin enacarbil (XP13512) is for example administered orally, e.g. to a human such as a human adult, e.g. at a total daily dose having an equivalent molar quantity of gabapentin enacarbil as the molar quantity present in 900 mg/day to 3600 mg/day of gabapentin (see e.g. page 81 lines 24-32 of WO 02/100347). A 600 mg dose of gabapentin enacarbil (measured as the free acid) contains the molar equivalent of 312 mg of gabapentin. See also K. C. Cundy et al., "Clinical Pharmacokinetics of XP13512, a Novel Transported Prodrug of Gabapentin", *J. Clin. Pharmacol.*, 2008, e-publication 30 Sep. 2008, incorporated herein by reference, and the Materials and Methods—Formulation and Study Designs sections therein, for examples of some oral doses, dosage regimens and formulations of XP13512 used in human pharmacokinetic studies.

In a particular embodiment of the invention, when the further therapeutic agent includes an opioid analgesic (such as morphine, fentanyl, oxycodone, tramadol, hydrocodone, hydromorphone, oxymorphone, methadone or buprenorphine; in particular morphine, fentanyl, oxycodone, or tramadol), then the opioid analgesic and/or the combination comprising the opioid analgesic is for the treatment of pain, in particular inflammatory or neuropathic pain, e.g. in a mammal such as a human. In a more particular embodiment of this embodiment, the compound or salt of the present invention is administered (e.g. to a human), e.g. either sequentially or simultaneously, in combination with the opioid analgesic, wherein the opioid analgesic is administered at a reduced dosage compared to the dosage (e.g. human dosage) typically used for said opioid analgesic (i.e. the compound or salt of the invention might give an opioid-sparing effect); this might give adequate pain control and/or might result in a reduction of opioid-analgesic-induced adverse events.

In a particular embodiment, the further therapeutic agent may be useful in the treatment or prophylaxis (in particular treatment) of a Neurodegenerative disease. For example the further therapeutic agent may be useful in alleviating the symptoms of a Neurodegenerative disease.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt thereof together with a further therapeutic agent or agents (e.g. as defined herein).

The individual components of the combination of the invention (i.e. the compound of formula (I) or the salt thereof, and the further therapeutic agent or agents) may be present as separate pharmaceutical formulations/compositions, or may be present as a combined pharmaceutical formulation/composition (e.g. may be together in a single combined oral dosage form, e.g. a single combined tablet or capsule). The individual components of this combination can for example be administered either sequentially in separate pharmaceutical formulations/compositions (e.g. oral), or simultaneously in separate or combined pharmaceutical formulation(s)/composition(s) (e.g. oral); in a particular embodiment they are administered sequentially in separate pharmaceutical formulations/compositions (e.g. oral).

The combinations referred to herein may optionally be presented for use in the form of a pharmaceutical formulation and thus pharmaceutical formulations comprising a combination as defined herein together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt thereof is used in combination with a second therapeutic agent active against the same disease state the dose of each compound may differ from that when the compound is used alone.

The following Examples and Intermediates illustrate the compounds of the invention, methods for their preparation, and intermediates usable in their preparation, but are not intended to be limiting.

EXPERIMENTAL SECTION

Abbreviations, some of which may be used herein, include the following:
Boc tert-butyl oxy carbonyl
DCM dichloromethane
DMA N, N-dimethylacetamide
DMAP 4-(dimethylamino)pyridine, also named N,N-dimethyl-4-pyridinamine
DME 1,2-dimethoxyethane
DMF N,N-dimethylformamide
DMSO dimethyl sulfoxide
DIPEA N,N-diisopropylethylamine ($^i$Pr$_2$NEt)
DPPF 1,1'-bis(diphenylphosphino)ferrocene
EDC 1-(3-dimethylaminopropyl)-3-ethylcarbodiimide hydrochloride
EtOAc ethyl acetate
Et$_2$O diethyl ether
EtOH ethanol
HCl hydrogen chloride
HEPES 4-(2-hydroxyethyl)-1-piperazine-1-ethanesulfonic acid

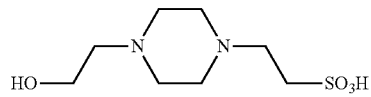

HOBT 1-hydroxybenzotriazole
IPA isopropanol (isopropyl alcohol)
MeCN acetonitrile
MeOH methanol
NaHCO$_3$ sodium hydrogen carbonate
NBS N-bromosuccinimide
NCS N-chlorosuccinimide
NIS N-iodosuccinimide
NH$_3$ ammonia
THF tetrahydrofuran
TFA trifluoroacetic acid
eq equivalents
HPLC high performance liquid chromatography
h hours
min minutes
LCMS or LC/MS liquid chromatography/mass spectrometry
MDAP mass directed automated (preparative) HPLC
MS mass spectrometry
NMR nuclear magnetic resonance
TLC thin layer chromatography
RT room temperature (ambient temperature); this is usually in the range of about 18 to about 25° C., or a sub-range within this range, unless otherwise disclosed herein.
SCX strong cation exchange. A SCX column or cartridge is typically a solid phase extraction (SPE) column with benzene sulfonic acid residues immobilised on the solid phase (eg. IST Isolute™ columns). When eluting with ammonia/methanol, it is thought that compounds isolated by SCX are usually in the free base form (if such a form exists).

INTERMEDIATES AND EXAMPLES

Reagents not detailed in the text below are usually commercially available from chemicals suppliers, e.g. established suppliers such as Sigma-Aldrich. The addresses and/or contact details of some suppliers of miscellaneous chemicals in general, which might be useful in sourcing starting materials, are as follows:

ABCR GmbH KG, Im Schlehert 10, Karlsruhe, D-76187, Germany, telephone: +49 (0)721-95061-0, Fax: +49 (0)721-95061-80, http://www.abcr.de AKos Consulting and Solutions GmbH, Austr. 26, Steinen, D-78585, Germany, telephone: +49 7627 970068, fax: +49 7627 970067, http://www.akosgmbh.eu Alchem Pharmtech, Inc., 160 Liberty Street, Bldg 4A, Metuchen, N.J., 08840, USA, telephone: +1 848-565-5694, fax: +1 732-317-4369, www.alchempharmtech.com Alfa Aesar, 26 Parkridge Road, Ward Hill, Mass., 01835, USA, telephone: 1-978-521-6300, Fax: 1-978-521-6350, http://www.alfa.com Allichem LLC, 8510 Corridor Road Step A, Savage, Md., 20763-9504, USA, telephone: +1 301-317-5072, Fax: +1 301-317-5073, http://www.allichemllc.com American Custom Chemicals Corp., P 0 Box 262527, San Diego, Calif., 92196-2527, USA, telephone: +1 858-201-6118, Fax: +1 858-451-8607, http://www.acccorporation.com Anichem LLC, 195 Black Horse Lane, North Brunswick, N.J., 08902, USA, telephone: +1 732-821-6500, fax: +1 732-821-6008, http://www.anichemllc.com APAC Pharmaceutical, LLC, 6851 Oak Hall Lane, Suite 101, Columbia, Md., 21045, USA, phone: +1 (410) 469-0727, fax: +1 (410) 309 5955, www.apacpharma.com Apollo Scientific Ltd., Whitefield Rd., Bredbury, Stockport, Cheshire, SK6 2QR, United Kingdom, telephone: +44 (0)161 406 0505, Fax: +44 (0)161 406 0506, http://www.apolloscientific.co.uk Ark Pharm, Inc., 1840 Industrial Drive, Suite 280, Libertyville, Ill., 60048, USA, telephone: +1-847-367-3680, fax: +1-847-367-3681, http://www.arkpharminc.com Atomole Scientific Co., Ltd, 150 Zhongjia Village, Suite 104, Hanyang District, Wuhan, Hubei, 430050, China, telephone: +86-27-82261049, fax: +86-27-82629206, http://www.atomole.com Aurora Fine Chemicals LLC, 7929 Silverton Ave., Suite 609, San Diego, Calif., 92126, USA, tel: +1 858 549 4700, fax: +1 858 549 4701, www.aurorafinechemicals.com Bepharm Ltd., 128 Xiangyin Road, Room C316, Yangpu District, Shanghai, 200433, China, phone: +86-21-51816456, fax: +86-21-51816457, http://www.bepharm.com Beta Pharma, Inc., 91 Shelton Avenue, Suite: 211, New Haven, Conn., 06511, USA, telephone: +1-877-786-1922, Fax: (203)786-5437, http://www.betapharma.com Bosche Scientific, LLC, New Brunswick Technology Center, 100 Jersey Avenue, Box D-12, Building D, 3rd Floor, New Brunswick, N.J., 08901, USA, telephone: +1 (732)-565-9988, fax: +1 (732)-875-0899, http://www.BoscheSci.com Bridge Organics, 311 W. Washington St., Vicksburg, Mich., 49097-1200, USA, telephone: +1 269-649-4200, fax: +1 269-649-0611, http://www.bridgeorganics.com ChemBridge Corporation, 16981 Via Tazon, Suite G, San Diego, Calif., 92127, USA, telephone: +1 (800) 964-6143, fax: +1 (858) 451-7401, http://www.chembridge.com ChemPacific Corp, 6200 Freeport Center, Baltimore, Md., 21224, USA, telephone: +00 1 410-633-5771, Fax: +001 410-633-5808, http://www.chempacific.com China Hallochem Pharma Co., Ltd., 17F, Venus Science Incubate Center, No. 60 Xingguang Road, New North Zone, Chongqing, 401121, China, telephone: +86-23-67030786, Fax: +86-23-67030809, http://www.hallochem.com D-L Chiral Chemicals, LLC, 53 Champlain Road, Monmouth Junction, N.J., 08852, USA, telephone: +1 732-668-8759, fax: +1 732-359-1599, http://www.dlchiral.com Fluorochem Ltd., Wesley Street, Old Glossop, Derbyshire, SK13 7RY, United Kingdom, telephone: +44 (0) 1457 868921, Fax: +44 (0) 1457 869360, http://www.fluorochem.net Haiso PharmChem, Hubei Research Institute of Chemistry, No. 30 Guanshan Road, Wuhan, 430074, China, telephone: +86-27-87422225, fax: +86-27-87496702, http://www.haisopharm.com Indofine Chemical Company, Inc., 121 Stryker Lane, Bldg 30, Suite 1, Hillsborough, N.J., 08844, USA, telephone: +1 (908) 359-6778, fax: +1 (908) 359-1179, http://www.indofinechemical.com International Laboratory Limited, 1067 Sneath Ln, San Bruno, Calif., 94066, USA, telephone: +1 650-278-9963, Fax: +1 650-589-2786, http://www.intlab.org J & W PharmLab LLC, 2000 Hartel Street, Suite B, Levittown, Pa., 19057, USA, telephone: +1-215-945-6595, fax: +1-215-945-6597, http://www.jwpharmlab.com JRD Fluorochemicals Ltd, Unit 11, Mole Business Park, Randalls Road, Leatherhead, Surrey, KT22 7BA, United Kingdom, telephone: +44 (0) 1372 360896, Fax: +44 (0) 1372 360790, http://www.jrdifluoro.co.uk Lanzhou Chon Chemical Co., Ltd., D6, Guchengping Industrial Park, Donggang Town, Lanzhou City, China, telephone: +86-138-93130096, fax: +86-931-4673545, http://www.chonchem.com Matrix Scientific, P 0 Box 25067, Columbia, S.C., 29224-5067, USA, telephone: 800-733-0244 (from USA and Canada) or (803) 788-9494 (all other calls), Fax: (803) 788-9419, http://www.matrixscientific.com Manchester Organics Ltd., Unit 2, Clifton Lane, Ashville Industrial Estate, Sutton Weaver, Runcorn, Cheshire, WA7 3FP, United Kingdom, telephone: +44 (0)1928 710 200, fax: +44 (0)1928 710 225, http://www.manchesterorganics.com Maybridge, Trevillett, Tintagel, Cornwall, PL34 0HW, United Kingdom, telephone: +44 (0)1840 770453, Fax: +44 (0)1840 770111, http://www.maybridge.com Oakwood Products, Inc., 1741 Old Dunbar Rd., West Columbia, S.C., 29172, USA, telephone: +1-800-467-3386, fax: +1 803-739-6957, http://www.oakwoodchemical.com Pfaltz & Bauer, Inc., 172 E. Aurora Street, Waterbury, Conn., 06708, USA, telephone: +1 (203) 574-0075, Fax: +1 (203) 574-3181, http://www.pfaltzandbauer.com Princeton BioMolecular Research, Inc., Princeton Corporate Plaza, 11 Deer Park Drive, Step. 114, Monmouth Junction, N.J., 08852, USA, telephone: +1 732-355-9920 ext. 102, fax: +1 732-355-9921, http://www.princetonbio.com Ryan Scientific, Inc., P 0 Box 703, Mt. Pleasant, S.C., 29465, USA, telephone: +1 888-884-4911, fax: +1 843-884-5568, http://www.ryansci.com Shanghai AOKChem Group Limited, No. 1768-4-302 Boxing Road, Shanghai, China, telephone: +86-21-68712331, Fax: +86-21-68712362, http://www.aokchem.com Shanghai FWD Chemicals Limited, Room 409, The Technological and Industrial Building, Meilong Road 130, Shanghai, 200237, China, telephone: +86-21-64251348, Fax: +86-21-64251330, http://www.fwdchem.com Shanghai PI Chemicals Ltd, Room 512, Building 1, 88 Cai Lun Road, Zhangjiang Hi-Tech Park, Pudong New Area, Shanghai, 201203, China, telephone: +86-21-58953700, Fax: +86-21-58953701, http://www.pipharma.com Shanghai Sinofluoro Scientific Corporation Ltd., Room113, Building 2, No. 969# Zhongshan South No. 2 Road, Shanghai, 200030, China, telephone: +86-21-642-793-60, fax: +86-21-642-786-03, http://www.sinofluoro.com Shanghai Specbiochem Co., Ltd., Unit A101-2, No. 326, Edison Rd, Zhangjiang High-tech Park, Shanghai, China, telephone: +86 21-51320052, Fax: +86 21-51320053, http://www.specbiochem.com Sigma-Aldrich, P O Box 14508, St. Louis, Mo., 63178, USA, Tel: 1-800-325-3010, Fax: 1-800-325-5052, http://www.sigma-aldrich.com Spectrum Chemicals and Laboratory Products, Inc., 14422 South San Pedro St., Gardena, Calif., 90248, USA, telephone: 800-395-6723, Fax: 310-516-7512, http://www.spectrumchemical.com Strem Chemicals, Inc., Dexter Industrial Park, 7 Mulliken Way, Newburyport, Mass., 01950-4098, USA, telephone: +1 (978) 499-1600, fax: +1 (978) 465-3104, http://www.strem.com Thermo Fisher Scientific, Janssens Pharmaceuticalaan 3A, Geel, 2440, Belgium, telephone: 0032 14 575261, Fax: 0032 14 593434, http://www.acros.com TimTec, Inc., Harmony Business Park 301-A, Newark, Del., 19711, USA, telephone: +1 (302) 292-8500, fax: +1 (302) 292-8520, http://www.timtec.net Tyger Scientific Inc., 324 Stokes Avenue, Ewing, N.J., 08638, USA, telephone: +1 609 434-0144, fax: +1 609 434-0143, http://www.tygersci.com UkrOrgSynthesis, 18 Mechnikova Street, Suite 92, Kiev, 01021, Ukraine, telephone: +38 044 531 94 97, Fax: +38 044 531 94 97, http://www.ukrorgsynth.com Vesino Industrial Co., Ltd., No. 4 Xinglanyuan Building, Changjiang Road, Tianjin, 300193, China, telephone: +86 22 81289555, fax: +86 22 27455635, http://www.vesino.com.cn Wako Pure Chemical Industries, Ltd., 1-2, Doshomachi 3-Chome, Chuo-ku, Osaka, 540-8605, Japan, telephone: +81-6-6203-3741, Fax: +81-6-6201-5964, http://www.wako-chem.co.jp Intermediates Intermediate 1 Imidazo[1,2-a]pyrazine (I1) (Also available from commercial sources)

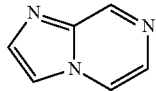

2-Pyrazinamine (9.51 g, 100 mmol) was dissolved in ethanol (300 ml) and 2-bromo-1,1-bis(ethyloxy)ethane (21.06 ml, 140 mmol) was added. 48% hydrobromic acid (33.3 ml) was added and the mixture heated at reflux for 24 hr. The solution was concentrated in vacuo to a crude solid that was basified with 10% ammonia-ice (300 ml). The solution was extracted in to ethyl acetate (3×300 ml), the combined extracts were washed with brine, dried over anhydrous sodium sulfate and concentrated in vacuo to afford a crude solid, (4.76 g). The solid was purified by flash chromatography (Biotage SP4, 40+M, eluting with a 0-100% [25% 2M ammonmia/methanol in dichloromethane] in dichloromethane gradient) to afford imidazo[1,2-a]pyrazine (2.86 g, 24.01 mmol, 24.01% yield).).

$^1$H NMR (CDCl3, 400 MHZ) δ 9.11 (s, 1H), 8.10 (d, 1H, J=4.8 Hz, 7.88 (d, 1H, 4.8 Hz, 7.83 (s, 1H), 7.71 (s, 1H)

Intermediate 2 3-Bromoimidazo[1,2-a]pyrazine (I2)

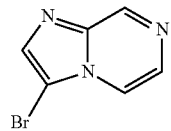

Imidazo[1,2-a]pyrazine (1.191 g, 10 mmol, Intermediate 1) and sodium acetate (0.984 g, 12.00 mmol) were suspended in methanol (10 ml) saturated with potassium bromide (excess) and cooled to −10° C. Bromine (0.515 mL, 10.00 mmol) was added dropwise and the mixture stirred at −10° C. for 10 min. The solution was quenched by the addition of 1N sodium sulfite solution (10 ml) and concentrated in vacuo. The residue was partitioned between ethyl acetate (100 ml) and 50% saturated sodium bicarbonate solution (100 ml). The aqueous phase was extracted with ethyl acetate (2×100 ml), combined, washed with brine (50 ml), dried over anhydrous sodium sulfate and concentrated to give crude 3-bromoimidazo[1,2-a]pyrazine (1.66 g, 8.38 mmol, 84% yield) that was used in subsequent steps without further purification 3-bromoimidazo[1,2-a]pyrazine (1.66 g, 8.38 mmol, 84% yield).

LC/MS [M+H]+=198, 200, retention time=0.53 minutes (2 minute method).

$^1$H NMR (CDCl3, 400 MHz) δ 9.09 (s, 1H), 8.08 (s 1H), 7.94 (s, 1H), 7.81 (s, 1H).

Intermediate 3
3-Phenyl-5,6,7,8-tetrahydroimidazo[1,2-a]pyrazine (I3)

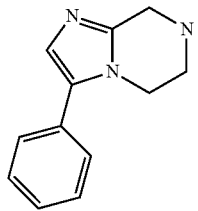 [SMILES: c1ccc(-c2cnc3n2CCNC3)cc1]

3-Phenylimidazo[1,2-a]pyrazine (1.391 g, 7.13 mmol) was dissolved in ethanol (100 ml) and hydrogenated at room temperature under 1 Atm hydrogen over platinum(IV) oxide (0.202 g, 0.713 mmol) for 24 hours. The catalyst was filtered, washed with ethanol and the filtrate concentrated to afford 3-phenyl-5,6,7,8-tetrahydroimidazo[1,2-a]pyrazine (1.41 g, 7.08 mmol, 99% yield)

LC/MS [M+H]+=200, retention time=0.30 minutes (5 minute method).

$^1$H NMR (CDCl3, 400 MHz) δ 7.7-7.3 (m, 5H), 7.06 (s, 1H), 4.20 (s, 2H), 3.97 (m, 2H), 3.23 (m, 2H).

The 3-phenylimidazo[1,2-a]pyrazine used in the above method was prepared as follows:

3-Bromoimidazo[1,2-a]pyrazine (1.66 g, 7.13 mmol, Intermediate 2), sodium carbonate (3.78 g, 35.6 mmol) and phenylboronic acid (1.043 g, 8.55 mmol) were dissolved in 1,2-dimethoxyethane (DME) (40 ml) and water (20 ml). Bis (triphenylphosphine)palladium (II) chloride (0.250 g, 0.356 mmol) was added and the biphasic solution heated at 80° C. for 16 h. The aqueous phase was extracted with ethyl acetate (3×100 ml) and the combined extracts washed with saturated sodium bicarbonate solution (100 ml), water (100 ml), brine (100 ml) and dried by passing through a hydromatrix cartridge (Varian). The filtrate was concentrated in vacuo to afford a crude oil (2.44 g). The crude product was purified by flash chromatography (Biotage SP4, 40+M, eluting with a 0-100% gradient of ethylacetate in hexane)—(the product elutes in 100% ethyl acetate), to afford 3-phenylimidazo[1,2-a]pyrazine (1.22 g, 6.25 mmol, 88% yield).

LC/MS [M+H]+=196, retention time=1.63 minutes (5 minute method).

Intermediate 4 2-(Trifluoromethyl)-5,6,7,8-tetrahydroimidazo[1,2-a]pyrazine (I4)

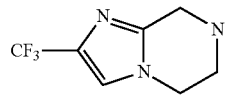

2-(Trifluoromethyl)imidazo[1,2-a]pyrazine (1.63 g, 8.71 mmol) was dissolved in methanol (70 mL) and hydrogenated at RT under 1 atm hydrogen over 10% palladium on carbon paste (0.464 g, 0.436 mmol) for 16 h. The catalyst was filtered and the filtrate concentrated to an oil that solidified upon standing to a waxy solid 2-(trifluoromethyl)-5,6,7,8-tetrahydroimidazo[1,2-a]pyrazine (1.56 g, 8.16 mmol, 94% yield).

$^1$H NMR (CDCl$_3$, 400 MHz) δ 7.15 (s, 1H) 4.12 (s, 2H), 4.08 (m, 2H), 3.28 (m, 2H).

The 2-(trifluoromethyl)imidazo[1,2-a]pyrazine used in the above procedure was prepared as follows:

2-Pyrazinamine (4.76 g, 50 mmol) was dissolved in ethanol (120 ml) and 3-bromo-1,1,1-trifluoro-2-propanone (5.19 ml, 50.0 mmol) was added. The solution was heated at reflux for 24 h. The solution was concentrated in vacuo and the residue partitioned between saturated sodium bicarbonate solution (100 ml) and ethyl acetate (100 ml). The aqueous phase was extrated with ethyl acetate (3×100 ml), combined extracts were washed with brine (2×100 ml), dried over anhydrous magnesium sulfate and concentrated to a crude solid (6.72 g). The solid was purified by flash chromatography (Biotage SP4, 40+M, eluting with a 25-100% ethyl acetate/hexane gradient) to afford product (3.72 g) which was further purified (Biotage SP4, 40+M, eluting with a 0-100% gradient of 25% 2M ammonia/methanol in dichloromethane/dichloromethane) to afford purer material product (2.11 g). The solid was recrystalised from a small volume of IPA to afford 2-(trifluoromethyl)imidazo[1,2-a]pyrazine (1.63 g, 8.71 mmol, 17.42% yield) as off white plates.

LC/MS [M+H]+=188, retention time=1.38 minutes (5 minute method).

Intermediate 5
2-Ethyl-5,6,7,8-tetrahydroimidazo[1,2-a]pyrazine (I5)

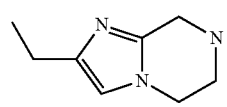

2-Ethyl-5,6,7,8-tetrahydroimidazo[1,2-a]pyrazine was prepared in an analogous manner to that described above for 2-(trifluoromethyl)-5,6,7,8-tetrahydroimidazo[1,2-a]pyrazine (Intermediate 4) but starting from 1-bromo-2-butanone instead of 3-bromo-1,1,1-trifluoro-2-propanone and using platinum (IV) oxide and ethanol in the place of 10% palladium on carbon paste and methanol for the hydrogenation step.

$^1$H NMR (CDCl$_3$, 400 MHz) δ 6.51 (s, 1H), 4.08 (s, 2H), 3.89 (m, 2H), 3.22 (m, 2H), 2.57 (q, 2H, J=7.6 Hz), 1.21 (t, 3H, J=7.6 Hz).

Intermediate 6
2-Methyl-5,6,7,8-tetrahydroimidazo[1,2-a]pyrazine (I6)

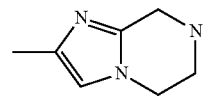

2-Methyl-5,6,7,8-tetrahydroimidazo[1,2-a]pyrazine was prepared in an analogous manner to that described above for 2-(trifluoromethyl)-5,6,7,8-tetrahydroimidazo[1,2-a]pyrazine (Intermediate 4) but starting from 1-chloro-2-propanone instead of 3-bromo-1,1,1-trifluoro-2-propanone and using platinum (IV) oxide and ethanol in the place of 10% palladium on carbon paste and methanol for the hydrogenation step.

$^1$H NMR (CDCl$_3$, 400 MHz) δ 6.52 (s, 1H), 4.24 (s, 2H), 3.88 (m, 2H), 3.21 (m, 2H), 2.21 (s, 3H).

Intermediate 7 2-(1,1-Dimethylethyl)-5,6,7,8-tetrahydroimidazo[1,2-a]pyrazine (I7)

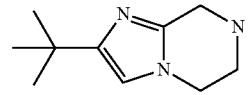

2-(1,1-Dimethylethyl)-5,6,7,8-tetrahydroimidazo[1,2-a]pyrazine was prepared in an analogous manner to that described above for 2-(trifluoromethyl)-5,6,7,8-tetrahydroimidazo[1,2-a]pyrazine (Intermediate 4) but starting from 1-bromo-3,3-dimethyl-2-butanone instead of 3-bromo-1,1,1-trifluoro-2-propanone and using platinum (IV) oxide and ethanol in the place of 10% palladium on carbon paste and methanol for the hydrogenation step.

$^1$H NMR (CDCl$_3$, 400 MHz) δ 6.50 (s 1H), 4.08 (s 2H), 3.90 (m, 2H), 3.22 (m, 2H), 1.27 (s, 9H).

Intermediate 8
2-Phenyl-5,6,7,8-tetrahydroimidazo[1,2-a]pyrazine (I8)

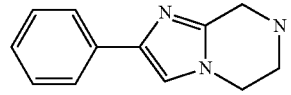 [SMILES: c1ccc(-c2cn3c(n2)CNCC3)cc1]

2-Phenyl-5,6,7,8-tetrahydroimidazo[1,2-a]pyrazine was prepared in an analogous manner to that described above for 2-(trifluoromethyl)-5,6,7,8-tetrahydroimidazo[1,2-a]pyrazine (Intermediate 4) but starting from 2-bromo-1-phenylethanone instead of 3-bromo-1,1,1-trifluoro-2-propanone and using platinum (IV) oxide and ethanol in the place of 10% palladium on carbon paste and methanol for the hydrogenation step.

LC/MS [M+H]+=200, retention time=0.44 minutes (2 minute method).

Intermediate 9 3-(2-Pyridinyl)-5,6,7,8-tetrahydroimidazo[1,2-a]pyrazine[1,2-a]pyrazine (I9)

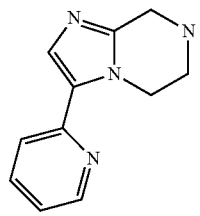 [SMILES: c1ccc(-c2cnc3n2CCNC3)nc1]

3-(2-Pyridinyl)imidazo[1,2-a]pyrazine (0.319 g, 1.626 mmol) was hydrogenated at 50 p.s.i. at room temperature for 24 h over 10% palladium on carbon paste (0.0346 g, 0.163 mmol) in methanol (20 mL). The reaction was continued for a further 24 hours at 50 p.s.i. hydrogen pressure and at 50° C. The catalyst was filtered and concentrated in vacuo to give crude 3-(2-pyridinyl)-5,6,7,8-tetrahydroimidazo[1,2-a]pyrazine[1,2-a]pyrazine which was used without further purification.

The 3-(2-pyridinyl)imidazo[1,2-a]pyrazine used in the above method was prepared as follows:

Imidazo[1,2-a]pyrazine (0.715 g, 6 mmol, Intermediate 1), 2-bromopyridine (0.644 mL, 6.60 mmol), triphenylphosphine (0.315 g, 1.200 mmol), and palladium(II) acetate (0.135 g, 0.600 mmol) were heated in N,N-dimethylacetamide (DMA) (8 mL) at 150° C. for 5 hr in a microwave reactor. The bulk of the DMA was removed in vacuo and the residue partitioned between 10% isopropanol/DCM (100 ml) and saturated sodium bicarbonate solution (50 ml). Solids were removed by filtration through celite and the filtrated separated. The aqueous phase was extracted with 10% isopropanol/DCM (3×50 ml. The combined organic extracts were dried over anhydrous sodium sulfate and concentrated in vacuo to afford a crude oil, (2.6 g). The crude oil was partially purified by flash chromatography (Biotage SP4, 40+M, eluting with a 0-100% gradient of [(2M ammonia methanol/Ethyl acetate]/ethyl acetate) to afford material (1.59 g) which was repurified by flash chromatography (Biotage SP4, 40+M, eluting with a 0-100% gradient of [(2M ammonia methanol/Ethyl acetate]/ethyl acetate) to afford 3-(2-pyridinyl)imidazo[1,2-a]pyrazine (0.319 g, 1.626 mmol, 27.1% yield).

$^1$H NMR (CDCl$_3$, 400 MHZ) δ 9.82 (dd, 1H, J=3.6, 1.2 Hz), 9.19 (d, 1H, J=1.6 Hz), 8.72 (1H, m), 8.03 (d, 1H, J=4.8 Hz), 7.84-7.91 m (2H), 7.29-7.21 m (2H).

Intermediate 10 4-[(2,3-Dichlorophenyl)carbonyl]-2-piperazinone (I10)

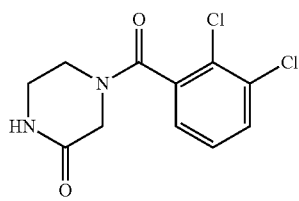 [SMILES: O=C1CN(C(=O)c2cccc(Cl)c2Cl)CCN1]

To a suspension of 2-piperazinone (5.3 g, 52.9 mmol) in dry dichloromethane (DCM) (76 ml) was added triethylamine (16.23 ml, 116 mmol) and finally 2,3-dichlorobenzoyl chloride (12.20 g, 58.2 mmol) dropwise (exothermic). The mixture was stirred at room temperature. After 1 hour the mixture was diluted with DCM (150 mL) and sat. NaHCO3 (150 ml), the phases were separated and the aqueous layer extracted with DCM (2×100 ml). The combined organic fractions were washed with brine and dried over MgSO4. Evaporation gave 4-[(2,3-dichlorophenyl)carbonyl]-2-piperazinone (12 g).

LC/MS [M+H]+=272.93, retention time=0.69 minutes (2 minute method).

Intermediate 11 2-(Trifluoromethyl)imidazo[1,2-a]pyrazine (I11)

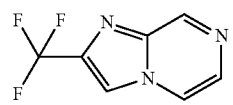 [SMILES: FC(F)(F)c1cn2ccncc2n1]

2-Pyrazinamine (11.89 g, 125 mmol, commercially available from e.g. Sigma-Aldrich, Fluka or Acros) was dissolved in isopropanol (IPA) (200 mL) and 3-bromo-1,1,1-trifluoro-2-propanone (12.98 mL, 125 mmol) was added. The solution was stirred at room temperature for 2 hours and the heated at reflux for 18 h. The solution was concentrated in vacuo and the residue partitioned between saturated sodium bicarbonate solution (200 ml) and 20% IPA/DCM (300 ml). The aqueous phase was extracted with 20% IPA/DCM (5×200 ml) and the combined extracts were concentrated in vacuo. The residue was dissolved in ethyl acetate (500 ml) and washed with brine (2×100 ml), dried over anhydrous sodium sulfate and concentrated in vacuo to afford a crude solid (17.69 g). The solid was dissolved in dichloromethane and initially purified by filtration through a plug of silica to afford product in 15.14 g. The solid was purified by flash chromatography (Biotage flash 65+, 0-100% [10% 2M NH$_3$ in MeOH/DCM]/DCM) to afford the desired product in 5.61 g. LC/MS=408/410 (M+H)$^+$, retention time=2.05 minutes (5 minute).

Intermediate 12 3-bromo-2-(trifluoromethyl)imidazo[1,2-a]pyrazine (I12)

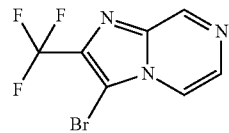 [SMILES: FC(F)(F)c1nc2cnccn2c1Br]

2-(Trifluoromethyl)imidazo[1,2-a]pyrazine(I11) (2.5 g, 13.36 mmol) was dissolved in N,N-dimethylformamide (DMF) (5 mL) and NBS (2.497 g, 14.03 mmol) was added. The solution was stirred at RT for 48 hours. The bulk of the DMF was removed in vacuo and the residue was poured on to ice-water (25 ml). The solution was basified with saturated sodium bicarbonate solution (25 ml) and extracted in to ethyl acetate (3×50 ml). The combined extracts were washed with water (50 ml), 50% brine (50 ml), brine (50 ml) and dried over anhydrous sodium sulfate to afford crude product in 3.88 g. The crude product was purified by flash chromatography (SP4, 40+M, 0-100% methanol:dichloromethane (1:9)/ dichloromethane) to afford product in 3.44 g. The product was further purified by flash chromatography (SP4, 40+M, 0-100% ethyl acetate/iso-hexane) to afford product in 2.49 g.

LC/MS=267/269 (M+H)+, retention time=0.85 minutes (2 minute).

Intermediate 13 3-(4-fluorophenyl)-2-(trifluoromethyl)imidazo[1,2-a]pyrazine (I13)

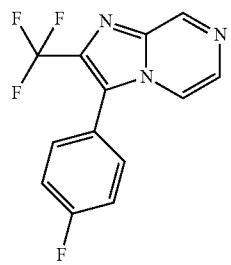 [SMILES: Fc1ccc(-c2c(C(F)(F)F)nc3cnccn23)cc1]

3-Bromo-2-(trifluoromethyl)imidazo[1,2-a]pyrazine (I12) (1.330 g, 5 mmol), (4-fluorophenyl)boronic acid (1.049 g, 7.50 mmol), sodium carbonate (2.65 g, 25.00 mmol) and Bis(triphenylphosphine)palladium (II) chloride (0.351 g, 0.500 mmol) were heated at 80° C. for 7 h in water (10 ml) and 1,2-dimethoxyethane (DME) (20 ml). The mixture was passed through a hydromatrix cartridge (Varian, 20 g) and washed through with dichloromethane. The filtrated was concentrated in vacuo to afford a tacky oil. The product was purified by flash chromatography (Isolera, 100 g, 0-100% 2M ammonia in methanol:dichloromethane (1:9)/dichloromethane) to afford product in 2.03 g. The compound was repurified by flash chromatography (Isolera, 100 g, 0-100% ethyl acetate/iso-hexane) to afford product in 1.42 g as beige solid.

LC/MS=281 (M+H)+, retention time=0.96 minutes (2 minute method).

Intermediate 14 3-(4-fluorophenyl)-2-(trifluoromethyl)-5,6,7,8-tetrahydroimidazo[1,2-a]pyrazine (I14)

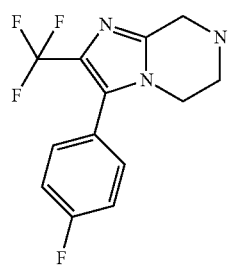 [SMILES: Fc1ccc(-c2c(C(F)(F)F)nc3n2CCNC3)cc1]

3-(4-Fluorophenyl)-2-(trifluoromethyl)imidazo[1,2-a]pyrazine(I13) (1.4 g, 4.98 mmol) was hydrogenated at RT/1 atm hydrogen over platinum(IV) oxide (0.141 g, 0.498 mmol) dissolved in ethanol (40 mL) for 24 h. The catalyst was filtered and the filtrate concentrated in vacuo to afford product in 1.4 g as a tacky solid.

LC/MS=286 (M+H)+, retention time=0.85 minutes (2 minute method (high pH)).

Intermediate 15 3-bromo-7-{[2-chloro-3-(trifluoromethyl)phenyl]carbonyl}-5,6,7,8-tetrahydroimidazo[1,2-a]pyrazine (I15)

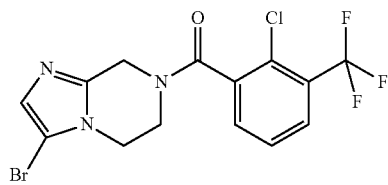 [SMILES: O=C(c1cccc(C(F)(F)F)c1Cl)N1CCn2c(Br)cnc2C1]

7-{[2-Chloro-3-(trifluoromethyl)phenyl]carbonyl}-5,6,7,8-tetrahydroimidazo[1,2-a]pyrazine (E1) (5.68 g, 17.23 mmol) was dissolved in N,N-dimethylformamide (DMF) (100 mL) and treated with NBS (3.22 g, 18.09 mmol). The solution was stirred at 25° C. for 16 h and the bulk of the DMF was removed in vacuo. The residue was partitioned between dichloromethane (500 ml) and saturated sodium bicarbonate solution (100 ml). The aqueous phase was extracted with dichloromethane (5×100 ml) during which filtration through celite was required to remove emulsions and precipitated succinimide. The combined organic extracts were washed with brine (100 ml), dried over anhydrous sodium sulfate and concentrated to a crude oil. The crude product was purified by flash chromatography (Isolera, 340 g, 0-100% methanol:dichloromethane (1:9)/dichloromethane) to afford an oil that was triturated with hexane to afford a solid of desired product in 5.90 g.

LC/MS=408/410/412 (M+H)+, retention time=0.90 minutes (2 minute method).

Intermediate 16
5-fluoro-2-(trimethylstannanyl)pyridine (I16)

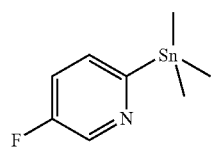

A solution of 2-bromo-5-fluoropyridine (0.66 g, 3.75 mmol, commercially available from e.g. Sigma-Aldrich) and hexamethyldistannane (0.778 ml, 3.75 mmol, commercially available from e.g. Fluka or Sigma-Aldrich) in anhydrous 1,4-dioxane (12.50 ml) was degassed by sonication under a flow of argon for 5 minutes before palladium tetrakis (0.217 g, 0.188 mmol) was added and the mixture was exposed to microwaves at 150° C. for 10 minutes. LCMS showed conversion to the desired stannane (MH+=264 major isotope, characteristic Sn isotopic pattern present, Rt=0.5). It was filtered through a pad of celite, concentrated in vacuo and purified on neutral alumina with a gradient of DCM 0 to 10% in iso-hexane to afford the desired product in 240 mg as a colourless oil which crystallised upon standing.

LCMS [M+H]+ 259.81 @0.49 min (2 min run), shows characteristic tin splitting

Intermediate 17
5,6,7,8-tetrahydroimidazo[1,2-a]pyrazine (I17)

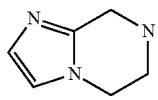

Imidazo[1,2-a]pyrazine(I1) (4.38 g, 36.8 mmol) was dissolved in methanol (100 mL) and hydrogenated at 1 atm/25° C. hydrogen over platinum(IV) oxide (0.522 g, 1.838 mmol) for 24 h. The catalyst was filtered and the filtrate concentrated to afford product in 4.8 g that was used without further purification.

LC/MS=124 (M+H)+, retention time=0.34 minutes (2 minute method (high pH)).

Intermediate 18 1,1-dimethylethyl 5,6-dihydroimidazo[1,2-a]pyrazine-7(8H)-carboxylate (I18)

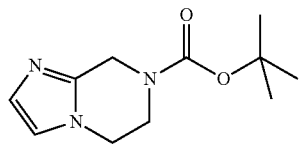 [SMILES: CC(C)(C)OC(=O)N1CCn2ccnc2C1]

5,6,7,8-Tetrahydroimidazo[1,2-a]pyrazine(I17) (4.53 g, 36.8 mmol) and triethylamine (6.16 mL, 44.2 mmol) were dissolved in dichloromethane (DCM) (200 mL) and treated with di-tert-butyl dicarbonate (10.25 mL, 44.2 mmol). The solution was stirred at RT for 48 h and concentrated in vacuo to afford a crude oil. The crude product was purified by flash chromatography (Isolera, 340 g, 0-100% 2M ammonia in methanol:dichloromethane (1:9)/dichloromethane) to afford 3 fractions. Fraction 2 was identified by LC/MS as containing desired product. The residue was dissolved in ethyl acetate (300 ml), washed with saturated sodium bicarbonate solution (50 mL), water (2×50 mL), brine (50 mL), dried over anhydrous sodium sulfate and concentrated to afford product in 6.77 g.

LC/MS=224 (M+H)+, retention time=0.71 minutes (2 minute method (high pH)).

Intermediate 19 1,1-dimethylethyl 3-chloro-5,6-dihydroimidazo[1,2-a]pyrazine-7(8H)-carboxylate (I19)

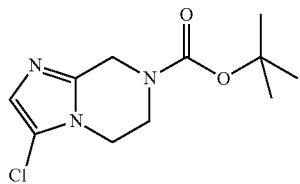 [SMILES: CC(C)(C)OC(=O)N1CCn2c(Cl)cnc2C1]

1,1-Dimethylethyl 5,6-dihydroimidazo[1,2-a]pyrazine-7(8H)-carboxylate (I18) (1.563 g, 7 mmol) and NCS (0.935 g, 7.00 mmol) were heated at 80° C. for 2 h in toluene (30 mL). The solvents were removed in vacuo and the residue was purified by flash chromatography (Isolera, 50 g, 0-100% ethyl acetate/iso-hexane) to afford product in 1.55 g.

LC/MS=258/260 (M+H)+, retention time=0.64 minutes (2 minute method).

Intermediate 20
3-chloro-5,6,7,8-tetrahydroimidazo[1,2-a]pyrazine (I20)

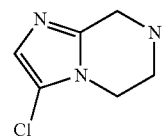

1,1-Dimethylethyl 3-chloro-5,6-dihydroimidazo[1,2-a]pyrazine-7(8H)-carboxylate (I19) (1.55 g, 6.01 mmol) and 4N HCl in 1,4-dioxane (6.01 mmol) was stirred at RT in 1,4-dioxane (5 mL) for 16 h. Solvents were removed in vacuo and the residue was loaded on to SCX (Varian 2×10 g) in methanol. The columns were washed with methanol and basic products eluted with 2M ammonia/methanol. The basic fractions were concentrated in vacuo to afford product in 913 mg that was used in subsequent steps without further purification.

LC/MS=158/160 (M+H)+, retention time=0.44 minutes (2 minute method (high pH)).

Intermediate 21 7-[(2-chloro-4-fluorophenyl)carbonyl]-5,6,7,8-tetrahydroimidazo[1,2-a]pyrazine (I21)

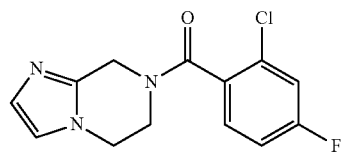 [SMILES: O=C(c1ccc(F)cc1Cl)N1CCn2ccnc2C1]

5,6,7,8-Tetrahydroimidazo[1,2-a]pyrazine(I17) (620 mg, 3.07 mmol) and diethylaminomethyl polystyrene (3071 mg, 9.83 mmol) were slurried in dichloromethane (DCM) (20 mL). 2-Chloro-4-fluorobenzoyl chloride (622 mg, 3.22 mmol, commercially available from e.g. Sigma-Aldrich, Maybridge or Fluorochem) was added and the slurry stirred at 25° C. for 3 h. The resin was removed by filtration, washed with dichloromethane (50 ml) and the filtrate concentrated in vacuo to afford a crude oil. The crude product was purified by flash chromatography (Isolera, 100 g, 0-100% 2M ammonia in methanol:dichloromethane (1:9)/dichloromethane) to afford product. This was further purified by flash chromatography (Isolera, 50 g, 0-100% methanol:dichloromethane (1:9)/dichloromethane), to afford product. The oil was further purified by MDAP to afford clean product as the formate salt. The solid was loaded on to an SCX cartridge (Varian, 5 g) and washed with methanol. The product was eluted with 2M ammonia methanol and the filtrate concentrated to afford desired product in 330 mg as a white solid.

LC/MS=280/282 (M+H)+, retention time=0.52 minutes (2 minute).

Intermediate 22 7-[(2-chloro-4-fluorophenyl)carbonyl]-2-(trifluoromethyl)-5,6,7,8-tetrahydroimidazo[1,2-a]pyrazine (I22)

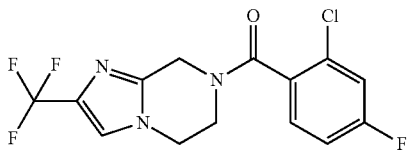 [SMILES: O=C(c1ccc(F)cc1Cl)N1CCn2cc(C(F)(F)F)nc2C1]

2-(Trifluoromethyl)-5,6,7,8-tetrahydroimidazo[1,2-a]pyrazine (I4) (287 mg, 1.5 mmol) and DIPEA (0.314 mL, 1.800 mmol) were dissolved at 0° C. in dichloromethane (DCM) (15 mL). 2-chloro-4-fluorobenzoyl chloride (290 mg, 1.500 mmol, commercially available from e.g. Sigma-Aldrich, Maybridge or Apollo) dissolved in DCM (5 mL) was added dropwise and the solution stirred to room temperature over 4 h. Solvents were removed in vacuo and the residue was partitioned between dichloromethane (50 mL) and saturated sodium bicarbonate solution (25 mL). The aqueous phase was extracted with dichloromethane (3×50 mL) and the combined extracts were washed with water (50 mL), brine (50 mL), dried over anhydrous sodium sulfate and concentrated in vacuo to afford a crude oil (759 mg). The crude product was purified by flash chromatography (Isolera, 25 g, 0-100% 2M ammonia in methanol:dichloromethane (1:9)/dichloromethane) to afford crude product. Concentration of the waste afforded material which was also identified as product. Samples were combined to afford crude product. This was purified by MDAP, product containing fractions concentrated and loaded directly on to an SCX cartridge (Varian, 10 g). The column was washed with methanol and the product eluted with 2M ammonia methanol. The solvents were evaporated in vacuo to afford the desired product in 318 mg.

LC/MS=348/350 (M+H)+, retention time=0.94 minutes (2 minute method)

Examples

The general methods (a)-(e), along with the synthetic methods outlined in Schemes 1-5 above, for the preparation of compounds of the present invention are further illustrated by the following examples.

Example 17-{[2-Chloro-3-(trifluoromethyl)phenyl]carbonyl}-5,6,7,8-tetrahydroimidazo[1,2-a]pyrazine (E1)

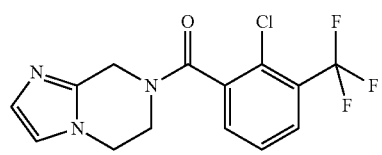 [SMILES: O=C(c1cccc(C(F)(F)F)c1Cl)N1CCn2ccnc2C1]

5,6,7,8-Tetrahydroimidazo[1,2-a]pyrazine (0.099 g, 0.804 mmol) was suspended in dichloromethane (DCM) (8 ml). Triethylamine (0.123 mL, 0.884 mmol) and 2-chloro-3-(trifluoromethyl)benzoyl chloride (0.195 g, 0.804 mmol) were added and the mixture was stirred at room temperature for 5 hours. The reaction mixture was concentrated in vacuo, the residue dissolved in 1:1 DMSO/MeOH and purified by mass-directed automated preparative HPLC. Product fractions were concentrated in vacuo to yield an orange gum. This was partitioned between DCM (10 ml) and saturated aqueous sodium bicarbonate (4 ml) and the organic layer separated. This was concentrated in vacuo to yield 7-{[2-chloro-3-(trifluoromethyl)phenyl]carbonyl}-5,6,7,8-tetrahydroimidazo[1,2-a]pyrazine (0.131 g, 0.397 mmol, 49.4% yield) as a yellow gum.

LC/MS [M+H]+=330, retention time=1.02 minutes (5 minute method).

Example 27-{[2-Chloro-3-(trifluoromethyl)phenyl]carbonyl}-2-(trifluoromethyl)-5,6,7,8-tetrahydroimidazo[1,2-a]pyrazine (E2)

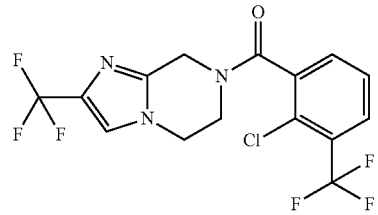 [SMILES: O=C(c1cccc(C(F)(F)F)c1Cl)N1CCn2cc(C(F)(F)F)nc2C1]

2-(Trifluoromethyl)-5,6,7,8-tetrahydroimidazo[1,2-a]pyrazine (1.06 g, 5.55 mmol, Intermediate 4) and triethylamine (0.850 ml, 6.10 mmol) were dissolved in dichloromethane (DCM) (25 ml). 2-chloro-3-(trifluoromethyl)benzoyl chloride (1.348 g, 5.55 mmol) was added and the mixture stirred at room temperature for 24 h. The solvents were removed in vacuo and the solid partitioned between dichloromethane (100 ml) and saturated sodium bicarbonate solution (50 ml). The aqueous phase was extracted with dichloromethane (3×50 ml), the combine organic extracts were dried over anhydrous sodium sulfate and then concentrated to afford 7-{[2-chloro-3-(trifluoromethyl)phenyl]carbonyl}-2-(trifluoromethyl)-5,6,7,8-tetrahydroimidazo[1,2-a]pyrazine (2.22 g, 5.58 mmol, 101% yield).

LC/MS [M+H]+=398, 400, retention time=1.04 minutes (2 minute method).

Example 37-[(2,4-Dichlorophenyl)carbonyl]-2-(trifluoromethyl)-5,6,7,8-tetrahydroimidazo[1,2-a]pyrazine (E3)

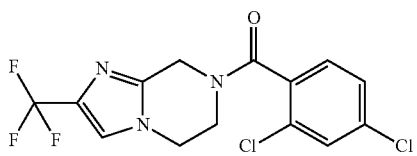 [SMILES: O=C(c1ccc(Cl)cc1Cl)N1CCn2cc(C(F)(F)F)nc2C1]

2-(Trifluoromethyl)-5,6,7,8-tetrahydroimidazo[1,2-a]pyrazine (0.096 g, 0.5 mmol, intermediate 4) and diethylaminomethyl polystyrene (0.469 g, 1.500 mmol) were slurried in dichloromethane (DCM) (5 ml). 2,4-Dichlorobenzoyl chloride (0.084 ml, 0.600 mmol) was added and the mixture stirred at room temperature for 24 h. The resin was filtered, washed with dichloromethane and the filtrate concentrated in vacuo to afford crude product which was purified by flash chromatography (Biotage SP4, 25+S, eluting with a 0-100% gradient of ethyl acetate/iso-hexane) to afford 7-[(2,4-dichlorophenyl)carbonyl]-2-(trifluoromethyl)-5,6,7,8-tetrahydroimidazo[1,2-a]pyrazine (0.178 g, 0.489 mmol, 98% yield).

LC/MS [M+H]+=364, 366, 368, retention time=2.30 minutes (5 minute method).

Examples 4 to 16

In a manner analogous to that described for Example 3 above the compounds tabulated below (Table 1) were prepared by substituting the appropriate intermediate substituted 5,6,7,8-tetrahydroimidazo[1,2-a]pyrazine (preparations of which are described above) and benzoyl chloride for the 2-(trifluoromethyl)-5,6,7,8-tetrahydroimidazo[1,2-a]pyrazine and 2-chloro-3-(trifluoromethyl)benzoyl chloride used in the above procedure respectively. All of the benzoyl chlorides used are available from commercial sources or can be prepared using routes described previously in the chemical literature. The compounds could be prepared as the free base or isolated using standard procedures (e.g. see example 17) as acid salts e.g. HCl salt.

TABLE 1

| Example no. | Intermediate | Chemical name | [M + H]+ | Retention time (mins) |
|---|---|---|---|---|
| E4 | 3 | 7-{[2-chloro-3-(trifluoromethyl)phenyl]carbonyl}-3-phenyl-5,6,7,8-tetrahydroimidazo[1,2-a]pyrazine hydrochloride | 406, 408 | 1.76 (5 min method) |
| E5 | 3 | 7-[(2,4-dichlorophenyl)carbonyl]-3-phenyl-5,6,7,8-tetrahydroimidazo[1,2-a]pyrazine hydrochloridea]pyrazine hydrochloride | 371, 373 | 0.83 (2 min method) |
| E6 | 5 | 7-{[2-chloro-3-(trifluoromethyl)phenyl]carbonyl}-2-ethyl-5,6,7,8-tetrahydroimidazo[1,2-a]pyrazine | 358, 360 | 1.34 (5 min method) |

TABLE 1-continued

| Example no. | Intermediate | Chemical name | [M + H]⁺ | Retention time (mins) |
|---|---|---|---|---|
| E7 | 5 | 7-[(2,4-dichlorophenyl)carbonyl]-2-ethyl-5,6,7,8-tetrahydroimidazo[1,2-a]pyrazine | 324, 326, 328 | 1.24 (5 min method) |
| E8 | 3 | 7-[(2-chlorophenyl)carbonyl]-3-phenyl-5,6,7,8-tetrahydroimidazo[1,2-a]pyrazine hydrochloride | 356, 358 | 1.52 (5 min method) |
| E9 | 3 | 7-[(2,3-dichlorophenyl)carbonyl]-3-phenyl-5,6,7,8-tetrahydroimidazo[1,2-a]pyrazine hydrochloride | 372, 374, 376 | 1.66 (5 min method) |
| E10 | 3 | 7-[(2-chloro-4-fluorophenyl)carbonyl]-3-phenyl-5,6,7,8-tetrahydroimidazo[1,2-a]pyrazine hydrochloride | 356, 358 | 1.52 (5 min method) |

TABLE 1-continued

| Example no. | Intermediate | Chemical name | [M + H]⁺ | Retention time (mins) |
|---|---|---|---|---|
| E11 | 6 | 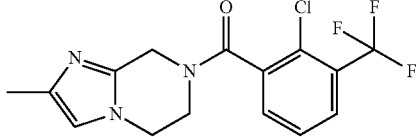 [SMILES: Cc1cn2c(n1)CN(C(=O)c1cccc(C(F)(F)F)c1Cl)CC2]<br>7-{[2-chloro-3-(trifluoromethyl)phenyl]carbonyl}-2-methyl-5,6,7,8-tetrahydroimidazo[1,2-a]pyrazine | 343.95 | 0.68 (2 min method) |
| E12 | 6 | 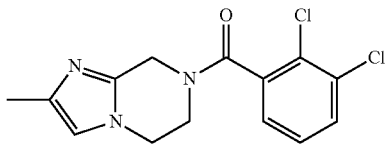 [SMILES: Cc1cn2c(n1)CN(C(=O)c1cccc(Cl)c1Cl)CC2]<br>7-[(2,3-dichlorophenyl)carbonyl]-2-methyl-5,6,7,8-tetrahydroimidazo[1,2-a]pyrazine | 310, 312, 314 | 0.62 (2 min method) |
| E13 | 7 | 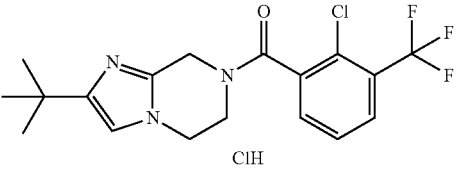 [SMILES: CC(C)(C)c1cn2c(n1)CN(C(=O)c1cccc(C(F)(F)F)c1Cl)CC2 ; Cl]<br>7-{[2-chloro-3-(trifluoromethyl)phenyl]carbonyl}-2-(1,1-dimethylethyl)-5,6,7,8-tetrahydroimidazo[1,2-a]pyrazine hydrochloride | 386 | 1.53 (5 min method) |
| E14 | 8 | 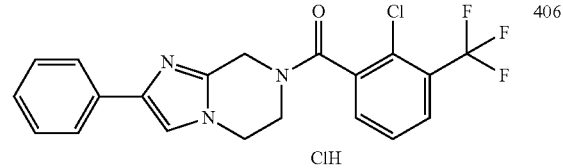<br>7-{[2-chloro-3-(trifluoromethyl)phenyl]carbonyl}-2-phenyl-5,6,7,8-tetrahydroimidazo[1,2-a]pyrazine hydrochloride | 406 | 1.95 (5 min method) |
| E15 | 8 | 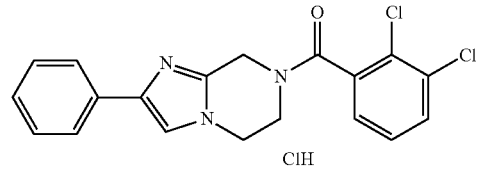 [SMILES: O=C(c1cccc(Cl)c1Cl)N1CCn2cc(-c3ccccc3)nc2C1 ; Cl]<br>7-[(2,3-dichlorophenyl)carbonyl]-2-phenyl-5,6,7,8-tetrahydroimidazo[1,2-a]pyrazine hydrochloride | 372 | 1.79 (5 min method) |

TABLE 1-continued

| Example no. | Intermediate | Chemical name | [M + H]+ | Retention time (mins) |
|---|---|---|---|---|
| E16 | 9 | a hydrochloride (n•HCl) salt of 7-{[2-chloro-3-(trifluoromethyl)phenyl]carbonyl}-3-(2-pyridinyl)-5,6,7,8-tetrahydroimidazo[1,2-a]pyrazine | 407, 409 | 0.81 (2 min method) |

Example 97-[(2,3-Dichlorophenyl)carbonyl]-3-phenyl-5,6,7,8-tetrahydroimidazo[1,2-a]pyrazine hydrochloride (E9)

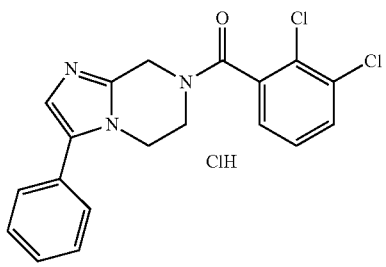 [SMILES: O=C(c1cccc(Cl)c1Cl)N1CCn2c(-c3ccccc3)cnc2C1 ; Cl]

A solution of 4-[(2,3-dichlorophenyl)carbonyl]-2-piperazinone (0.250 g, 0.915 mmol, Intermediate 10) in dry dichloromethane (DCM) (2 mL) was stirred at room temperature under an atmosphere of argon. The mixture was stirred for 2 hours at room temperature after which time 2-amino-1-phenylethanone (0.136 g, 1.007 mmol) monohydrochloride salt and DIPEA (0.176 mL, 1.007 mmol) were added to the stirred solution. The resulting solution was stirred for a further 2 hours at room temperature. After this time, the solution was concentrated under reduced pressure and the residue redissolved in n-butanol (2.000 mL). The resulting solution was heated at reflux (unsure of time, reaction set up to run overnight, hotplate off in the morning due to power cut). Solvent was removed under reduced pressure. The residue was dissolved in DCM (approx. 50 mL) and the organics were washed with brine. The organics were dried over magnesium sulphate, filtered and concentrated under reduced pressure to give a brown coloured oil. The oil was chromatographed [SiO2 eluting with 0-5% (2M NH3 in MeOH) in DCM]. The residue was further purified using mass-directed automated preparative HPLC (high pH method) to give the product as an off-white coloured solid. The solid was dissolved in DCM (approx. 2 ml) and treated with HCl in diethyl ether (1 M, 0.27 ml). The solvent was removed under reduced pressure to give 7-[(2,3-dichlorophenyl)carbonyl]-3-phenyl-5,6,7,8-tetrahydroimidazo[1,2-a]pyrazine (0.092 mg, 0.225 mmol, 24.59% yield).

LC/MS [M+H]+=371.96, 374.99, retention time=0.83 minutes (2 minute method).

Example 17 3-Phenyl-7-[(2,4,6-trichlorophenyl)carbonyl]-5,6,7,8-tetrahydroimidazo[1,2-a]pyrazine hydrochloride (E17)

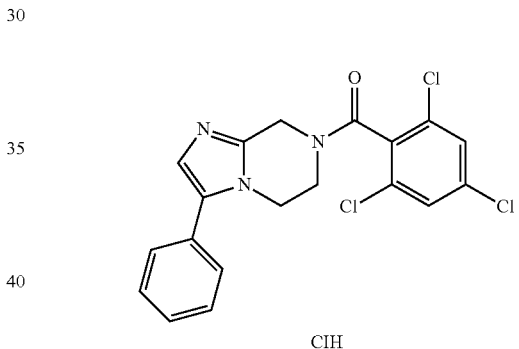

2,4,6-Trichlorobenzoic acid (0.169 g, 0.750 mmol), EDC (0.144 g, 0.750 mmol) and 1-hydroxybenztriazole (0.115 g, 0.750 mmol) were stirred in dichloromethane (DCM) (5 mL) for 15 minutes. 3-Phenyl-5,6,7,8-tetrahydroimidazo[1,2-a]pyrazine (100 mg, 0.5 mmol, Intermediate 3) and diisopropylethylamine (0.175 mL, 1.000 mmol) were added and the solution stirred at room temperature for 16 hr. The mixture was diluted with DCM (50 ml) and washed with saturated sodium bicarbonate (25 ml), water (3×25 ml), brine, dried over anhydrous sodium sulfate and concentrated to a crude oil. The crude oil was twice purified by mass-directed automated preparative HPLC to afford an oil. The purified product was dissolved in dichloromethane (3 ml) and treated with 4N HCl in dioxane (500 uL). The solvents were removed in vacuo and the solid tritruated with diethyl ether to afford product 3-phenyl-7-[(2,4,6-trichlorophenyl)carbonyl]-5,6,7,8-tetrahydroimidazo[1,2-a]pyrazine hydrochloride (0.018 g, 0.041 mmol, 8.12% yield)

LC/MS [M+H]+=406, 408, retention time=1.78 minutes (5 minute method).

Example 18 3-Bromo-7-{[2-chloro-3-(trifluoromethyl)phenyl]carbonyl}-5,6,7,8-tetrahydroimidazo[1,2-a]pyrazine hydrochloride (E18)

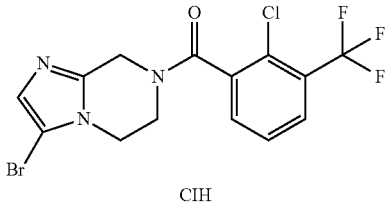 [SMILES: O=C(c1cccc(C(F)(F)F)c1Cl)N1CCn2c(Br)cnc2C1 ; "CIH"]

7-{[2-Chloro-3-(trifluoromethyl)phenyl]carbonyl}-5,6,7,8-tetrahydroimidazo[1,2-a]pyrazine (3.30 g, 10 mmol, Example 1) and NBS (1.869 g, 10.50 mmol) were heated at 110° C. for 2 hr in Toluene (50 ml) and N,N-dimethylformamide (DMF) (10 ml). The mixture was cooled and concentrated in vacuo. The residue was partitioned between ethyl acetate (100 ml) and water (100 ml). The aqueous phase was extracted with ethyl acetate (100 ml). Very bad emulsions were obtained that did not clear using brine, filteration or saturation with salt. Repeated extractions with ethyl acetate (×10) and treatment of the organic extracts with anhydrous sodium sulfate removed the water. The solvents were concentrated in vacuo, and the residue dissolved in chloroform (500 mL), dried over anhydrous sodium sulfate and concentrated to an oil. The crude oil was purified by flash chromatography (Biotage SP4, 40+M, eluting with a 0-100% gradient of [10% 2M $NH_3$/MeOH in DCM]/DCM) to afford product 3-bromo-7-{[2-chloro-3-(trifluoromethyl)phenyl]carbonyl}-5,6,7,8-tetrahydroimidazo[1,2-a]pyrazine (3.1 g, 7.59 mmol, 76% yield), as a beige foam. A 0.180 g sample of this material was further purified by mass-directed automated preparative HPLC and then dissolved in dichloromethane (5 ml) and treated with 4N HCl in dioxane (0.5 ml). The solvents were removed in vacuo and the resulting solid tritruated in diethyl ether to afford 3-bromo-7-{[2-chloro-3-(trifluoromethyl)phenyl]carbonyl}-5,6,7,8-tetrahydroimidazo[1,2-a]pyrazine hydrochloride (0.095 g, 0.213 mmol, 2.135% yield).

LC/MS [M+H]+=408, 410, retention time=2.05 minutes (5 minute method).

Example 19 3-Bromo-7-{[2-chloro-3-(trifluoromethyl)phenyl]carbonyl}-2-(trifluoromethyl)-5,6,7,8-tetrahydroimidazo[1,2-a]pyrazine (E19)

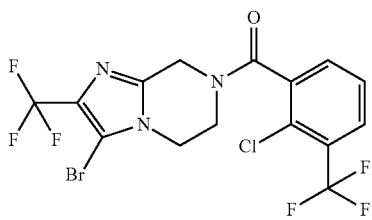

7-{[2-Chloro-3-(trifluoromethyl)phenyl]carbonyl}-2-(trifluoromethyl)-5,6,7,8-tetrahydroimidazo[1,2-a]pyrazine (0.181 g, 0.455 mmol, Example 2) was dissolved in N,N-dimethylformamide (DMF) (2 mL) and treated with N-bromosuccinimide (NBS, 0.097 g, 0.546 mmol). The solution was stirred at room temperature for 16 hr. The mixture was poured onto water (100 ml) containing 1% sodium sulfite (w/w) and extracted into ethyl acetate (3×50 ml). The combined extracts were washed with brine (50 ml), dried over anhydrous sodium sulfate and concentrated to afford crude product (0.323 g). The crude product was purified by mass-directed automated preparative HPLC to afford 3-bromo-7-{[2-chloro-3-(trifluoromethyl)phenyl]carbonyl}-2-(trifluoromethyl)-5,6,7,8-tetrahydroimidazo[1,2-a]pyrazine (0.135 g, 0.283 mmol, 62.2% yield).

LC/MS [M+H]+=476, 478, 480, retention time=2.90 minutes (5 minute method).

Examples 20 and 21 7-{[2-Chloro-3-(trifluoromethyl)phenyl]carbonyl}-2,3-diiodo-5,6,7,8-tetrahydroimidazo[1,2-a]pyrazine and 7-{[2-chloro-3-(trifluoromethyl)phenyl]carbonyl}-3-iodo-5,6,7,8-tetrahydroimidazo[1,2-a]pyrazine (E20 and E21)

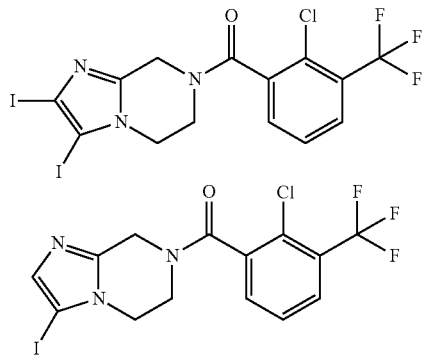

7-{[2-Chloro-3-(trifluoromethyl)phenyl]carbonyl}-5,6,7,8-tetrahydroimidazo[1,2-a]pyrazine (0.989 g, 3 mmol, Example 1) and NIS (0.810 g, 3.60 mmol) were stirred at room temperature for 16 hr in N,N-dimethylformamide (DMF) (8 mL). Further NIS (0.337 g, 1.500 mmol) was added and stirring continued for a further 24 hours. The solvent was removed in vacuo and the residue partitioned between ethyl acetate (100 ml) and water (50 ml) containing 1% sodium sulfite (w/w). The organic phase was washed with 50% brine (3×50 ml), brine (50 ml), dried over anhydrous sodium sulfate and concentrated to a glass that solidified under hexane to afford a yellow solid, (1.61 g). Attempted to purify by flash chromatography (Biotage SP4, 40+M, eluting with 0-100% ethyl acetate/hexane) but this produced no clean fractions. The solvents were removed in vacuo and the residue was purified by mass-directed automated preparative HPLC over 12 injections of 0.100 g each.

Example 20, 7-{[2-chloro-3-(trifluoromethyl)phenyl]carbonyl}-2,3-diiodo-5,6,7,8-tetrahydroimidazo[1,2-a]pyrazine (80 mg, 0.138 mmol, 4.59% yield), was obtained from injections 1-3.

LC/MS [M+H]+=581, 583, retention time=2.77 minutes (5 minute method).

Example 21, 7-{[2-chloro-3-(trifluoromethyl)phenyl]carbonyl}-3-iodo-5,6,7,8-tetrahydroimidazo[1,2-a]pyrazine (584 mg, 1.282 mmol, 42.7% yield), was obtained from injections 1-12 after the solid obtained initially was tritruated in iso-hexane, filtered and then dried.

LC/MS [M+H]+=56, 458, retention time=1.93 minutes (5 minute method).

Example 227-{[2-Chloro-3-(trifluoromethyl)phenyl]carbonyl}-3-(4-fluorophenyl)-5,6,7,8-tetrahydroimidazo[1,2-a]pyrazine hydrochloride (E22)

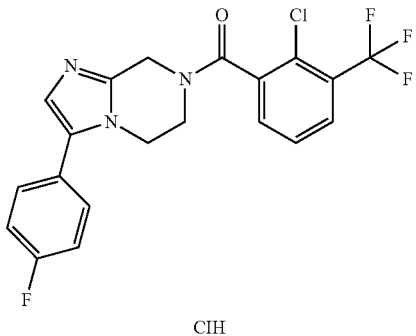 [SMILES: O=C(c1cccc(C(F)(F)F)c1Cl)N1CCn2c(-c3ccc(F)cc3)cnc2C1 ; "CIH"]

3-bromo-7-{[2-chloro-3-(trifluoromethyl)phenyl]carbonyl}-5,6,7,8-tetrahydroimidazo[1,2-a]pyrazine (0.359 g, 0.879 mmol, the free base of Example 18), (4-fluorophenyl)boronic acid (0.135 g, 0.966 mmol), sodium carbonate (0.466 g, 4.39 mmol) and bis(triphenylphosphine)palladium(II) chloride (0.0617 g, 0.088 mmol) were heated at 80° C. for 5 h in water (10.00 mL) and 1,2-dimethoxyethane (DME) (10 mL). The mixture was diluted with ethyl acetate (50 mL), washed with saturated sodium bicarbonate solution, dried by passing through a hydromatric cartridge (Varian, 10 g) and concentrated in vacuo to a crude oil, (0.430 g). The crude oil was purified by flash chromatography (Biotage SP4, 25+M, eluting with a 0-100% gradient of [10% M MeOH/DCM]/DCM to afford crude product (0.312 g), that was further purified by mass-directed automated preparative HPLC to give the free base of the product as a foam. The foam was dissolved in dichloromethane (5 ml) and treated with 4M HCl in dioxane (1 ml). Solvents were removed in vacuo and the solids tritruated with diethyl ether to afford product 7-{[2-chloro-3-(trifluoromethyl)phenyl]carbonyl}-3-(4-fluorophenyl)-5,6,7,8-tetrahydroimidazo[1,2-a]pyrazine (0.154 g, 0.335 mmol, 38.1% yield).

LC/MS [M+H]+=424, 426, retention time=1.84 minutes (5 minute method).

Examples 23 to 25

In a manner analogous to that described for Example 22 above the compounds tabulated below (Table 2) were prepared by substituting the appropriate boronic acid for the (4-fluorophenyl)boronic acid used in the above procedure. The compounds could be prepared as the free base or isolated using standard procedures (e.g. see example 17) as acid salts e.g. HCl salt. All of the boronic acids used are available from commercial sources or can be prepared using routes described previously in the chemical literature.

TABLE 2

| Example no. | Chemical name | [M + H]+ | Retention time (mins) |
|---|---|---|---|
| E23 | a hydrochloride salt (n•HCl) of 7-{[2-chloro-3-(trifluoromethyl)phenyl]carbonyl}-3-(3-pyridinyl)-5,6,7,8-tetrahydroimidazo[1,2-a]pyrazine | 407, 409 | 1.45 (5 min method) |
| E24 | 3-[2-chloro-3-(trifluoromethyl)phenyl]-7-{[2-chloro-3-(trifluoromethyl)phenyl]carbonyl}-5,6,7,8-tetrahydroimidazo[1,2-a]pyrazine hydrochloride | 508, 510 | 2.35 (5 min method) |

TABLE 2-continued

| Example no. | Chemical name | [M + H]⁺ | Retention time (mins) |
|---|---|---|---|
| E25 | 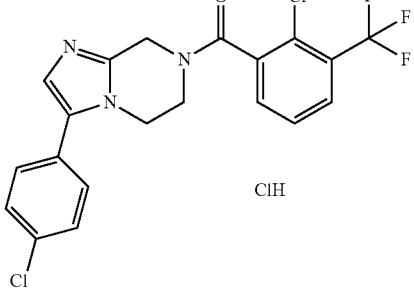<br>3-(4-chlorophenyl)-7-{[2-chloro-3-(trifluoromethyl)phenyl]carbonyl}-5,6,7,8-tetrahydroimidazo[1,2-a]pyrazine hydrochloride | 440, 442, 444 | 2.06 (5 min method) |

Example 26 7-{[2-Chloro-3-(trifluoromethyl)phenyl]carbonyl}-3-phenyl-2-(trifluoromethyl)-5,6,7,8-tetrahydroimidazo[1,2-a]pyrazine (E26)

Example 27 7-{[2-Chloro-3-(trifluoromethyl)phenyl]carbonyl}-3-methyl-5,6,7,8-tetrahydroimidazo[1,2-a]pyrazine hydrochloride (E27)

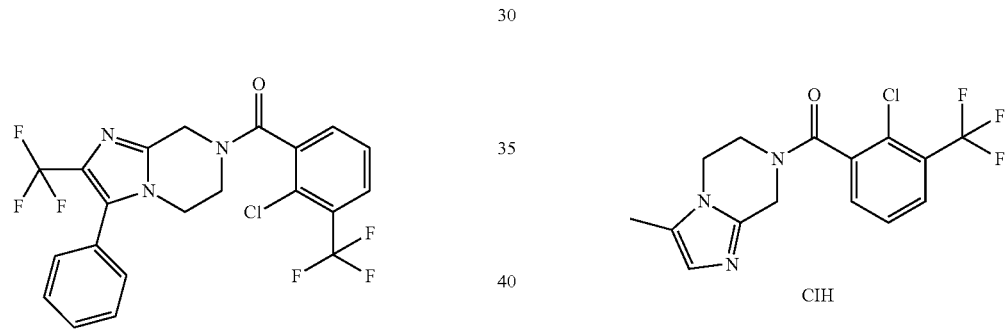

3-bromo-7-{[2-chloro-3-(trifluoromethyl)phenyl]carbonyl}-2-(trifluoromethyl)-5,6,7,8-tetrahydroimidazo[1,2-a]pyrazine (0.100 g, 0.210 mmol, Example 19), phenylboronic acid (0.0384 g, 0.315 mmol), bis(triphenylphosphine)palladium(II)chloride (0.0147 g, 0.021 mmol) and 1,2-dimethoxyethane (DME) (5 mL) were heated at 100° C. for 4 h in a 1,2-dimethoxyethane (DME) (5 mL)/water (5.00 mL) mixture. The reaction mixture was diluted with ethyl acetate (50 ml) and extracted with ethyl acetate (2×50 ml). The combined extracts were washed with brine and dried through a hydromatrix cartridge (Varian, 10 g). The filtrate was concentrated to an oil that was purified by mass-directed automated preparative HPLC to afford, after trituration in iso-hexane, 7-{[2-chloro-3-(trifluoromethyl)phenyl]carbonyl}-3-phenyl-2-(trifluoromethyl)-5,6,7,8-tetrahydroimidazo[1,2-a]pyrazine (0.051 g, 0.108 mmol, 51.3% yield).

LC/MS [M+H]+=474, 476, retention time=3.04 minutes (5 minute method).

3-bromo-7-{[2-chloro-3-(trifluoromethyl)phenyl]carbonyl}-5,6,7,8-tetrahydroimidazo[1,2-a]pyrazine (0.204 g, 0.5 mmol, the free base of Example 18) was dissolved in 1,4-dioxane (3 mL), trimethylboroxine (0.084 mL, 0.600 mmol), potassium carbonate (0.104 g, 0.750 mmol) and tetrakis (triphenylphosphine) palladium (0) (0.058 g, 0.050 mmol) were added. The mixture was heated at 110° C. for 16 h. The mixture was poured on to water (100 ml) and extracted in to ethyl acetate (3×50 ml). Combined extracts were washed with water (3×50 ml), brine (50 ml), dried over anhydrous sodium sulfate and concentrated to a dark oil, (0.336 g). The oil was purified by MDAP to afford a glass, which was dissolved in dichloromethane (5 ml) and treated with 4N HCl in dioxane (1 mL). The solvents were removed in vacuo and the resulting solid triturated in diethyl ether to afford 7-{[2-chloro-3-(trifluoromethyl)phenyl]carbonyl}-3-methyl-5,6,7,8-tetrahydroimidazo[1,2-a]pyrazine hydrochloride (0.050 g, 0.132 mmol, 26.3% yield).

LC/MS [M+H]+=344, 346, retention time=1.24 minutes (5 minute method).

Example 28 7-{[2-Chloro-3-(trifluoromethyl)phenyl]carbonyl}-3-(2-methylphenyl)-5,6,7,8-tetrahydroimidazo[1,2-a]pyrazine hydrochloride (E28)

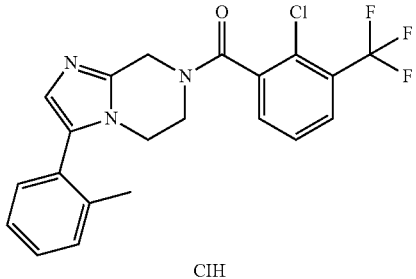 [SMILES: Cc1ccccc1-c1cnc2n1CCN(C(=O)c1cccc(C(F)(F)F)c1Cl)C2 ; "CIH"]

CIH

7-{[2-Chloro-3-(trifluoromethyl)phenyl]carbonyl}-5,6,7,8-tetrahydroimidazo[1,2-a]pyrazine (0.330 g, 1 mmol, Example 1), 1-bromo-2-methylbenzene (0.132 mL, 1.100 mmol), palladium(II)acetate (0.011 g, 0.050 mmol), triphenylphosphine (0.026 g, 0.100 mmol) and cesium carbonate (0.342 g, 1.050 mmol) were suspended in 1,4-dioxane (5 ml) under argon. The mixture was degassed 3 times and heated at 90° C. for 16 h. The solvent was removed in vacuo and the residue partitioned between ethyl acetate (50 ml) and water (50 ml). The aqueous phase was extracted with ethyl acetate (2×50 ml), the combined organic extracts were washed with water (3×50 ml), brine (50 ml) dried over anhydrous sodium sulfate and concentrated to a crude oil. The crude oil was purified by mass-directed automated preparative HPLC to afford the free base that was dissolved in dichloromethane (5 ml) and treated with 4N HCl in dioxane. The solvents were removed in vacuo and the solid tritruated with diethyl ether to afford 7-{[2-chloro-3-(trifluoromethyl)phenyl]carbonyl}-3-(2-methylphenyl)-5,6,7,8-tetrahydroimidazo[1,2-a]pyrazine (0.027 g, 0.059 mmol, 5.92% yield).

LC/MS [M+H]+=420, 422, retention time=1.85 minutes (5 minute method).

Example 29 2,3-dichloro-7-[(2,4-dichlorophenyl)carbonyl]-5,6,7,8-tetrahydroimidazo[1,2-a]pyrazine (E29)

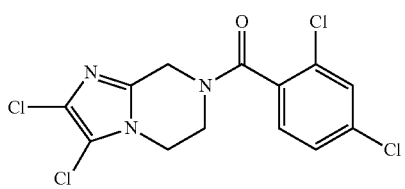 [SMILES: O=C(c1ccc(Cl)cc1Cl)N1CCn2c(nc(Cl)c2Cl)C1]

3-Chloro-7-[(2,4-dichlorophenyl)carbonyl]-5,6,7,8-tetrahydroimidazo[1,2-a]pyrazine (E44) (300 mg, 0.907 mmol) and NCS (133 mg, 0.998 mmol) were stirred at RT for 16 h in N,N-dimethylformamide (DMF) (2 mL). Solvents were removed in vacuo and the residue was purified by MDAP to afford desired product in 218 mg.

LC/MS=363/365/367 (M+H)+, retention time=1.04 minutes (2 minute method).

Example 30 3-Bromo-7-[(2-chloro-4-fluorophenyl)carbonyl]-5,6,7,8-tetrahydroimidazo[1,2-a]pyrazine (E30)

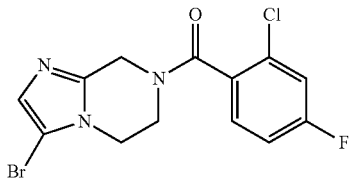

7-[(2-Chloro-4-fluorophenyl)carbonyl]-5,6,7,8-tetrahydroimidazo[1,2-a]pyrazine (I21) (300 mg, 1.073 mmol) was dissolved in N,N-dimethylformamide (DMF) (2 mL) and treated with NBS (200 mg, 1.126 mmol). The solution was stirred at 25° C. for 16 h. The solvents were removed in vacuo and the residue purified by MDAP (High pH method) to afford desired product in 210 mg.

LC/MS=358/360/362 (M+H)+, retention time=0.74 minutes (2 minute method).

Example 31 7-{[2-Chloro-3-(trifluoromethyl)phenyl]carbonyl}-3-(5-fluoro-2-pyridinyl)-5,6,7,8-tetrahydroimidazo[1,2-a]pyrazine (E31)

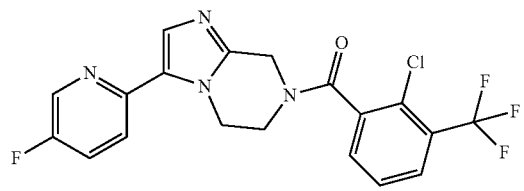 [SMILES: O=C(c1cccc(C(F)(F)F)c1Cl)N1CCn2c(-c3ccc(F)cn3)cnc2C1]

7-{[2-Chloro-3-(trifluoromethyl)phenyl]carbonyl}-3-(5-fluoro-2-pyridinyl)-5,6,7,8-tetrahydroimidazo[1,2-a]pyrazine (E31) can be prepared by using either of the following 2 routes:

1) A mixture of 3-bromo-7-{[2-chloro-3-(trifluoromethyl)phenyl]carbonyl}-5,6,7,8-tetrahydroimidazo[1,2-a]pyrazine (E18) (62 mg, 0.140 mmol), 5-fluoro-2-(4,4,5,5-tetramethyl-1,3,2-dioxaborolan-2-yl)pyridine (78 mg, 0.349 mmol), copper(I) chloride (13.82 mg, 0.140 mmol), cesium carbonate (136 mg, 0.419 mmol), palladium(II) acetate (1.567 mg, 6.98 µmol), and DPPF (7.74 mg, 0.014 mmol) in dry N,N-dimethylformamide (DMF) (1396 µl) was degassed by bubbling a stream of argon through the mixture (for a total of 10 minutes) the mixture was subsequently heated to 100° C. for 3 hours. After this time, the solution was diluted with EtOAc (approx. 30 ml) and washed with water (2× approx. 10 ml). The organics were dried over MgSO₄, filtered and concentrated under reduced pressure to give a brown coloured oil. The residue was chromatographed [SiO₂, MeOH in DCM 0-5%] to give an off white coloured solid of desired product in 12 mg.

LCMS [M+H]+ 424.92 @0.89 min (2 minute run).

2) A mixture of 3-bromo-7-{[2-chloro-3-(trifluoromethyl)phenyl]carbonyl}-5,6,7,8-tetrahydroimidazo[1,2-a]pyrazine (E18) (120 mg, 0.294 mmol) and 5-fluoro-2-(trimethylstannanyl)pyridine (I16) (114 mg, 0.441 mmol) in anhydrous 1,4-dioxane (979 μl) was degassed by sonication under a flow of argon for 10 minutes before palladium tetrakis (50.9 mg, 0.044 mmol) was added and it was exposed to microwaves at 140° C. for 1 hour and then heated for a further hour. Palladium tetrakis (50.9 mg, 0.044 mmol) was added and the reaction mixture was heated for a further hour. LCMS showed it went to completion (no mass ion for starting bromide). It was applied to a 5 g SCX, washed with MeOH and eluted with 2M NH$_3$ in MeOH. The material isolated was impure and purified by flash chromatography (Biotage SP4, 12+M cartridge) with a gradient of MeOH 0 to 5% in DCM and the resulting material (70 mg) was further purified by MDAP to yield the desired product in 15 mg as a white solid.

LC/MS: (M+H)$^+$=425, retention time=0.81 minutes (2 minutes run).

Example 32 3-Bromo-7-[(2-chloro-4-fluorophenyl)carbonyl]-2-(trifluoromethyl)-5,6,7,8-tetrahydroimidazo[1,2-a]pyrazine (E32)

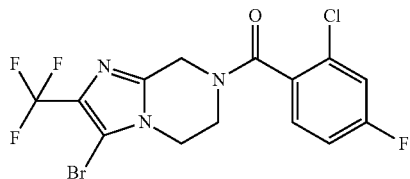 [SMILES: O=C(c1ccc(F)cc1Cl)N1CCn2c(nc(C(F)(F)F)c2Br)C1]

7-{[2-Chloro-3-(trifluoromethyl)phenyl]carbonyl}-2-(trifluoromethyl)-5,6,7,8-tetrahydroimidazo[1,2-a]pyrazine (I22) (181 mg, 0.455 mmol) was dissolved in N,N-dimethylformamide (DMF) (2 mL) and treated with NBS (97 mg, 0.546 mmol). The solution was stirred at RT for 16 h. The mixture was poured on to water (100 ml) containing 1% sodium sulfite (w/w) and extrated in to ethyl acetate (3×50 ml). Combined extracts were washed with brine (50 ml), dried over anhydrous sodium sulfate and concentrated to afford crude product. The crude product was purified by MDAP to afford desired product in 135 mg.

LC/MS=476/478/480 (M+H)$^+$, retention time=2.90 minutes (5 minute).

Example 33 3-Bromo-2-chloro-7-{[2-chloro-3-(trifluoromethyl)phenyl]carbonyl}-5,6,7,8-tetrahydroimidazo[1,2-a]pyrazine (E33)

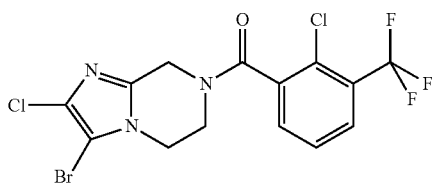 [SMILES: O=C(c1cccc(C(F)(F)F)c1Cl)N1CCn2c(nc(Cl)c2Br)C1]

3-Bromo-7-{[2-chloro-3-(trifluoromethyl)phenyl]carbonyl}-5,6,7,8-tetrahydroimidazo[1,2-a]pyrazine (E18) (409 mg, 1 mmol) was dissolved in N,N-dimethylformamide (DMF) (5 mL) and NCS (147 mg, 1.100 mmol) was added. The solution was stirred at RT for 24 h. Solvents were removed in vacuo and the residue was purified by flash chromatography (Isolera, 25 g, 0-100% ethyl acetate/iso-hexane) to afford crude product. This was further purified by MDAP to afford desired product in 215 mg.

LC/MS=442/444/446 (M+H)+, retention time=1.06 minutes (2 minute method).

Example 34 2-Bromo-7-{[2-chloro-3-(trifluoromethyl)phenyl]carbonyl}-3-(4-fluorophenyl)-5,6,7,8-tetrahydroimidazo[1,2-a]pyrazine (E34)

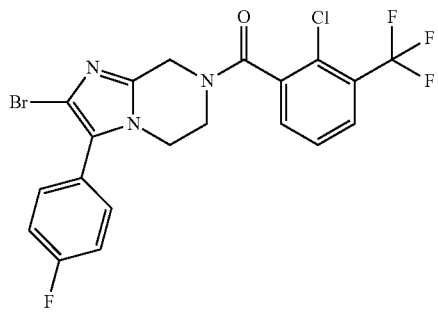 [SMILES: O=C(c1cccc(C(F)(F)F)c1Cl)N1CCn2c(nc(Br)c2-c2ccc(F)cc2)C1]

7-{[2-Chloro-3-(trifluoromethyl)phenyl]carbonyl}-3-(4-fluorophenyl)-5,6,7,8-tetrahydroimidazo[1,2-a]pyrazine (E22) (424 mg, 1 mmol) was dissolved in N,N-dimethylformamide (DMF) (5 mL) to which NBS (196 mg, 1.100 mmol) was added. The solution was stirred at RT for 24 h and solvents were removed in vacuo. The residue was purified by flash chromatography (Isolera, 25 g, 0-100% ethyl acetate/iso-hexane) to afford a crude product. This was further purified by MDAP to afford clean, desired product in 230 mg.

LC/MS=502/504/506 (M+H)$^+$, retention time=1.15 minutes (2 minute method).

Example 35 7-{[2-chloro-3-(trifluoromethyl)phenyl]carbonyl}-3-(4-fluorophenyl)-2-(trifluoromethyl)-5,6,7,8-tetrahydroimidazo[1,2-a]pyrazine (E35)

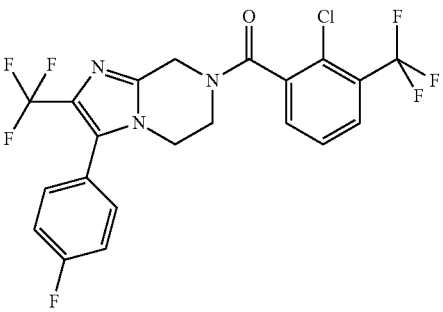 [SMILES: O=C(c1cccc(C(F)(F)F)c1Cl)N1CCn2c(nc(C(F)(F)F)c2-c2ccc(F)cc2)C1]

3-(4-Fluorophenyl)-2-(trifluoromethyl)-5,6,7,8-tetrahydroimidazo[1,2-a]pyrazine (I14) (285 mg, 1 mmol) and diethylaminomethyl polystyrene (1000 mg, 3.20 mmol) were slurried in dichloromethane (DCM) (10 mL) and treated with 2-chloro-3-(trifluoromethyl)benzoyl chloride (267 mg, 1.100 mmol). The slurry was stirred at RT for 24 h, whereupon the resin was filtered and washed with dichloromethane (20 mL). The filtrate was concentrated in vacuo to afford crude product. The product was purified by flash chromatography (Isolera, 10 g, 0-100% ethyl acetate/iso-hexane) to afford product in 428 mg.

LC/MS=492/494 (M+H)+, retention time=1.18 minutes (2 minute method).

Example 367-[(2,4-dichlorophenyl)carbonyl]-3-(4-fluorophenyl)-2-(trifluoromethyl)-5,6,7,8-tetrahydroimidazo[1,2-a]pyrazine (E36)

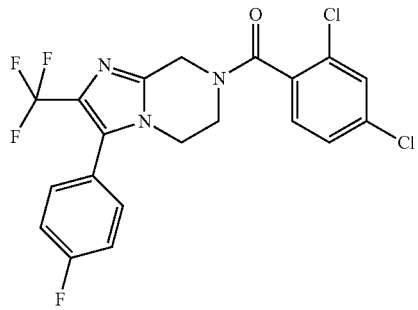 [SMILES: O=C(c1ccc(Cl)cc1Cl)N1CCn2c(nc(C(F)(F)F)c2-c2ccc(F)cc2)C1]

3-(4-Fluorophenyl)-2-(trifluoromethyl)-5,6,7,8-tetrahydroimidazo[1,2-a]pyrazine (I14) (285 mg, 1 mmol) and diethylaminomethyl polystyrene (1.000 g, 3.20 mmol) were slurried in dichloromethane (DCM) (10 mL) and treated with 2,4-dichlorobenzoyl chloride (0.154 mL, 1.100 mmol). The slurry was stirred at RT for 24 h, whereupon the resin was filtered and washed with dichloromethane (20 mL). The filtrate was concentrated in vacuo to afford crude product. The product was purified by flash chromatography (Isolera, 10 g, 0-100% ethyl acetate/iso-hexane) to afford product in 402 mg. This was further purified by flash chromatography (Isolera, 10 g, 0-100% ethyl acetate/iso-hexane) to afford product in 303 mg.

LC/MS=456/458/460 (M+H)+, retention time=1.17 minutes (2 minute method).

Example 377-[(2-chloro-4-fluorophenyl)carbonyl]-3-(2-pyrazinyl)-5,6,7,8-tetrahydroimidazo[1,2-a]pyrazine (E37)

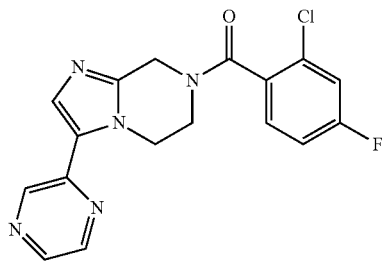

3-Bromo-7-[(2-chloro-4-fluorophenyl)carbonyl]-5,6,7,8-tetrahydroimidazo[1,2-a]pyrazine (E30) (108 mg, 0.301 mmol) and 2-(tributylstannyl)pyrazine (0.142 mL, 0.452 mmol, commercially available from e.g. Sigma-Aldrich, Fluorochem or Apollo) were suspended in 1,4-dioxane (1 mL), degassed for 5 mins before adding palladium tetrakis (52.2 mg, 0.045 mmol) and heating under microwave conditions for 120 mins at 140° C. until no brominated starting materials were observed by LCMS. Solvent evaporated, residue purified on 12+M SP4 column, eluting with iso-Hex (3CV) to 100% EtOAc over 20 CV. Then DCM (3CV) to 10% 2M NH$_3$/MeOH in DCM over 12 CV. Solvent evaporated to afford a yellow gum which was further purified by MDAP, desired fractions isolated and solvent evaporated to afford an off white foam of desired product in 43 mg.

LCMS [M+H] 357.86/359.85 @0.60 min (2 min run).

Example 387-{[2-chloro-3-(trifluoromethyl)phenyl]carbonyl}-3-(2-pyrazinyl)-5,6,7,8-tetrahydroimidazo[1,2-a]pyrazine (E38)

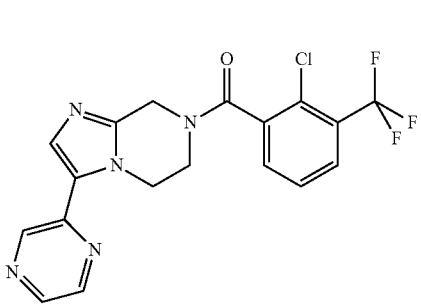 [SMILES: O=C(c1cccc(C(F)(F)F)c1Cl)N1CCn2c(-c3cnccn3)cnc2C1]

3-Bromo-7-{[2-chloro-3-(trifluoromethyl)phenyl]carbonyl}-5,6,7,8-tetrahydroimidazo[1,2-a]pyrazine (I15) (125 mg, 0.306 mmol) and 2-(tributylstannyl)pyrazine (0.145 mL, 0.459 mmol) were suspended in 1,4-dioxane (1 mL), degassed for 5 mins before adding palladium tetrakis (17.68 mg, 0.015 mmol) and heating under microwave conditions for 180 mins at 140° C. Solvent removed by evaporation, residue purified on 12+M SP4 column, eluting with DCM (3CV) to 10% 2M NH3/MeOH in DCM over 12 CV. The desired fractions were collected and the solvent evaporated to afford a yellow gum, which was further purified by MDAP. Fractions combined and solvent evaporated to afford a yellow foam of desired product in 45 mg.

LCMS: m/z 407.95/409.89 (M+H) @0.74 min (2 min run).

Example 397-{[2-chloro-3-(trifluoromethyl)phenyl]carbonyl}-3-(1,3-thiazol-2-yl)-5,6,7,8-tetrahydroimidazo[1,2-a]pyrazine (E39)

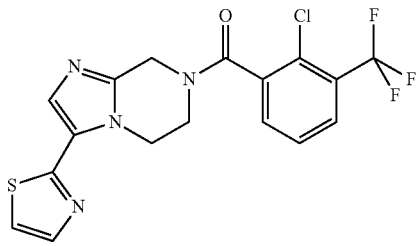 [SMILES: O=C(c1cccc(C(F)(F)F)c1Cl)N1CCn2c(-c3nccs3)cnc2C1]

3-Bromo-7-{[2-chloro-3-(trifluoromethyl)phenyl]carbonyl}-5,6,7,8-tetrahydroimidazo[1,2-a]pyrazine (I15) (209 mg, 0.512 mmol) and 2-(tributylstannanyl)-1,3-thiazole (0.241 mL, 0.767 mmol, commercially available from e.g. Sigma-Aldrich, Apollo or Frontier Scientific) were suspended in 1,4-dioxane (2.5 mL), degassed for 5 mins before adding palladium tetrakis (29.6 mg, 0.026 mmol) and heating under microwave conditions for 60 mins at 140° C. Solvent removed by evaporation to afford a black gum, residue purified on 12+M SP4 column, eluting with DCM (3CV) to 10% 2M NH$_3$/MeOH in DCM over 12 CV. The desired fractions were collected and the solvent evaporated to afford a yellow gum, which was further purified by MDAP, Fractions combined and solvent evaporated to afford a colourless gum, dried to afford an off white foam, triturated with Et₂O, compound dissolved, dried again to afford an off white solid of desired product in 111 mg.

LCMS: m/z 413.08 (M+H) @0.87 min (2 min run).

Example 407-[(2-chloro-4-fluorophenyl)carbonyl]-3-(2-pyrazinyl)-5,6,7,8-tetrahydroimidazo[1,2-a]pyrazine (E40)

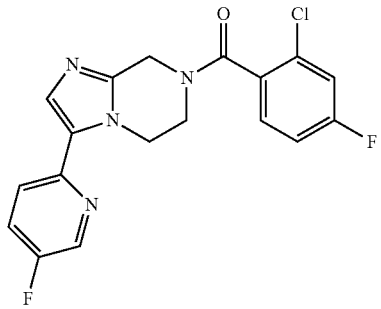 [SMILES: O=C(c1ccc(F)cc1Cl)N1CCn2c(-c3ccc(F)cn3)cnc2C1]

Mixture of 3-bromo-7-[(2-chloro-4-fluorophenyl)carbonyl]-5,6,7,8-tetrahydroimidazo[1,2-a]pyrazine (E30) (120 mg, 0.335 mmol) and 5-fluoro-2-(trimethylstannanyl)pyridine (I16) (130 mg, 0.502 mmol) in anhydrous 1,4-dioxane (1115 μl) was degassed by sonication under a flow of argon for 10 minutes before palladium tetrakis (58.0 mg, 0.050 mmol) was added and it was exposed to microwaves at 140° C. for 2 hours. Palladium tetrakis (58.0 mg, 0.050 mmol) was added and the reaction mixture was heated for a further hour. The crude product was applied to a 5 g SCX, washed with MeOH and eluted with 2M NH₃ in MeOH. The resulting material was then purified by MDAP to afford the desired product in 17 mg as an off-white solid.

LC/MS: (M+H)⁺=375, retention time=0.69 minutes (2 minutes run).

Example 417-{[2-chloro-3-(trifluoromethyl)phenyl]carbonyl}-3-(2-pyrimidinyl)-5,6,7,8-tetrahydroimidazo[1,2-a]pyrazine (E41)

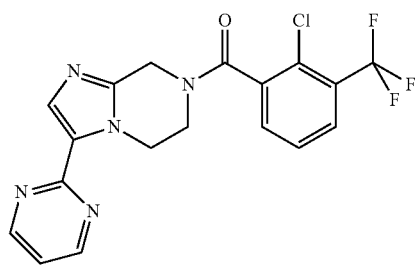 [SMILES: O=C(c1cccc(C(F)(F)F)c1Cl)N1CCn2c(-c3ncccn3)cnc2C1]

3-Bromo-7-{[2-chloro-3-(trifluoromethyl)phenyl]carbonyl}-5,6,7,8-tetrahydroimidazo[1,2-a]pyrazine (I15) (200 mg, 0.489 mmol) and 2-(tributylstannanyl)pyrimidine (271 mg, 0.734 mmol, commercially available from e.g. Matrix Scientific, Anichem or Frontier Scientific) were suspended in 1,4-dioxane (2 mL), degassed for 5 mins before adding palladium tetrakis (28.3 mg, 0.024 mmol) and heating under microwave conditions for 180 mins at 140° C. More 2-(tributylstannanyl)pyrimidine (271 mg, 0.734 mmol) was added and palladium tetrakis (28.3 mg, 0.024 mmol) and the reaction mixture was heated in the microwave for a further 150 mins then worked up. Solvent evaporated to afford a brown gum of crude product. Purified on a 25+M column eluting with DCM (3CV) to 10% 2M NH₃/MeOH in DCM over 20 CV. Desired fractions collected, solvent evaporated to afford a yellow gum. Further purification required by MDAP. Desired fractions isolated and solvent evaporated to afford a colourless gum of desired product in 11 mg as an off white solid.

LCMS: m/z 408.15/410.15 (M+H) @0.78 min (2 min run).

Example 427-{[2-chloro-3-(trifluoromethyl)phenyl]carbonyl}-3-(1,3-thiazol-4-yl)-5,6,7,8-tetrahydroimidazo[1,2-a]pyrazine (E42)

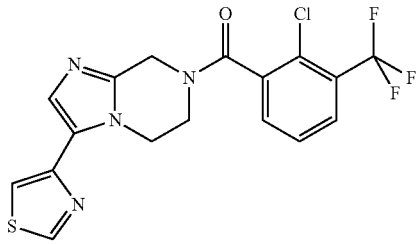 [SMILES: O=C(c1cccc(C(F)(F)F)c1Cl)N1CCn2c(-c3cscn3)cnc2C1]

3-Bromo-7-{[2-chloro-3-(trifluoromethyl)phenyl]carbonyl}-5,6,7,8-tetrahydroimidazo[1,2-a]pyrazine (I15) (218 mg, 0.534 mmol) and 4-(tributylstannanyl)-1,3-thiazole (299 mg, 0.800 mmol, commercially available from Apollo, Synthonix or Bepharm) were suspended in 1,4-dioxane (2 mL), degassed for 5 mins before adding palladium tetrakis (30.8 mg, 0.027 mmol) and heating under microwave conditions for 60 mins at 140° C. Solvent removed by evaporation to afford a black gum, residue purified on 25+M SP4 column, eluting with DCM (3CV) to 5% 2M NH₃/MeOH in DCM over 12 CV. Desired fractions collected, solvent evaporated to afford a yellow sticky foam. Further purified by MDAP, fractions combined and solvent evaporated to afford an off white foam, dried overnight at 40° C. to afford the desired product in 138 mg.

LCMS: m/z 413.05/415.05 (M+H) @0.74 min

Example 43 3-chloro-7-{[2-chloro-3-(trifluoromethyl)phenyl]carbonyl}-5,6,7,8-tetrahydroimidazo[1,2-a]pyrazine (E43)

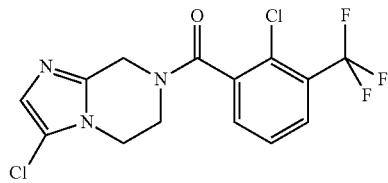 [SMILES: O=C(c1cccc(C(F)(F)F)c1Cl)N1CCn2c(Cl)cnc2C1]

3-Chloro-5,6,7,8-tetrahydroimidazo[1,2-a]pyrazine (I20) (450 mg, 2.86 mmol) and diethylaminomethyl polystyrene (2855 mg, 9.14 mmol) were slurried in dichloromethane (DCM) (10 mL) and treated with 2-chloro-3-(trifluoromethyl)benzoyl chloride (763 mg, 3.14 mmol). The slurry was stirred at RT for 24 h, whereupon the resin was filtered and washed with dichloromethane (20 mL). The filtrate was concentrated in vacuo to afford 911 mg of material that was purified by flash chromatography (Isolera, 10 g, 0-100% ethyl acetate/iso-hexane) to afford a crude product which was further purified by MDAP to afford desired product in 373 mg.

LC/MS=364/366/368 (M+H)+, retention time=0.82 minutes (2 minute method).

Example 44 3-chloro-7-[(2,4-dichlorophenyl)carbonyl]-5,6,7,8-tetrahydroimidazo[1,2-a]pyrazine (E44)

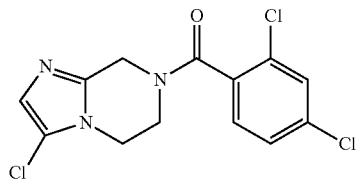 [SMILES: O=C(c1ccc(Cl)cc1Cl)N1CCn2c(Cl)cnc2C1]

3-Chloro-5,6,7,8-tetrahydroimidazo[1,2-a]pyrazine (I20) (450 mg, 2.86 mmol) and diethylaminomethyl polystyrene (2855 mg, 9.14 mmol) were slurried in dichloromethane (DCM) (10 mL) and treated with 2,4-dichlorobenzoyl chloride (0.439 mL, 3.14 mmol). The slurry was stirred at RT for 24 h, whereupon the resin was filtered and washed with dichloromethane (20 mL). The filtrate was concentrated in vacuo to afford crude product. The product was purified by flash chromatography (Isolera, 10 g, 0-100% ethyl acetate/iso-hexane) to afford product then by MDAP (High pH method) to afford clean desired product in 350 mg.

LC/MS=330/332/334 (M+H)+, retention time=0.77 minutes (2 minute method)

Example 45 2,3-dichloro-7-{[2-chloro-3-(trifluoromethyl)phenyl]carbonyl}-5,6,7,8-tetrahydroimidazo[1,2-a]pyrazine (E45)

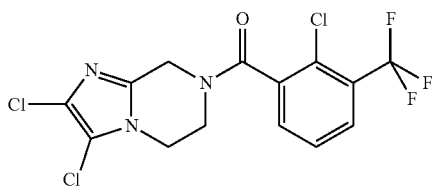 [SMILES: O=C(c1cccc(C(F)(F)F)c1Cl)N1CCn2c(nc(Cl)c2Cl)C1]

3-Chloro-7-{[2-chloro-3-(trifluoromethyl)phenyl]carbonyl}-5,6,7,8-tetrahydroimidazo[1,2-a]pyrazine (E43) (300 mg, 0.824 mmol) and NCS (121 mg, 0.906 mmol) were stirred at RT for 16 h in N,N-dimethylformamide (DMF) (2 mL). Solvents were concentrated in vacuo and the residue purified by MDAP to afford desired product in 145 mg.

LC/MS=398/400/402 (M+H)+, retention time=1.06 minutes (2 minute method).

Mass-Directed Automated HPLC

Where applicable, purification by mass-directed automated HPLC was carried out using the following apparatus and conditions:

Hardware
  Waters 2525 Binary Gradient Module
  Waters 515 Makeup Pump
  Waters Pump Control Module
  Waters 2767 Inject Collect
  Waters Column Fluidics Manager
  Waters 2996 Photodiode Array Detector
  Waters ZQ Mass Spectrometer
  Gilson 202 fraction collector
  Gilson Aspec waste collector
Software
  Waters MassLynx version 4 SP2
Column The columns used are Waters Atlantis, the dimensions of which are 19 mm×100 mm (small scale) and 30 mm×100 mm (large scale). The stationary phase particle size is 5 μm.

Solvents
  A: Aqueous solvent=Water+0.1% Formic Acid
  B: Organic solvent=Acetonitrile+0.1% Formic Acid
  Make up solvent=Methanol:Water 80:20
  Needle rinse solvent=Methanol Methods There are five methods used depending on the analytical retention time of the compound of interest. They have a 13.5-minute runtime, which comprises of a 10-minute gradient followed by a 3.5 minute column flush and re-equilibration step. Large/Small Scale 1.0-1.5=5-30% B
Large/Small Scale 1.5-2.2=15-55% B
Large/Small Scale 2.2-2.9=30-85% B
Large/Small Scale 2.9-3.6=50-99% B
Large/Small Scale 3.6-5.0=80-99% B (in 6 minutes followed by 7.5 minutes flush and re-equilibration)

Flow Rate

All of the above methods have a flow rate of either 20 mls/min (Small Scale) or 40 mls/min (Large Scale).

Liquid Chromatography/Mass Spectrometry

Analysis of the above Examples by Liquid Chromatography/Mass Spectrometry (LC/MS) was carried out using the apparatus and conditions indicated in the methods shown below:

Liquid Chromatography—5 Minute Method:

Formic Acid Generic Analytical HPLC Open Access LC/MS

The HPLC analysis was conducted on a Sunfire C18 column (30 mm×4.6 mm i.d. 3.5 μm packing diameter) at 30 degrees centigrade.

The solvents employed were:
A=0.1% v/v solution of Formic Acid in Water.
B=0.1% v/v solution of Formic Acid in Acetonitrile.

| Time (min) | Flow Rate (ml/min) | % A | % B |
| --- | --- | --- | --- |
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

Liquid Chromatography—2 Minute Method:

Formic Acid Generic Analytical UPLC Open Access LC/MS

The UPLC analysis was conducted on an Acquity UPLC BEH C18 column (2.1 mm×50 mm i.d. 1.7 μm packing diameter) at 40 degrees centigrade.

The solvents employed were:
A=0.1% v/v solution of Formic Acid in Water.
B=0.1% v/v solution of Formic Acid in Acetonitrile.

| Time (min) | Flow Rate (ml/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

Pharmacological Data

Compounds or salts of the invention may be tested for in vitro biological activity at the P2X7 receptor in accordance with the following studies:

Eithidium Accumulation Assay 1

Studies were performed using NaCl assay buffer of the following composition: 140 mM NaCl, 10 mM HEPES [4-(2-hydroxyethyl)-1-piperazine-1-ethanesulfonic acid], 5 mM N-methyl-D-glucamine, 5.6 mM KCl, 10 mM D-glucose, 0.5 mM $CaCl_2$ (pH 7.4).

Human Embryonic Kidney (HEK) 293 cells, stably expressing human recombinant P2X7 receptors, were grown in poly-D-lysine pretreated 96 well plates for 18-24 hours. (The cloning of the human P2X7 receptor is described in U.S. Pat. No. 6,133,434, e.g. see Example 3 therein). The cells were washed twice with 350 μl of the assay buffer, before addition of 50 μl of the assay buffer containing the putative P2X7 receptor antagonist compound. (A small amount of dimethyl sulfoxide, for initially dissolving the compound, is optionally used and present in this 500 test compound sample.) The cells were then incubated at room temperature (19-21° C.) for 30 min before addition of ATP and ethidium (100 μM final assay concentration). The ATP concentration was chosen to be close to the $EC_{80}$ for the receptor type and was 1 mM for studies on the human P2X7 receptor. Incubations were continued for 8 or 16 min and were terminated by addition of 25 μl of 1.3M sucrose containing 4 mM of the P2X7 receptor antagonist Reactive Black 5 (Aldrich). Cellular accumulation of ethidium was determined by measuring fluorescence (excitation wavelength of 530 nm and emission wavelength of 620 nm) from below the plate with a Canberra Packard Fluorocount (14 Station Road, Pangbourne, Reading, Berkshire RG8 7AN, United Kingdom) or a FlexStation II 384 from Molecular Devices (660-665 Eskdale Road, Wokingham, Berkshire RG41 5TS, United Kingdom). Antagonist $pIC_{50}$ values for blocking ATP responses were determined using iterative curve fitting techniques.

Eithidium Accumulation Assay 2

Studies were performed using NaCl assay buffer of the following composition: 140 mM NaCl (8.182 g/liter), 10 mM Hepes Acid (2.383 g/liter), 5 mM KCl (0.4175 g/liter), 10 mM glucose (1.8 g/liter), 1 mM $CaCl_2$ (0.5 ml of 1M solution/liter) and 5 mM N-methyl-D-glucamine (approximately 4.5 ml of 1M solution to adjust pH to 7.4); an Ethidium Bromide solution of the following composition: 395 ul of 10 mg/ml purchased stock into 49.61 mL of NaCl buffer; and an ATP solution of the following composition: 1.56 mL of a 32 mM ATP solution (Na salt prepared in water) to 23.44 ml of the Ethidium Bromide solution.

Human Embryonic Kidney (HEK) 293 cells, stably expressing human recombinant P2X7 receptors, were grown in poly-D-lysine pretreated 96 well plates for 24 hours at 37° C. (The cloning of the human P2X7 receptor is described in U.S. Pat. No. 6,133,434, e.g. see Example 3 therein).

The cells were washed with assay buffer (100 μL), before addition of 25 μL of assay buffer and then 25 ul of assay buffer containing the putative P2X7 receptor antagonist compound. The cells were then incubated at room temperature (19-21° C.) for 30 min before addition of ATP solution (50 μM). Incubations were continued for 16 min and were terminated by addition of 25 μl of 1.28M sucrose containing 4 mM of the P2X7 receptor antagonist Reactive Black 5 (Aldrich). Cellular accumulation of ethidium was determined by measuring fluorescence (excitation wavelength of 535 nm and emission wavelength of 620 nm) from below the plate with an EnVision plate reader from Wallac (PerkinElmer, Life and Analytical Sciences, Via Tiepolo, 24, -20052 Monza, Italy). Antagonist $pIC_{50}$ values for blocking ATP responses were determined using iterative curve fitting techniques.

Fluorescent Imaging Plate Reader (FLIPR) Ca Assay

Studies were performed using NaCl assay buffer of the following composition for human P2X7: 137 mM NaCl; 20 mM HEPES [4-(2-hydroxyethyl)-1-piperazine-1-ethanesulfonic acid]; 5.37 mM KCl; 4.17 mM $NaHCO_3$; 1 mM $CaCl_2$; 0.5 mM $MgSO_4$; and 1 g/L of D-glucose (pH 7.4).

Human Embryonic Kidney (HEK) 293 cells, stably expressing human recombinant P2X7 receptors, were grown in poly-D-lysine pretreated 384 well plates for 24 hours at room temperature (for a time sufficient for growth of a homogeneous layer of cells at the bottom of the wells). Alternatively, human osteosarcoma (U-2OS) cells (commercially available), transduced with modified Baculovirus (BacMam) vector to deliver the gene coding for human P2X7 receptor (i.e. transiently expressing human recombinant P2X7 receptors), were grown in substantially the same conditions as for the HEK293 cells except that the well plates were not pretreated with poly-D-lysine. (The cloning of the human P2X7 receptor is described in U.S. Pat. No. 6,133,434, e.g. see Example 3 therein). The cells were washed three times with 800 of assay buffer, loaded for 1 h at 37° C. with 2 μM Fluo4-AM [4-(6-acetoxymethoxy-2,7-difluoro-3-oxo-9-xanthenyl)-4'-methyl-2,2'-(ethylenedioxy)dianiline-N,N,N', N'-tetraacetic acid tetrakis(acetoxymethyl)ester], a $Ca^{2+}$-sensitive, cell-permeable, fluorescent dye (Tef Labs. Inc., 9415 Capitol View Drive, Austin, Tex. 78747, USA), washed three times again (3×800), and left with 300 buffer before the addition of 100 of the assay buffer containing the putative P2X7 receptor antagonist compound, the compound being added at 4× the final assay concentration chosen. The solution of the putative P2X7 receptor antagonist compound was created by (i) dissolving the compound in dimethyl sulfoxide (DMSO) to create a stock solution in DMSO at 200× the final assay concentration, and (ii) mixing 10 of the stock solution of the compound in DMSO with 500 of the assay buffer to create a solution at about 4× the final assay concentration. The cells were then incubated at room temperature for 30 mins before addition (online, by FLIPR384 or FLIPR3 instrument (Molecular Devices, 1311 Orleans Drive, Sunnyvale, Calif. 94089-1136, USA)) of 100 of the assay buffer containing benzoylbenzoyl-ATP (BzATP) such as to create a 60 μM final assay concentration of BzATP (BzATP was added at 5× this final concentration). The BzATP concentration was chosen to be close to the $EC_{80}$ for the receptor type. Incubations and reading were continued for 90 sec, and intracellular calcium increase was determined by measuring fluorescence (excitation wavelength of 488 nm and emission wavelength of 516 nm) from below the plate, with FLIPR charged-coupled device (CCD) camera. Antagonist $pIC_{50}$ values for blocking BzATP responses were determined using iterative curve fitting techniques.

In the above FLIPR Ca Assay (or a slightly modified version thereof) for human P2X7 receptor antagonist activity, the compounds of Examples 1-14, 17-27, 30, 33, and 34 were found to have pIC50 values of about 4.8 or above in the FLIPR Ca Assay or a slightly modified version thereof.

The compounds of Examples 1-15, 17-28, and 30-34 were tested in the Ethidium Accumulation Assay (or a slightly modified version thereof) for human P2X7 receptor antagonist activity, and were found to have pIC50 values of from about 6.1 to about 8.6 (sometimes as a mean of more than one measurement) in the Ethidium Accumulation Assay or a slightly modified version thereof. The results obtained are shown in the table below wherein an entry of # indicates a pIC50 value of 6.0 or higher, an entry of * indicates a pIC50 value of 6.3 or higher, an entry of  indicates a pIC50 value of 7.0 or higher and an entry of * indicates a pIC50 value of 8.0 or higher.

| Ex | Structure | Name | Assay 1 | Assay 2 |
|---|---|---|---|---|
| 1 | 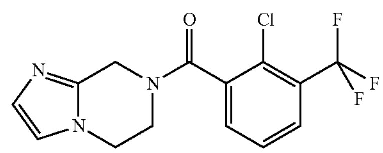 [SMILES: O=C(c1cccc(C(F)(F)F)c1Cl)N1CCn2ccnc2C1] | 7-{[2-Chloro-3-(trifluoromethyl)phenyl]carbonyl}-5,6,7,8-tetrahydroimidazo[1,2-a]pyrazine |  |  |
| 2 | 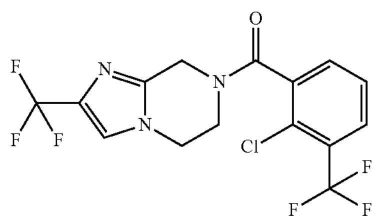 [SMILES: O=C(c1cccc(C(F)(F)F)c1Cl)N1CCn2cc(C(F)(F)F)nc2C1] | 7-{[2-Chloro-3-(trifluoromethyl)phenyl]carbonyl}-2-(trifluoromethyl)-5,6,7,8-tetrahydroimidazo[1,2-a]pyrazine |  |  |
| 3 | 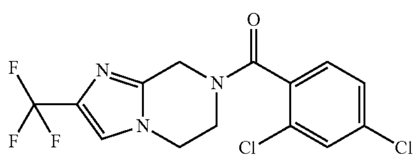 [SMILES: O=C(c1ccc(Cl)cc1Cl)N1CCn2cc(C(F)(F)F)nc2C1] | 7-[(2,4-Dichlorophenyl)carbonyl]-2-(trifluoromethyl)-5,6,7,8-tetrahydroimidazo[1,2-a]pyrazine | # | |
| 4 | 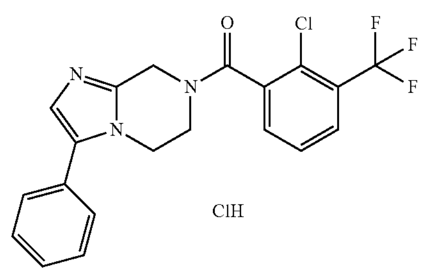 [SMILES: O=C(c1cccc(C(F)(F)F)c1Cl)N1CCn2c(-c3ccccc3)cnc2C1 ; Cl] | 7-{[2-chloro-3-(trifluoromethyl)phenyl]carbonyl}-3-phenyl-5,6,7,8-tetrahydroimidazo[1,2-a]pyrazine hydrochloride | *** | |
| 5 | 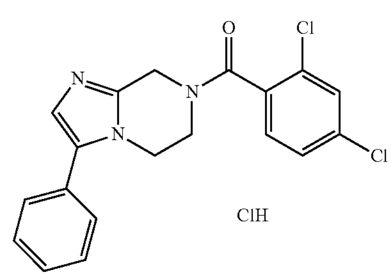 [SMILES: O=C(c1ccc(Cl)cc1Cl)N1CCn2c(-c3ccccc3)cnc2C1 ; Cl] | 7-[(2,4-dichlorophenyl)carbonyl]-3-phenyl-5,6,7,8-tetrahydroimidazo[1,2-a]pyrazine hydrochloride | ** | |
| 6 | 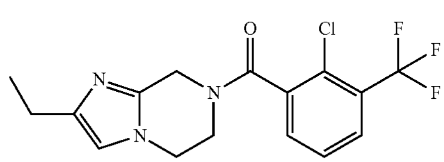 [SMILES: CCc1cn2c(n1)CN(C(=O)c1cccc(C(F)(F)F)c1Cl)CC2] | 7-{[2-chloro-3-(trifluoromethyl)phenyl]carbonyl}-2-ethyl-5,6,7,8-tetrahydroimidazo[1,2-a]pyrazine | ** | |

-continued

| Ex | Structure | Name | Assay 1 | Assay 2 |
|---|---|---|---|---|
| 7 | 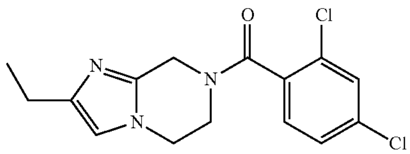 [SMILES: CCc1cn2c(n1)CN(C(=O)c1ccc(Cl)cc1Cl)CC2] | 7-[(2,4-dichlorophenyl)carbonyl]-2-ethyl-5,6,7,8-tetrahydroimidazo[1,2-a]pyrazine | # | |
| 8 | 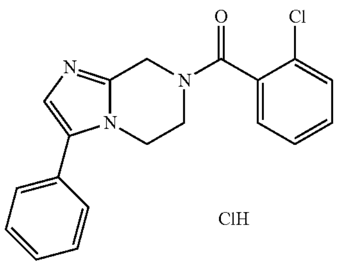 [SMILES: O=C(c1ccccc1Cl)N1CCn2c(-c3ccccc3)cnc2C1 ; Cl] | 7-[(2-chlorophenyl)carbonyl]-3-phenyl-5,6,7,8-tetrahydroimidazo[1,2-a]pyrazine hydrochloride | ** | |
| 9 | 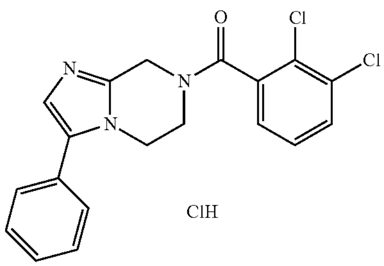 [SMILES: O=C(c1cccc(Cl)c1Cl)N1CCn2c(-c3ccccc3)cnc2C1 ; Cl] | 7-[(2,3-dichlorophenyl)carbonyl]-3-phenyl-5,6,7,8-tetrahydroimidazo[1,2-a]pyrazine hydrochloride | *** | |
| 10 | 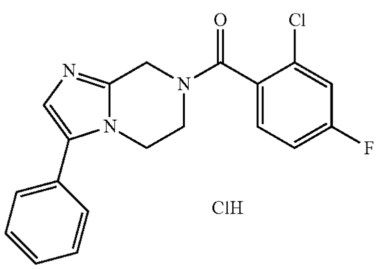 [SMILES: O=C(c1ccc(F)cc1Cl)N1CCn2c(-c3ccccc3)cnc2C1 ; Cl] | 7-[(2-chloro-4-fluorophenyl)carbonyl]-3-phenyl-5,6,7,8-tetrahydroimidazo[1,2-a]pyrazine hydrochloride | ** | |
| 11 | 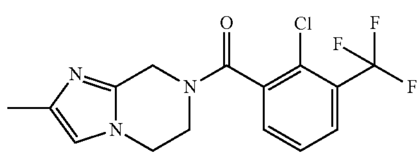 [SMILES: Cc1cn2c(n1)CN(C(=O)c1cccc(C(F)(F)F)c1Cl)CC2] | 7-{[2-chloro-3-(trifluoromethyl)phenyl]carbonyl}-2-methyl-5,6,7,8-tetrahydroimidazo[1,2-a]pyrazine | * | |
| 12 | 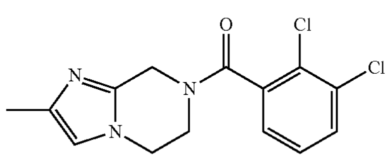 [SMILES: Cc1cn2c(n1)CN(C(=O)c1cccc(Cl)c1Cl)CC2] | 7-[(2,3-dichlorophenyl)carbonyl]-2-methyl-5,6,7,8-tetrahydroimidazo[1,2-a]pyrazine | * | |
| 13 | 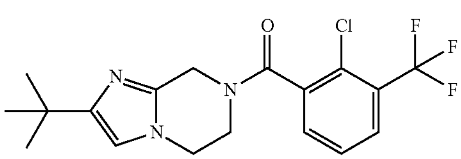 | 7-{[2-chloro-3-(trifluoromethyl)phenyl]carbonyl}-2-(1,1-dimethylethyl)-5,6,7,8-tetrahydroimidazo[1,2-a]pyrazine hydrochloride | # | |

-continued

| Ex | Structure | Name | Assay 1 | Assay 2 |
|---|---|---|---|---|
| 14 | 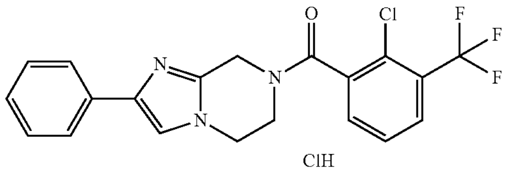 [SMILES: O=C(c1cccc(C(F)(F)F)c1Cl)N1CCn2cc(-c3ccccc3)nc2C1 ; Cl] | 7-{[2-chloro-3-(trifluoromethyl)phenyl]carbonyl}-2-phenyl-5,6,7,8-tetrahydroimidazo[1,2-a]pyrazine hydrochloride | * | |
| 15 | 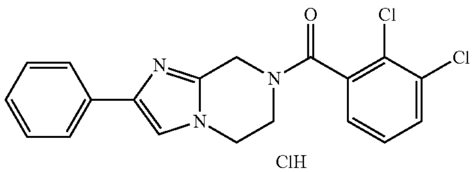 [SMILES: O=C(c1cccc(Cl)c1Cl)N1CCn2cc(-c3ccccc3)nc2C1 ; Cl] | 7-[(2,3-dichlorophenyl)carbonyl]-2-phenyl-5,6,7,8-tetrahydroimidazo[1,2-a]pyrazine hydrochloride | # | |
| 16 | 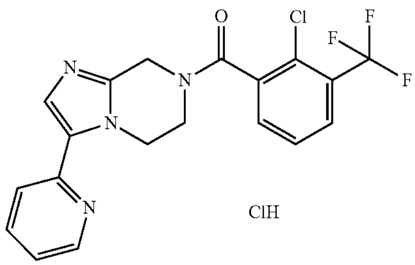 [SMILES: O=C(c1cccc(C(F)(F)F)c1Cl)N1CCn2c(-c3ccccn3)cnc2C1 ; Cl] | a hydrochloride (n•HCl) salt of 7-{[2-chloro-3-(trifluoromethyl)phenyl]carbonyl}-3-(2-pyridinyl)-5,6,7,8-tetrahydroimidazo[1,2-a]pyrazine | *** | |
| 17 | 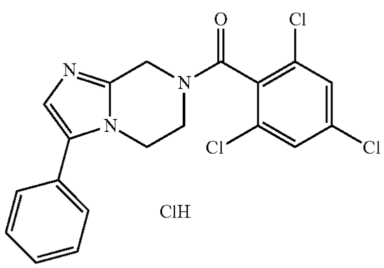 [SMILES: O=C(c1c(Cl)cc(Cl)cc1Cl)N1CCn2c(-c3ccccc3)cnc2C1 ; Cl] | 3-Phenyl-7-[(2,4,6-trichlorophenyl)carbonyl]-5,6,7,8-tetrahydroimidazo[1,2-a]pyrazine hydrochloride | ** | |
| 18 | 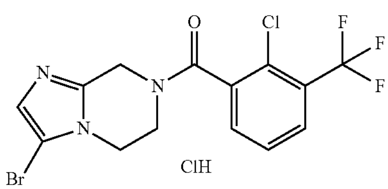 [SMILES: O=C(c1cccc(C(F)(F)F)c1Cl)N1CCn2c(Br)cnc2C1 ; Cl] | 3-Bromo-7-{[2-chloro-3-(trifluoromethyl)phenyl]carbonyl}-5,6,7,8-tetrahydroimidazo[1,2-a]pyrazine hydrochloride | *** | |
| 19 | 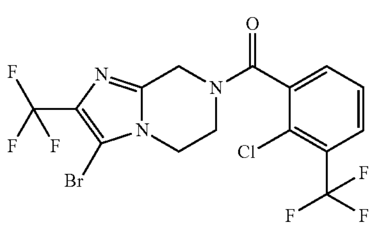 [SMILES: O=C(c1cccc(C(F)(F)F)c1Cl)N1CCn2c(nc(C(F)(F)F)c2Br)C1] | 3-Bromo-7-{[2-chloro-3-(trifluoromethyl)phenyl]carbonyl}-2-(trifluoromethyl)-5,6,7,8-tetrahydroimidazo[1,2-a]pyrazine | *** | |
| 20 | 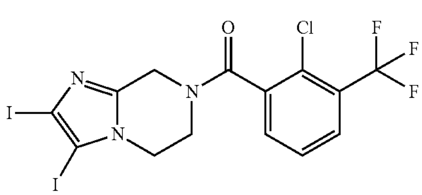 [SMILES: O=C(c1cccc(C(F)(F)F)c1Cl)N1CCn2c(nc(I)c2I)C1] | 7-{[2-Chloro-3-(trifluoromethyl)phenyl]carbonyl}-2,3-diiodo-5,6,7,8-tetrahydroimidazo[1,2-a]pyrazine | *** | |

| Ex | Structure | Name | Assay 1 | Assay 2 |
|---|---|---|---|---|
| 21 | 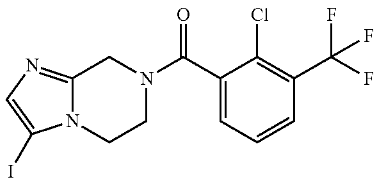 [SMILES: O=C(c1cccc(C(F)(F)F)c1Cl)N1CCn2c(I)cnc2C1] | 7-{[2-chloro-3-(trifluoromethyl)phenyl]carbonyl}-3-iodo-5,6,7,8-tetrahydroimidazo[1,2-a]pyrazine | *** | |
| 22 | 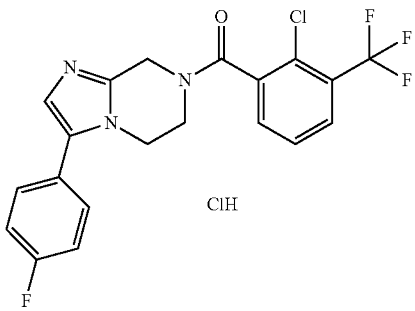 [SMILES: O=C(c1cccc(C(F)(F)F)c1Cl)N1CCn2c(-c3ccc(F)cc3)cnc2C1 ; Cl] | 7-{[2-Chloro-3-(trifluoromethyl)phenyl]carbonyl}-3-(4-fluorophenyl)-5,6,7,8-tetrahydroimidazo[1,2-a]pyrazine hydrochloride | ** | |
| 23 | 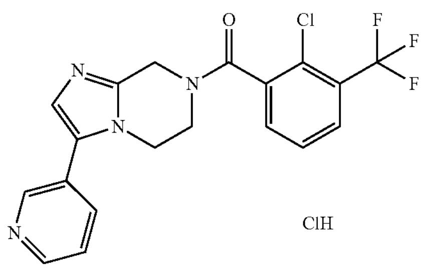 [SMILES: O=C(c1cccc(C(F)(F)F)c1Cl)N1CCn2c(-c3cccnc3)cnc2C1 ; Cl] | a hydrochloride salt (n•HCl) of 7-{[2-chloro-3-(trifluoromethyl)phenyl]carbonyl}-3-(3-pyridinyl)-5,6,7,8-tetrahydroimidazo[1,2-a]pyrazine | *** | |
| 24 | 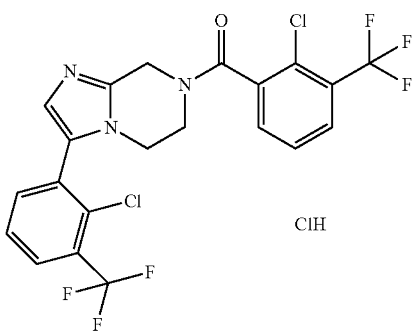 [SMILES: O=C(c1cccc(C(F)(F)F)c1Cl)N1CCn2c(-c3cccc(C(F)(F)F)c3Cl)cnc2C1 ; Cl] | 3-[2-chloro-3-(trifluoromethyl)phenyl]-7-{[2-chloro-3-(trifluoromethyl)phenyl]carbonyl}-5,6,7,8-tetrahydroimidazo[1,2-a]pyrazine hydrochloride | # | |
| 25 | 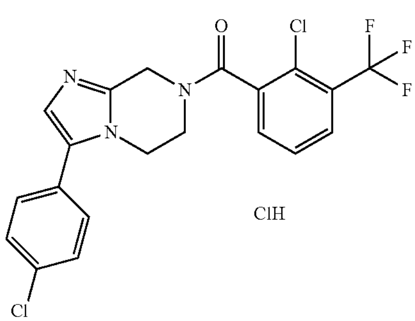 [SMILES: O=C(c1cccc(C(F)(F)F)c1Cl)N1CCn2c(-c3ccc(Cl)cc3)cnc2C1 ; Cl] | 3-(4-chlorophenyl)-7-{[2-chloro-3-(trifluoromethyl)phenyl]carbonyl}-5,6,7,8-tetrahydroimidazo[1,2-a]pyrazine hydrochloride | * | |

| Ex | Structure | Name | Assay 1 | Assay 2 |
|---|---|---|---|---|
| 26 | 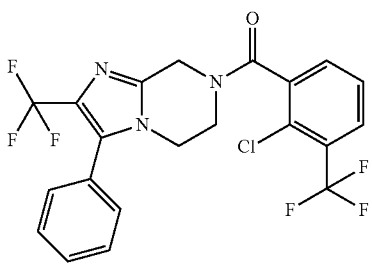 [SMILES: O=C(c1cccc(C(F)(F)F)c1Cl)N1CCn2c(nc(C(F)(F)F)c2-c2ccccc2)C1] | 7-{[2-Chloro-3-(trifluoromethyl)phenyl]carbonyl}-3-phenyl-2-(trifluoromethyl)-5,6,7,8-tetrahydroimidazo[1,2-a]pyrazine | ** | |
| 27 | 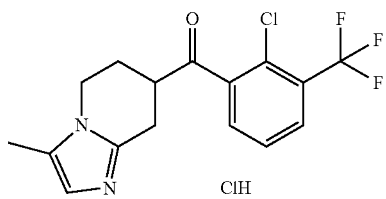 [SMILES: Cc1cnc2n1CCC(C(=O)c1cccc(C(F)(F)F)c1Cl)C2 ; Cl] | 7-{[2-Chloro-3-(trifluoromethyl)phenyl]carbonyl}-3-methyl-5,6,7,8-tetrahydroimidazo[1,2-a]pyrazine hydrochloride |  |  |
| 28 | 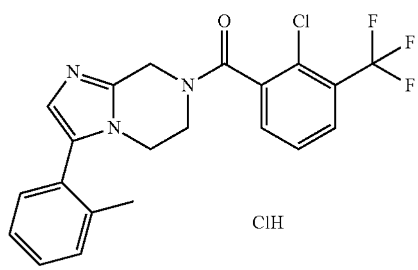 [SMILES: Cc1ccccc1-c1cnc2n1CCN(C(=O)c1cccc(C(F)(F)F)c1Cl)C2 ; Cl] | 7-{[2-Chloro-3-(trifluoromethyl)phenyl]carbonyl}-3-(2-methylphenyl)-5,6,7,8-tetrahydroimidazo[1,2-a]pyrazine hydrochloride | ** | |
| 29 | 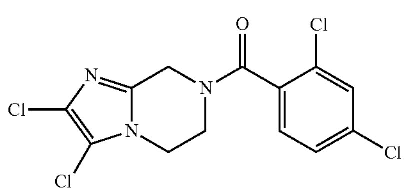 [SMILES: O=C(c1ccc(Cl)cc1Cl)N1CCn2c(nc(Cl)c2Cl)C1] | 2,3-dichloro-7-[(2,4-dichlorophenyl)carbonyl]-5,6,7,8-tetrahydroimidazo[1,2-a]pyrazine | ** | |
| 30 | 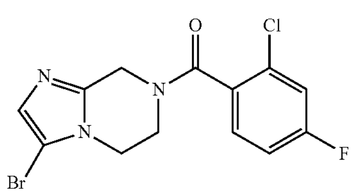 [SMILES: O=C(c1ccc(F)cc1Cl)N1CCn2c(Br)cnc2C1] | 3-Bromo-7-[(2-chloro-4-fluorophenyl)carbonyl]-5,6,7,8-tetrahydroimidazo[1,2-a]pyrazine | * | |
| 31 | 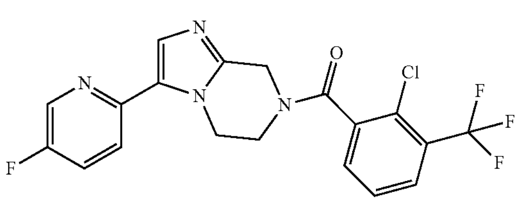 [SMILES: O=C(c1cccc(C(F)(F)F)c1Cl)N1CCn2c(-c3ccc(F)cn3)cnc2C1] | 7-{[2-Chloro-3-(trifluoromethyl)phenyl]carbonyl}-3-(5-fluoro-2-pyridinyl)-5,6,7,8-tetrahydroimidazo[1,2-a]pyrazine | *** | |
| 32 | 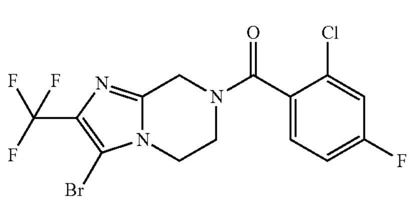 [SMILES: O=C(c1ccc(F)cc1Cl)N1CCn2c(nc(C(F)(F)F)c2Br)C1] | 3-Bromo-7-[(2-chloro-4-fluorophenyl)carbonyl]-2-(trifluoromethyl)-5,6,7,8-tetrahydroimidazo[1,2-a]pyrazine | ** | |

-continued

| Ex | Structure | Name | Assay 1 | Assay 2 |
|---|---|---|---|---|
| 33 | 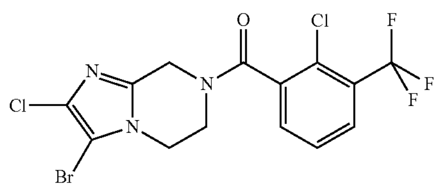 [SMILES: O=C(c1cccc(C(F)(F)F)c1Cl)N1CCn2c(nc(Cl)c2Br)C1] | 3-Bromo-2-chloro-7-{[2-chloro-3-(trifluoromethyl)phenyl]carbonyl}-5,6,7,8-tetrahydroimidazo[1,2-a]pyrazine | *** | |
| 34 | 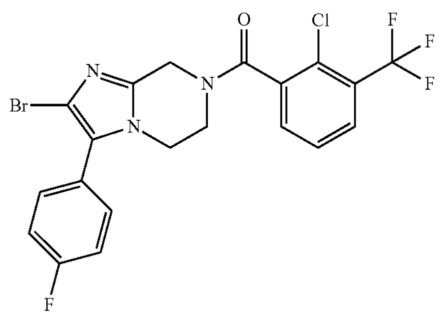 [SMILES: O=C(c1cccc(C(F)(F)F)c1Cl)N1CCn2c(nc(Br)c2-c2ccc(F)cc2)C1] | 2-Bromo-7-{[2-chloro-3-(trifluoromethyl)phenyl]carbonyl}-3-(4-fluorophenyl)-5,6,7,8-tetrahydroimidazo[1,2-a]pyrazine | ** | |
| 35 | 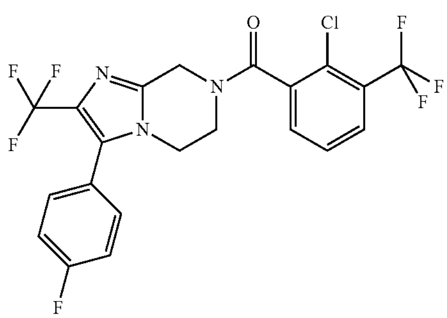 [SMILES: O=C(c1cccc(C(F)(F)F)c1Cl)N1CCn2c(nc(C(F)(F)F)c2-c2ccc(F)cc2)C1] | 7-{[2-chloro-3-(trifluoromethyl)phenyl]carbonyl}-3-(4-fluorophenyl)-2-(trifluoromethyl)-5,6,7,8-tetrahydroimidazo[1,2-a]pyrazine | ** | |
| 36 | 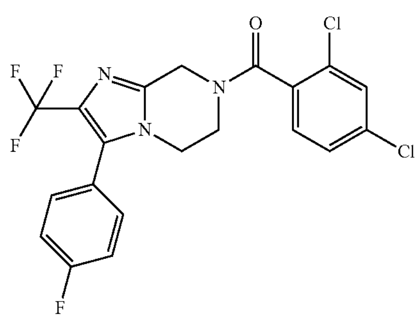 [SMILES: O=C(c1ccc(Cl)cc1Cl)N1CCn2c(nc(C(F)(F)F)c2-c2ccc(F)cc2)C1] | 7-[(2,4-dichlorophenyl)carbonyl]-3-(4-fluorophenyl)-2-(trifluoromethyl)-5,6,7,8-tetrahydroimidazo[1,2-a]pyrazine | * | |
| 37 | 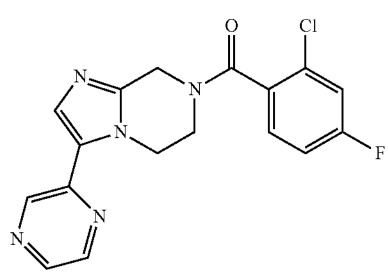 [SMILES: O=C(c1ccc(F)cc1Cl)N1CCn2c(-c3cnccn3)cnc2C1] | 7-[(2-chloro-4-fluorophenyl)carbonyl]-3-(2-pyrazinyl)-5,6,7,8-tetrahydroimidazo[1,2-a]pyrazine | *** | |

-continued

| Ex | Structure | Name | Assay 1 | Assay 2 |
|---|---|---|---|---|
| 38 | 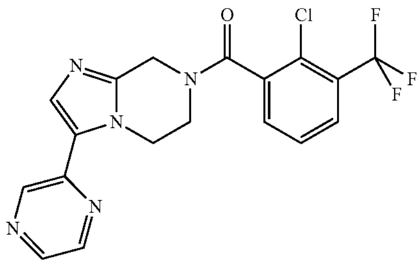 [SMILES: O=C(c1cccc(C(F)(F)F)c1Cl)N1CCn2c(-c3cnccn3)cnc2C1] | 7-{[2-chloro-3-(trifluoromethyl)phenyl]carbonyl}-3-(2-pyrazinyl)-5,6,7,8-tetrahydroimidazo[1,2-a]pyrazine | *** | |
| 39 | 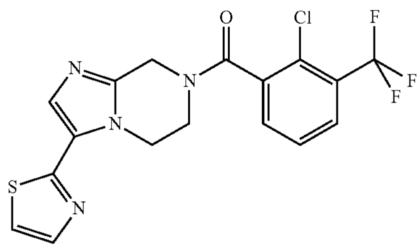 [SMILES: O=C(c1cccc(C(F)(F)F)c1Cl)N1CCn2c(-c3nccs3)cnc2C1] | 7-{[2-chloro-3-(trifluoromethyl)phenyl]carbonyl}-3-(1,3-thiazol-2-yl)-5,6,7,8-tetrahydroimidazo[1,2-a]pyrazine | *** | |
| 40 | 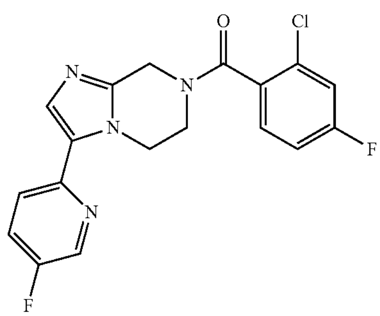 [SMILES: O=C(c1ccc(F)cc1Cl)N1CCn2c(-c3ccc(F)cn3)cnc2C1] | 7-[(2-chloro-4-fluorophenyl)carbonyl]-3-(2-pyrazinyl)-5,6,7,8-tetrahydroimidazo[1,2-a]pyrazine | ** | |
| 41 | 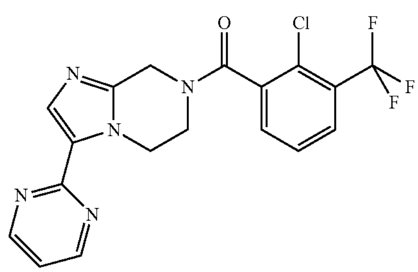 [SMILES: O=C(c1cccc(C(F)(F)F)c1Cl)N1CCn2c(-c3ncccn3)cnc2C1] | 7-{[2-chloro-3-(trifluoromethyl)phenyl]carbonyl}-3-(2-pyrimidinyl)-5,6,7,8-tetrahydroimidazo[1,2-a]pyrazine | *** | |
| 42 | 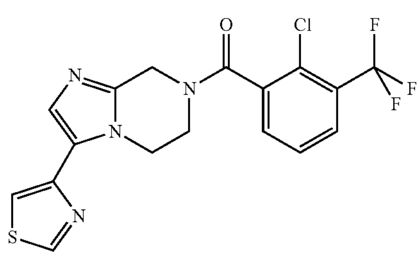 [SMILES: O=C(c1cccc(C(F)(F)F)c1Cl)N1CCn2c(-c3cscn3)cnc2C1] | 7-{[2-chloro-3-(trifluoromethyl)phenyl]carbonyl}-3-(1,3-thiazol-4-yl)-5,6,7,8-tetrahydroimidazo[1,2-a]pyrazine | *** | |
| 43 | 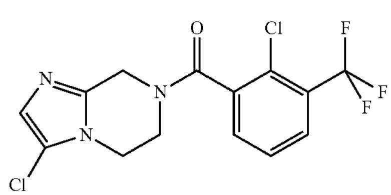 [SMILES: O=C(c1cccc(C(F)(F)F)c1Cl)N1CCn2c(Cl)cnc2C1] | 3-chloro-7-{[2-chloro-3-(trifluoromethyl)phenyl]carbonyl}-5,6,7,8-tetrahydroimidazo[1,2-a]pyrazine | ** | |

| Ex | Structure | Name | Assay 1 | Assay 2 |
|---|---|---|---|---|
| 44 | 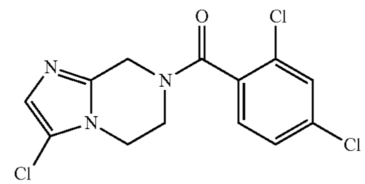 [SMILES: O=C(c1ccc(Cl)cc1Cl)N1CCn2c(Cl)cnc2C1] | 3-chloro-7-[(2,4-dichlorophenyl)carbonyl]-5,6,7,8-tetrahydroimidazo[1,2-a]pyrazine | * | |
| 45 | 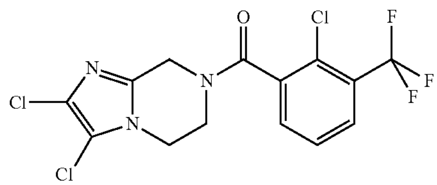 | 2,3-dichloro-7-{[2-chloro-3-(trifluoromethyl)phenyl]cabonyl}-5,6,7,8-tetrahydroimidazo[1,2-a]pyrazine | *** | |

The invention claimed is:

1. A compound of formula (I) or a pharmaceutically acceptable salt thereof:

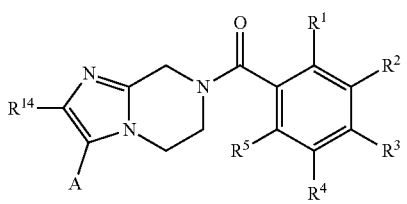

(I)

wherein:
A is hydrogen, $C_{1-4}$alkyl, $C_{3-6}$cycloalkyl, $C_{1-3}$alkoxy, $C_{1-3}$alkoxy $C_{1-4}$alkyl, $C_{1-2}$fluoroalkyl, halogen, $NR^6R^7$, Het, or phenyl wherein said phenyl is optionally substituted by one, two or three substituents independently being fluorine, chlorine, $C_{1-3}$alkyl, OH, methoxy or deuterium;
wherein Het is:
i) a 6-membered heteroaromatic monocyclic ring containing one, two or three ring-nitrogen atoms, or
ii) a 5-membered heteroaromatic monocyclic ring containing one, two or three ring heteroatoms independently being N, O or S, wherein no more than one of the 5-membered ring heteroatoms is O or S; or
iii) a 9 or 10-membered heteroaromatic bicyclic ring containing one, two or three ring nitrogen atoms;
and wherein Het is optionally substituted with one or two substituents independently being $C_{1-3}$ alkyl, fluorine, chlorine, OH, methoxy or deuterium;
and wherein:
$R^1$ is hydrogen, chlorine, fluorine, bromine, $C_1$fluoroalkyl, cyano or $C_{1-3}$alkyl;
$R^2$ is hydrogen, fluorine, chlorine, bromine, $C_1$fluoroalkyl, cyano or $C_{1-3}$alkyl,
$R^3$ is hydrogen, fluorine, chlorine or $C_{1-3}$alkyl,
$R^4$ is hydrogen;
$R^5$ is hydrogen, fluorine, chlorine or methyl;
$R^6$ and $R^7$ independently are hydrogen or $C_{1-3}$alkyl;
or $R^6$ and $R^7$ are taken together and are —$(CH_2)_2$—O—$(CH_2)_2$—, —$(CH_2)_2$—O—$(CH_2)_3$—, or —$(CH_2)_{n^1}$— wherein $n^1$ is 3, 4, 5 or 6; and
$R^{14}$ is hydrogen, $C_{1-6}$alkyl, $C_{1-2}$fluoroalkyl, $C_{3-6}$cycloalkyl, halogen, or phenyl wherein said phenyl is optionally substituted by one or two substituents independently being fluorine, chlorine, methyl, —$CF_3$ or methoxy;
wherein, when A is hydrogen, $C_{1-4}$alkyl, $C_{1-3}$alkoxy, $C_{1-3}$alkoxy $C_{1-4}$alkyl, $C_{1-2}$fluoroalkyl, halogen or $NR^6R^7$, then $R^1$ is chlorine, fluorine, bromine, $C_1$fluoroalkyl, cyano or $C_{1-3}$alkyl, and at least one of $R^2$ and $R^3$ is other than hydrogen;
and when A is Het or optionally substituted phenyl, then $R^1$ is hydrogen, chlorine, fluorine, bromine, $C_1$fluoroalkyl, cyano or $C_{1-3}$alkyl, at least one of $R^1$, $R^2$ and $R^3$ is other than hydrogen, and $R^{14}$ is hydrogen, $C_{1-6}$alkyl, $C_{1-2}$fluoroalkyl, $C_{3-6}$cycloalkyl or halogen;
and wherein, when $R^5$ is fluorine, chlorine or methyl, then $R^1$ is chlorine, fluorine, $C_1$fluoroalkyl or methyl and $R^2$ is hydrogen.

2. A pharmaceutical composition which comprises the compound or salt as defined in claim 1 and a pharmaceutically acceptable carrier or excipient.

3. A compound which is:
7-{[2-chloro-3-(trifluoromethyl)phenyl]carbonyl}-5,6,7,8-tetrahydroimidazo[1,2-a]pyrazine,
7-{[2-chloro-3-(trifluoromethyl)phenyl]carbonyl}-2-(trifluoromethyl)-5,6,7,8-tetrahydroimidazo[1,2-a]pyrazine,
7-[(2,4-dichlorophenyl)carbonyl]-2-(trifluoromethyl)-5,6,7,8-tetrahydroimidazo[1,2-a]pyrazine,
7-{[2-chloro-3-(trifluoromethyl)phenyl]carbonyl}-3-phenyl-5,6,7,8-tetrahydroimidazo[1,2-a]pyrazine,
7-[(2,4-dichlorophenyl)carbonyl]-3-phenyl-5,6,7,8-tetrahydroimidazo[1,2-a]pyrazine,
7-{[2-chloro-3-(trifluoromethyl)phenyl]carbonyl}-2-ethyl-5,6,7,8-tetrahydroimidazo[1,2-a]pyrazine,
7-[(2,4-dichlorophenyl)carbonyl]-2-ethyl-5,6,7,8-tetrahydroimidazo[1,2-a]pyrazine,
7-[(2-chlorophenyl)carbonyl]-3-phenyl-5,6,7,8-tetrahydroimidazo[1,2-a]pyrazine,
7-[(2,3-dichlorophenyl)carbonyl]-3-phenyl-5,6,7,8-tetrahydroimidazo[1,2-a]pyrazine,
7-[(2-chloro-4-fluorophenyl)carbonyl]-3-phenyl-5,6,7,8-tetrahydroimidazo[1,2-a]pyrazine,
7-{[2-chloro-3-(trifluoromethyl)phenyl]carbonyl}-2-methyl-5,6,7,8-tetrahydroimidazo[1,2-a]pyrazine,
7-[(2,3-dichlorophenyl)carbonyl]-2-methyl-5,6,7,8-tetrahydroimidazo[1,2-a]pyrazine, 7-{[2-chloro-3-(trifluoromethyl)phenyl]carbonyl}-2-(1,1-dimethylethyl)-5,6,7,8-tetrahydroimidazo[1,2-a]pyrazine,
7-{[2-chloro-3-(trifluoromethyl)phenyl]carbonyl}-2-phenyl-5,6,7,8-tetrahydroimidazo[1,2-a]pyrazine,
7-[(2,3-dichlorophenyl)carbonyl]-2-phenyl-5,6,7,8-tetrahydroimidazo[1,2-a]pyrazine,
7-{[2-chloro-3-(trifluoromethyl)phenyl]carbonyl}-3-(2-pyridinyl)-5,6,7,8-tetrahydroimidazo[1,2-a]pyrazine,
3-phenyl-7-[(2,4,6-trichlorophenyl)carbonyl]-5,6,7,8-tetrahydroimidazo[1,2-a]pyrazine,
3-bromo-7-{[2-chloro-3-(trifluoromethyl)phenyl]carbonyl}-5,6,7,8-tetrahydroimidazo[1,2-a]pyrazine,
3-bromo-7-{[2-chloro-3-(trifluoromethyl)phenyl]carbonyl}-2-(trifluoromethyl)-5,6,7,8-tetrahydroimidazo[1,2-a]pyrazine,
7-{[2-chloro-3-(trifluoromethyl)phenyl]carbonyl}-2,3-diiodo-5,6,7,8-tetrahydroimidazo[1,2-a]pyrazine,
7-{[2-chloro-3-(trifluoromethyl)phenyl]carbonyl}-3-iodo-5,6,7,8-tetrahydroimidazo[1,2-a]pyrazine,
7-{[2-chloro-3-(trifluoromethyl)phenyl]carbonyl}-3-(4-fluorophenyl)-5,6,7,8-tetrahydroimidazo[1,2-a]pyrazine,
7-{[2-chloro-3-(trifluoromethyl)phenyl]carbonyl}-3-(3-pyridinyl)-5,6,7,8-tetrahydroimidazo[1,2-a]pyrazine,
3-[2-chloro-3-(trifluoromethyl)phenyl]-7-{[2-chloro-3-(trifluoromethyl)phenyl]carbonyl}-5,6,7,8-tetrahydroimidazo[1,2-a]pyrazine,
3-(4-chlorophenyl)-7-{[2-chloro-3-(trifluoromethyl)phenyl]carbonyl}-5,6,7,8-tetrahydroimidazo[1,2-a]pyrazine,
7-{[2-chloro-3-(trifluoromethyl)phenyl]carbonyl}-3-phenyl-2-(trifluoromethyl)-5,6,7,8-tetrahydroimidazo[1,2-a]pyrazine,
7-{[2-chloro-3-(trifluoromethyl)phenyl]carbonyl}-3-methyl-5,6,7,8-tetrahydroimidazo[1,2-a]pyrazine,
7-{[2-chloro-3-(trifluoromethyl)phenyl]carbonyl}-3-(2-methylphenyl)-5,6,7,8-tetrahydroimidazo[1,2-a]pyrazine,
3-bromo-7-[(2-chloro-4-fluorophenyl)carbonyl]-5,6,7,8-tetrahydroimidazo[1,2-a]pyrazine,
7-{[2-chloro-3-(trifluoromethyl)phenyl]carbonyl}-3-(5-fluoro-2-pyridinyl)-5,6,7,8-tetrahydroimidazo[1,2-a]pyrazine,
3-bromo-7-[(2-chloro-4-fluorophenyl)carbonyl]-2-(trifluoromethyl)-5,6,7,8-tetrahydroimidazo[1,2-a]pyrazine,
3-bromo-2-chloro-7-{[2-chloro-3-(trifluoromethyl)phenyl]carbonyl}-5,6,7,8-tetrahydroimidazo[1,2-a]pyrazine,
2-bromo-7-{[2-chloro-3-(trifluoromethyl)phenyl]carbonyl}-3-(4-fluorophenyl)-5,6,7,8-tetrahydroimidazo[1,2-a]pyrazine
2,3-dichloro-7-[(2,4-dichlorophenyl)carbonyl]-5,6,7,8-tetrahydroimidazo[1,2-a]pyrazine,
7-{[2-chloro-3-(trifluoromethyl)phenyl]carbonyl}-3-(4-fluorophenyl)-2-(trifluoromethyl)-5,6,7,8-tetrahydroimidazo[1,2-a]pyrazine,
7-[(2,4-dichlorophenyl)carbonyl]-3-(4-fluorophenyl)-2-(trifluoromethyl)-5,6,7,8-tetrahydroimidazo[1,2-a]pyrazine,
7-[(2-chloro-4-fluorophenyl)carbonyl]-3-(2-pyrazinyl)-5,6,7,8-tetrahydroimidazo[1,2-a]pyrazine,
7-{[2-chloro-3-(trifluoromethyl)phenyl]carbonyl}-3-(2-pyrazinyl)-5,6,7,8-tetrahydroimidazo[1,2-a]pyrazine,
7-{[2-chloro-3-(trifluoromethyl)phenyl]carbonyl}-3-(1,3-thiazol-2-yl)-5,6,7,8-tetrahydroimidazo[1,2-a]pyrazine,
7-[(2-chloro-4-fluorophenyl)carbonyl]-3-(2-pyrazinyl)-5,6,7,8-tetrahydroimidazo[1,2-a]pyrazine,
7-{[2-chloro-3-(trifluoromethyl)phenyl]carbonyl}-3-(2-pyrimidinyl)-5,6,7,8-tetrahydroimidazo[1,2-a]pyrazine,
7-{[2-chloro-3-(trifluoromethyl)phenyl]carbonyl}-3-(1,3-thiazol-4-yl)-5,6,7,8-tetrahydroimidazo[1,2-a]pyrazine,
3-chloro-7-{[2-chloro-3-(trifluoromethyl)phenyl]carbonyl}-5,6,7,8-tetrahydroimidazo[1,2-a]pyrazine,
3-chloro-7-[(2,4-dichlorophenyl)carbonyl]-5,6,7,8-tetrahydroimidazo[1,2-a]pyrazine, or
2,3-dichloro-7-{[2-chloro-3-(trifluoromethyl)phenyl]carbonyl}-5,6,7,8-tetrahydroimidazo[1,2-a]pyrazine;
or a pharmaceutically acceptable salt thereof.

* * * * *